United States Patent
Kwon

(10) Patent No.: US 6,362,325 B1
(45) Date of Patent: *Mar. 26, 2002

(54) MURINE 4-1BB GENE

(75) Inventor: Byoung S. Kwon, Carmel, IN (US)

(73) Assignee: Advanced Research and Technology Institute, Inc., Indianapolis, IN (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/012,269

(22) Filed: Feb. 1, 1993

Related U.S. Application Data

(63) Continuation-in-part of application No. 07/922,996, filed on Jul. 30, 1992, which is a continuation-in-part of application No. 07/267,577, filed on Nov. 7, 1988, now abandoned.

(51) Int. Cl.[7] .......................... C07H 21/04; C12P 21/02; C07K 1/00; G01N 33/566
(52) U.S. Cl. ............................ 536/23.5; 435/6; 435/7.2; 435/69.1; 435/69.5; 530/350; 530/351; 436/501
(58) Field of Search .................... 536/27, 23.5; 435/91, 435/69.5, 69.1, 6, 7.2; 530/350, 351; 935/9, 31, 41, 58, 73; 436/501

(56) References Cited

PUBLICATIONS

Lewin Science vol. 237 p. 1570 (1987).*
Reeck et al Cell vol. 50 p. 667 (1987).*
Shaw, A., et al, (1990) Mol. Cell. Bio., 10:1853–1862.
Chalupny, N., et al, (1992) Proc. Natl. Acad. Sci. USA 89:10360–10364.
Townsend, S. et al, (1993) Science, 259:366–370.
Lenschow,D. et al, (1992) Science, 257:789–792.
Linsley, P. et al, (1992) Science, 257:792–795.
Cohen, J., (1992) Science, 257:751.
Kwon, B. et al, (1989), Cell Immunol., 121:414–422.
Kwon, B. et al, (1984), Jol. of Virology, 52:1000–1004.
Kwon, B. et al, (1989) Biochem. & Biophys. Res.Comm., 158:1–10.
Kwon, B. et al, (1988), J. Exp. Med., 168:1839–1854.
Broxmeyer, H. E., B. Sherry, L. Lu, S. Cooper, C. Carow, S. D. Wolpe, and A. Cerami. 1989. Myelopoietic enhancing effects of murine macrophage inflammatory proteins and human bone marrow granulocyte/macrophage progenitor cells. J. Exp. Med. 170:1583.
Broxmeyer, H. E., B. Sherry, L. Lu, S. Cooper, K. O. Oh, P. Tekamp–Olson, B. S. Kwon, and A. Cerami. 1990. Enhancing and suppressing effects of recombinant murine macrophage inflammatory proteins on colony formation in vitro by bone marrow myeloid progenitor cells. Blood 76:1110.
Broxmeyer, H. E., and D. E. Williams (1988), The production of myeloid blood cells and their regulation during health and disease; CRC Crit. Rev. Oncol./Hematol. 8:173.
Broxmeyer H. E. 1991. Suppressor molecules and regulation of myelopoiesis: biology and possible clinical uses. Amer. J. Ped. Hematol/Oncol. in press. 14(1):22 (1992).
Davatelis, G., S.D. Wolpe, B. Sherry, J.M. Dayer, R. Chicheportiche, and A. Cerami. 1989. Macrophage inflammatory protein–1: a prostaglandin–independent endogenous pyrogen. Science 243:1066.
Davatelis, G., P. Tekamp–Olson, S.D. Wolpe, K. Hermsen, C. Luedke, C. Gallegos, D. Coit, J. Merryweather, and A. Cerami. 1988. Cloning and characterization of a cDNA for murine macrophage inflammatory protein (MIP), a novel monokine with inflammatory and chemokinetic properties. Journal of Experimental Medicine. 167:1939.
Fahey III, T.J., Sherry, B., Tracey, K.J., van Deventer, S., Jones II, W.G., Minei, J.P., Morgello, S., Shires, G.T. and Cerami, A. 1990. Cytokine production in a model of wound healing: the appearance of MIP–1, MIP–2, cachectin/TNF and IL–I. Cytokine, vol. 2, No. 2 (March), pp. 92–99.
Graham, G.J., E.G. Wright, R. Hewick, S.D. Wolpe, N.M. Wilkie, D. Donaldson, S. Lorimore, and I.B. Pragnell. 1990. Identification and characterization of an inhibitor of haemopoietic stem cell proliferation. Nature 344:442.
Broxmeyer, H.E., B. Sherry, S. Cooper, F.W. Ruscetti, D. E. Williams, P. Arosio, B.S. Kwon, A. Cerami. 1991. Macrophage inflammatory protein (MIP)–1β abrogates the capacity of MIP–1α to suppress myeloid progenitor cell growth. J. Immunol. 147:2586.

(List continued on next page.)

Primary Examiner—Yvonne Eyler
Assistant Examiner—Michael Brannock
(74) Attorney, Agent, or Firm—Schwegman, Lundberg Woessner & Kluth, P.A.

(57) ABSTRACT

The present invention includes the receptor protein 4-1BB and the cDNA gene encoding for receptor protein 4-1BB. The nucleotide sequence of the isolated cDNA is disclosed herein along with the deduced amino acid sequence. The 4-1BB protein and fragments and derivatives can be used: 1) as a probe to isolate ligands to receptor protein 4-1BB, 2) to stimulate proliferation of B-cell's expressing 4-1BB, or 3) to block 4-1BB ligand binding. A monoclonal antibody against 4-1BB was developed which specifically recognizes an epitope on the extracellular domain of receptor protein 4-1BB. The monoclonal antibody can be used enhance T-cell proliferation and activation by treating T-cells that have expressed receptor protein 4-1BB with the monoclonal antibody. The effectiveness of the treatment was enhanced when conducted in the presence of protein tyrosinase kinase. A fusion protein for detecting cell membrane ligands to receptor protein 4-1BB was developed. It comprises the extracellular portion of the receptor protein 4-1BB and a detection protein bound to the portion of the receptor protein 4-1BB.

7 Claims, 38 Drawing Sheets

OTHER PUBLICATIONS

Broxmeyer, H. E. 1990. Interacting effects of cytokines on hematopoietic stem and progenitor cells. In, Hematopoietic Growth Factors in Clinical Applications, Mertelsmann R, Herrmann F, eds, Marcel Dekker, Inc, New York NY, 3.

Lipes, M.A., M. Napolitano, K.T. Jeang, N.T. Chang, and W. J. Leonard. 1990. Identification, cloning and characterization of an immune activation Gene. Proc. Natl. Acad. Sci. USA. 85:9704.

Miller, M.D., S. Hata, R.D.W. Malefyt, and M.S. Krangel. 1989. A novel polypeptide secreted by activated human T lymphocytes. J. Immunol. 143:2907.

Minano, F.J., Sacibrian, M., Vizcaino, M., Paez, X., Davatelis, G., Fahey, T., Sherry, B., Cerami, A. and Myers, R.D. 1990. Macrophage inflammatory protein–1: unique action on the hypothalmus to evoke fever. Brain Res. Bull. vol. 24, pp. 849–852.

Oh, K.–O., Zhou, Z., Kim, K.–K., Samanta, H., Fraser, M., Kim, Y.–J., Broxmeyer, H.E. and Kwon, B.S. 1991. Identification of cell surface receptors for murine macrophage inflammatory protein–1α. J. Immunol. vol. 147, pp. 2978–2983.

Oppenheim, J. J., C. O. C. Zachariae, N., Mukaido, and K. Matsushima. 1991. Properties of the novel proinflammatory supergene "intercrine" cytokine family. Ann. Rev. Immunol. 9: 617.

Sherry, B., P. Tekamp–Olson, C. Gallegos, D. Bauer, G. Davatelis, S. Wolpe, F. Masiarz, D. Coit, and A. Cerami. 1988. Resolution of the two components of macrophage inflammatory protein 1, and cloning and characterization of one of those components, macrophage inflammatory protein 1β. Journal of Experimental Medicine. 168:2251.

Tekamp–Olson, P., C. Gallegos, D. Bauer, J. McClain, B. Sherry, M. Fabre, S. Van Deventer, and A. Cerami. 1990. Cloning and characterization of cDNAs for murine macrophage inflammatory protein 2 and its human homologues. J. Exp. Med. 171:911.

Wolpe, S. D. and A. Cerami. 1989. Macrophage inflammatory proteins 1 and 2: members of a novel superfamily of cytokines. FASEB J. 3:2565.

Wolpe, S. D., B. Sherry, D. Juers, G. Davatelis, R. W. Yurt, and A. Cerami. 1989. Identification and characterization of macrophage inflammatory protein 2. Proc. Natl. Acad. Sci. USA 86:612.

Wolpe, S. D., G. Davatelis, B. Sherry, B. Buetler, D. G. Hesse, H. T. Hguyen, L. L. Moldawer, C. F. Nathan, S. F. Lowry, and A. Cerami. 1988. Macrophages secrete a novel heparin–binding protein with inflammatory and neutrophil chemokinetic properties. J. Exp. Med. 167:570.

Zipfel, P.F., J. Balke, S.G. Irving, K. Kelly, and U. Siebenlist. 1989. Mitogenic activation of human T cells induces two closely related genes which share structural similarities with a new family of secreted factors. J. Immunol. 142:1582.

Dunlop, D., Wright, E.G., Lorimore, S., Graham, T., Holyoake, T., Kerr, D. J. Wolpe, S.D., and Pragnell, I.B. 1991. Demonstration of Stem Cell Inhibition and Myeloproteactive Effects of SCI/rhMIP1α In Vivo. Blood, vol. 79., (May 1, 1992) pp. 2221–2225.

Schall, T.J., Jongstra, J., Dryer, B.J., Jorgensen, J., Clayberger, C., Davis, M.M. and Krensky, A.M., 1988. A Human T Cell–Specific Molecule is a memeberof a New Gene Family. J. Immunol., vol. 141. Aug. 1988, pp. 1018–1025.

Cohen, J., Mounting a Targeted Strike on Unwanted Immune Responses, Science, vol. 257, Aug. 1992, p. 751.

Lenschow, D.J., Zeng, Y., Thistlethwaite, J.R., Mongag, A., Brady, W., Gibson, M.G., Linsley, P.S. and Bluestone, J.A., Long–Term Survival of Xenogeneic pancreatic Islet Grafts Induced by CTLA41g, Aug. 1992, Science, vol. 257., pp 789792.

Linsley, P.S., Wallace, P.M., Johnson, J., Gibson, M.G., Greene, J.L., Ledbetter, J.A., Singh, C. and Tepper, M.A., Aug. 1992, Immunosuppression in vivo by a Soluble Form of the CTLA–4 Cell Activation Molecule, Science, vol. 257, pp. 792–795.

Kwon, B.S., G.S. Kim, M.B. Prystowsky, D.W. Lancki, D.E. Sabath, J. Pan, and S.M. Weissman. 1987. Isolation and initial characterization of multiple species of T–lymphocyte subset cDNA clones. Proc.Natl.Acad.Sci.USA 84:2896, incorporated herein by reference and disclosed herein.

Kwon, B.S., and Weissman, S.M. 1989. cDNA Sequences of two inducible T–cell genes. Proc. Natl. Acad. Sci. USA 86:1963–1967.

Obaru, K., M. Fukuda, S. Maeda, and K. Shimada. 1986. A cDNA clone used to study mRNA induction in human tonsillar lymphocytes by a tumor promoter. J.Biochem. 99:885.

Maniatis et al, 1982) *Molecular Cloning: A Laboratory Manual* (Cold Spring Harbor Laboratory, Cold Spring Harbor, NY), pp. 310–352.

* cited by examiner

```
-145                                                                                       ATGTC
-140   CATGAACTGC TGAGTGGATA AACAGCACGG GATATCTCTG TCTAAAGGAA TATTACTACA CCAGGAAAAG
 -70   GACACATTCG ACAACAGGAA AGGAGCCTGT CACAGAAAAC CACAGTGTCC TGTGCATGTC ACATTTCGCC

1   ATG GGA AAC AAC TGT TAC AAC GTG GTG GTC ATT GTG CTG CTG CTA GTG GGC TGT GAG AAG   60
   1   Met Gly Asn Asn Cys Tyr Asn Val Val Val Ile Val Leu Leu Leu Val Gly Cys Glu Lys   20

61   GTG GGA GCC GTG CAG AAC TCC TGT GAT AAC TGT CAG CCT GGT ACT TTC TGC AGA AAA TAC  120
  21   Val Gly Ala Val Gln Asn Ser Cys Asp Asn Cys Gln Pro Gly Thr Phe Cys Arg Lys Tyr   40

121   AAT CCA GTC TGC AAG AGC TGC CCT CCA AGT ACC TTC TCC AGC ATA GGT GGA CAG CCG AAC  180
  41   Asn Pro Val Cys Lys Ser Cys Pro Pro Ser Thr Phe Ser Ser Ile Gly Gly Gln Pro Asn   60

181   TGT AAC ATC TGC AGA GTG TGT GCA GGC TAT TTC AGG TTC AAG AAG TTT TGC TCC TCT ACC  240
  61   Cys Asn Ile Cys Arg Val Cys Ala Gly Tyr Phe Arg Phe Lys Lys Phe Cys Ser Ser Thr   80

241   CAC AAC GCG GAG TGT GAG TGC ATT GAA GGA TTC CAT TGC TTG GGG CCA CAG TGC ACC AGA  300
  81   His Asn Ala Glu Cys Glu Cys Ile Glu Gly Phe His Cys Leu Gly Pro Gln Cys Thr Arg  100

301   TGT GAA AAG GAC TGC AGG CCT GGC CAG GAG CTA ACG AAG CAG GGT TGC AAA ACC TGT AGC  360
 101   Cys Glu Lys Asp Cys Arg Pro Gly Gln Glu Leu Thr Lys Gln Gly Cys Lys Thr Cys Ser  120

361   TTG GGA ACA TTT AAT GAC CAG AAC GGT ACT GGC GTC TGT CGA CCC TGG ACG AAC TGC TCT  420
 121   Leu Gly Thr Phe Asn Asp Gln Asn Gly Thr Gly Val Cys Arg Pro Trp Thr Asn Cys Ser  140

421   CTA GAC GGA AGG TCT GTG CTT AAG ACC GGG ACC ACG GAG AAG GAC GTG GTG TGT GGA CCC  480
 141   Leu Asp Gly Arg Ser Val Leu Lys Thr Gly Thr Thr Glu Lys Asp Val Val Cys Gly Pro  160

481   CCT GTG GTG AGC TTC TCT CCC AGT ACC ACC ATT TCT GTG ACT CCA GAG GGA GGA CCA GGA  540
 161   Pro Val Val Ser Phe Ser Pro Ser Thr Thr Ile Ser Val Thr Pro Glu Gly Gly Pro Gly  180

541   GGG CAC TCC TTG CAG GTC CTT ACC TTG TTC CTG GCG CTG ACA TCG GCT TTG CTG CTG GCC  600
 181   Gly His Ser Leu Gln Val Leu Thr Leu Phe Leu Ala Leu Thr Ser Ala Leu Leu Leu Ala  200

601   CTG ATC TTC ATT ACT CTC CTG TTC TCT GTG CTC AAA TGG ATC AGG AAA AAA TTC CCC CAC  660
 201   Leu Ile Phe Ile Thr Leu Leu Phe Ser Val Leu Lys Trp Ile Arg Lys Lys Phe Pro His  220

661   ATA TTC AAG CAA CCA TTT AAG AAG ACC ACT GGA GCA GCT CAA GAG GAA GAT GCT TGT AGC  720
 221   Ile Phe Lys Gln Pro Phe Lys Lys Thr Thr Gly Ala Ala Gln Glu Glu Asp Ala Cys Ser  240

721   TGC CGA TGT CCA CAG GAA GAA GAA GGA GGA GGA GGA GGC TAT GAG CTG TGA TGTACTATC    780
 241   Cys Arg Cys Pro Gln Glu Glu Glu Gly Gly Gly Gly Gly Tyr Glu Leu ---
```

FIG. 2A

```
 781   CTAGGAGATG TGTGGGCCGA AACCGAGAAG CACTAGGACC CCACCATCCT GTGGAACAGC ACAAGCAACC   850

851   CCACCACCCT GTTCTTACAC ATCATCCTAG ATGATGTGTG GGCGCGCACC TCATCCAAGT CTCTTCTAAC   920

921   GCTAACATAT TTGTCTTTAC CTTTTTTAAA TCTTTTTTTA AATTTAAATT TTATGTGTGT GAGTGTTTTG   990

991   CCTGCCTGTA TGCACACGTG TGTGTGTGTG TGTGTGTGAC ACTCCTGATG CCTGAGGAGG TCAGAAGAGA  1060

1061   AAGGCTTGGT TCCATAAGAA CTGGAGTTAT GGATGGCTGT GAGCCCGGnnn GATAGGTCGG GACGGAGACC  1130

1131   TGTCTTCTTA TTTTAACGTG ACTGTATAAT AAAAAAAAAA TGATATTTCG GAATTGTAG AGATTGTCCT  1200

1201   GACACCCTTC TAGTTAATGA TCTAAGAGGA ATTGTTGATA CGTAGTATAC TGTATATGTG TATGTATATG  1270

1271   TATATGTATA TATAAGACTC TTTTACTGTC AAAGTCAACC TAGAGTGTCT GGTTACCAGG TCAATTTTAT  1340

1341   TGGACATTTT ACGTCACACA CACACACACA CACACACACA CACGTTTATA CTACGTACTGT TATCGGTAT  1410

1411   TCTACGTCAT ATAATGGGAT AGGGTAAAAG GAAACCAAAG AGTGAGTGAT ATTATTGTGGA GGTGACAGA  1480

1481   CTACCCCTTC TGGGTACGTA GGGACAGACC TCCTTCGGAC TGTCTAAAAC TCCCCTTAGA AGTCTCGTCA  1550

1551   AGTTCCCGGA CGAAGAGGAC AGAGGAGACA CAGTCCGAAA AGTTATTTTT CCGGCAAATC CTTTCCCTGT  1620

1621   TTCGTGACAC TCCACCCCTT GTGGACACTT GAGTGTCATC CTTGCGCCGG AAGGTCAGGT GGTACCCGTC  1690

1691   TGTAGGGGCG GGGAGACAGA GCCGCGGGGG AGCTACGAGA ATCGACTCAC AGGGCGCCCC GGGCTTCGCA  1760

1761   AATGAAACTT TTTTAATCTC ACAAGTTTCG TCCGGGCTCG GCGGACCTAT GGCGTCGATC CTTATTACCT  1830

1831   TATCCTGGCG CCAAGATAAA ACAACCAAAA GCCTTGACTC CGGTACTAAT TCTCCCTGCC GGCCCCCGTA  1900

1901   AGCATAACGC GGCGATCTCC ACTTTAAGAA CCTGGCCGCG TTCTGCCTGG TCTCGCTTTC GTAAACGGTT  1970

1971   CTTACAAAAG TAATTAGTTC TTGCTTTCAG CCTCCAAGCT TCTGCTAGTC TATGGCAGCA TCAAGGCTGG  2040

2041   TATTTGCTAC GGCTGACCGC TACGCCGCCG CAATAAGGGT ACTGGGCGGC CCGTCGAAGG CCCTTTGGTT  2110

2111   TCAGAAACCC AAGGCCCCCC TCATACCAAC GTTTCGACTT TGATTCTTGC CGGTACGTGG TGGTGGGTGC  2180

2181   CTTAGCTCTT TCTCGATAGT TAG AC
```

FIG. 2B

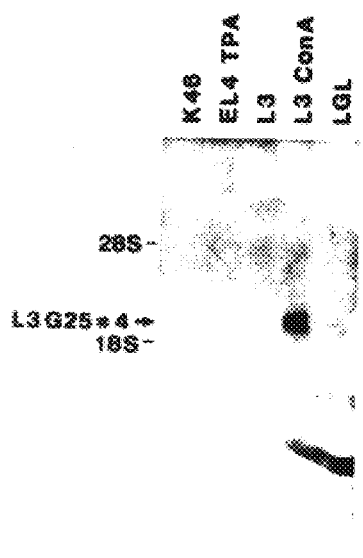  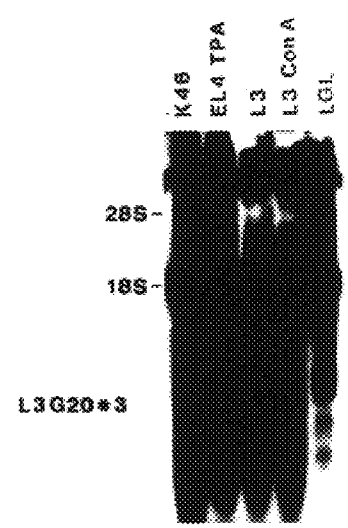
FIG. 3A    FIG. 3B    FIG. 3C
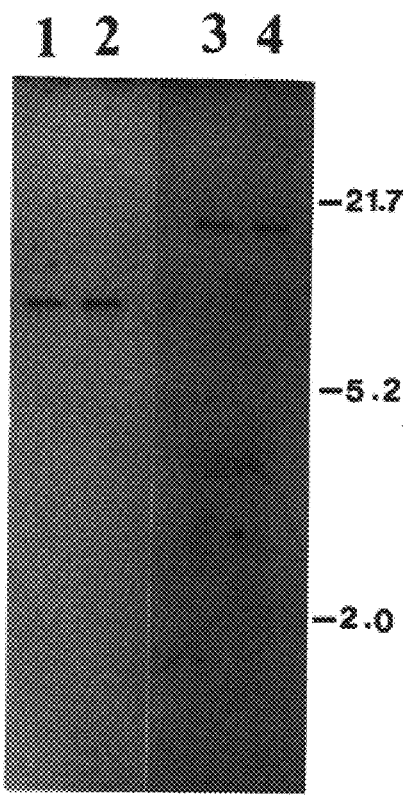
FIG. 4

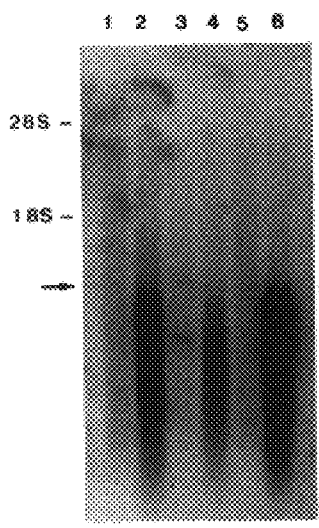 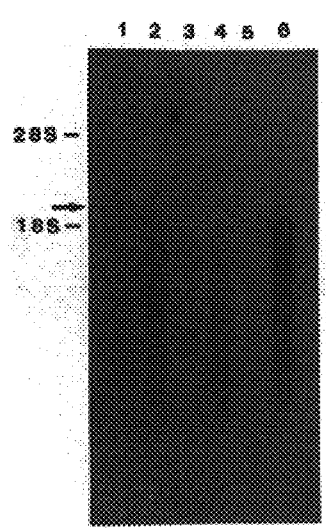 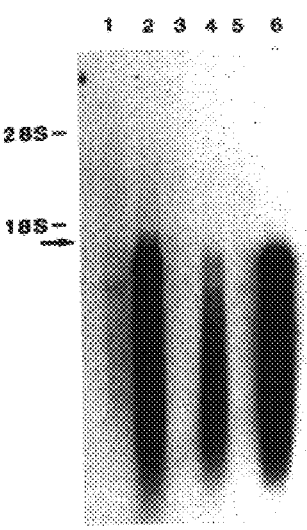
FIG. 7A    FIG. 7B    FIG. 7C
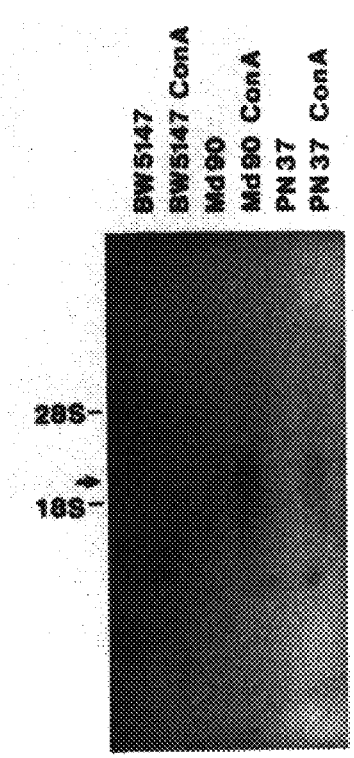 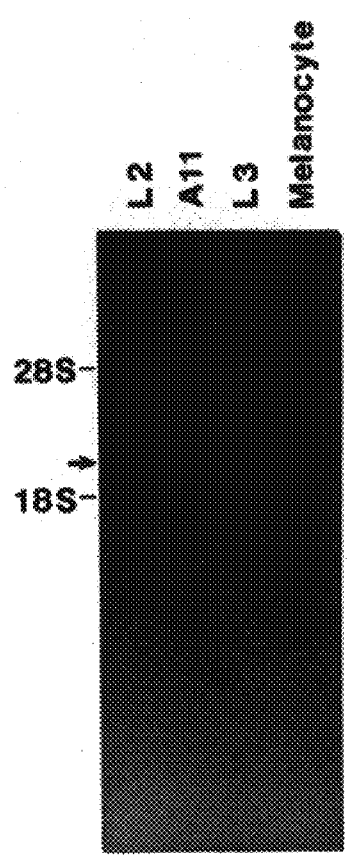
FIG. 8A    FIG. 8B

|        | | | | | | | | |
|---|---|---|---|---|---|---|---|---|
| 4-1BB | (64) | C R V C A G | Y | F | K K | F | C S S T H N | A | E C | E C |
| Sina  | (71) | C P V C F D | Y | V | · · | L Q C S S G H L | V | C C | V S | C |
| DG17  | (25) | C P I C F E F I | | Y K K Q I | Y Q C K S G H H | A | C K | E C |

FIG. 17

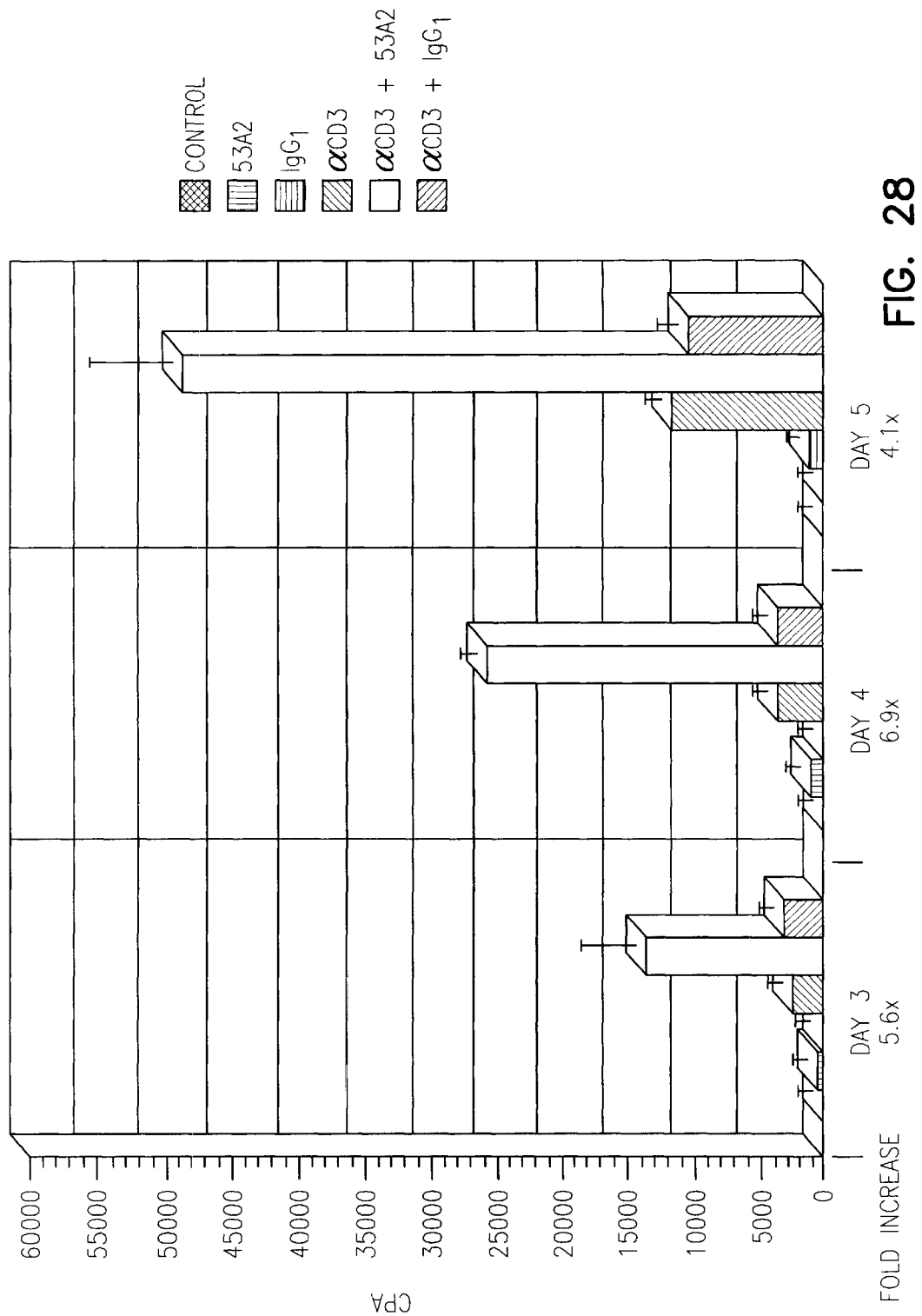

SEQUENCE LISTING

```
<160> NUMBER OF SEQ ID NOS: 13

<210> SEQ ID NO 1
<211> LENGTH: 2350
<212> TYPE: DNA
<213> ORGANISM: Mus musculus
<220> FEATURE:
<221> NAME/KEY: misc_feature
<222> LOCATION: (1)...(2350)
<223> OTHER INFORMATION: n = A,T,C or G

<400> SEQUENCE: 1
atgtccatga actgctgagt ggataaacag cacgggatat ctctgtctaa aggaatatta      60
ctacaccagg aaaaggacac attcgacaac aggaaaggag cctgtcacag aaaaccacag     120
tgtcctgtgc atgtgacatt tcgccatggg aaacaactgt tacaacgtgg tggtcattgt    180
gctgctgcta gtgggctgtg agaaggtggg agccgtgcag aactcctgtg ataactgtca    240
gcctggtact ttctgcagaa aatacaatcc agtctgcaag agctgccctc caagtacctt    300
ctccagcata ggtggacagc cgaactgtaa catctgcaga gtgtgtgcag gctatttcag    360
gttcaagaag ttttgctcct ctacccacaa cgcggagtgt gagtgcattg aaggattcca    420
ttgcttgggg ccacagtgca ccagatgtga aaaggactgc aggcctggcc aggagctaac    480
gaagcagggt tgcaaaacct gtagcttggg aacatttaat gaccagaacg gtactggcgt    540
ctgtcgaccc tggacgaact gctctctaga cggaaggtct gtgcttaaga ccgggaccac    600
ggagaaggac gtggtgtgtg gaccccctgt ggtgagcttc tctcccagta ccaccatttc    660
tgtgactcca gagggaggac caggagggca ctccttgcag gtccttacct tgttcctggc    720
gctgacatcg gctttgctgc tggccctgat cttcattact ctcctgttct ctgtgctcaa    780
atggatcagg aaaaaattcc cccacatatt caagcaacca tttaagaaga ccactggagc    840
agctcaagag gaagatgctt gtagctgccg atgtccacag gaagaagaag gaggaggagg    900
aggctatgag ctgtgatgta ctatcctagg agatgtgtgg gccgaaaccg agaagcacta    960
ggaccccacc atcctgtgga acagcacaag caacccccacc accctgttct tacacatcat   1020
cctagatgat gtgtgggcgc gcacctcatc caagtctctt ctaacgctaa catatttgtc   1080
tttacctttt ttaaatcttt ttttaaattt aaattttatg tgtgtgagtg ttttgcctgc   1140
```

```
ctgtatgcac acgtgtgtgt gtgtgtgtgt gtgacactcc tgatgcctga ggaggtcaga    1200
agagaaaggg ttggttccat aagaactgga gttatggatg gctgtgagcc ggnnngatag    1260
gtcgggacgg agacctgtct tcttatttta acgtgactgt ataataaaaa aaaaatgata    1320
tttcgggaat tgtagagatt ctcctgacac ccttctagtt aatgatctaa gaggaattgt    1380
tgatacgtag tatactgtat atgtgtatgt atatgtatat gtatatataa gactctttta    1440
ctgtcaaagt caacctagag tgtctggtta ccaggtcaat tttattggac attttacgtc    1500
acacacacac acacacacac acacacacgt ttatactacg tactgttatc ggtattctac    1560
gtcatataat gggatagggt aaaggaaac caaagagtga gtgatattat tgtggaggtg     1620
acagactacc ccttctgggt acgtagggac agacctcctt cggactgtct aaaactcccc    1680
ttagaagtct cgtcaagttc ccggacgaag aggacagagg agacacagtc cgaaaagtta    1740
tttttccggc aaatcctttc cctgtttcgt gacactccac cccttgtgga cacttgagtg    1800
tcatccttgc gccggaaggt caggtggtac ccgtctgtag gggcggggag acagagccgc    1860
gggggagcta cgagaatcga ctcacagggc ccccgggct tcgcaaatga aactttttta    1920
atctcacaag tttcgtccgg gctcggcgga cctatggcgt cgatccttat taccttatcc    1980
tggcgccaag ataaaacaac caaaagcctt gactccggta ctaattctcc ctgccggccc    2040
ccgtaagcat aacgcggcga tctccacttt aagaacctgg ccgcgttctg cctggtctcg    2100
ctttcgtaaa cggttcttac aaaagtaatt agttcttgct ttcagcctcc aagcttctgc    2160
tagtctatgg cagcatcaag gctggtattt gctacggctg accgctacgc cgccgcaata    2220
agggtactgg gcggcccgtc gaaggcccctt tggtttcaga aacccaaggc ccccctcata    2280
ccaacgtttc gactttgatt cttgccggta cgtggtggtg ggtgccttag ctctttctcg    2340
atagttagac                                                           2350
```

<210> SEQ ID NO 2
<211> LENGTH: 256
<212> TYPE: PRT
<213> ORGANISM: Mus musculus

<400> SEQUENCE: 2

```
Met Gly Asn Asn Cys Tyr Asn Val Val Ile Val Leu Leu Leu Val
  1               5                  10                  15

Gly Cys Glu Lys Val Gly Ala Val Gln Asn Ser Cys Asp Asn Cys Gln
             20                  25                  30

Pro Gly Thr Phe Cys Arg Lys Tyr Asn Pro Val Cys Lys Ser Cys Pro
         35                  40                  45

Pro Ser Thr Phe Ser Ser Ile Gly Gly Gln Pro Asn Cys Asn Ile Cys
     50                  55                  60

Arg Val Cys Ala Gly Tyr Phe Arg Phe Lys Lys Phe Cys Ser Ser Thr
 65                  70                  75                  80

His Asn Ala Glu Cys Glu Cys Ile Glu Gly Phe His Cys Leu Gly Pro
                 85                  90                  95

Gln Cys Thr Arg Cys Glu Lys Asp Cys Arg Pro Gly Gln Glu Leu Thr
            100                 105                 110

Lys Gln Gly Cys Lys Thr Cys Ser Leu Gly Thr Phe Asn Asp Gln Asn
        115                 120                 125

Gly Thr Gly Val Cys Arg Pro Trp Thr Asn Cys Ser Leu Asp Gly Arg
    130                 135                 140

Ser Val Leu Lys Thr Gly Thr Thr Glu Lys Asp Val Val Cys Gly Pro
145                 150                 155                 160
```

```
Pro Val Val Ser Phe Ser Pro Ser Thr Thr Ile Ser Val Thr Pro Glu
                165                 170                 175

Gly Gly Pro Gly Gly His Ser Leu Gln Val Leu Thr Leu Phe Leu Ala
            180                 185                 190

Leu Thr Ser Ala Leu Leu Leu Ala Leu Ile Phe Ile Thr Leu Leu Phe
        195                 200                 205

Ser Val Leu Lys Trp Ile Arg Lys Lys Phe Pro His Ile Phe Lys Gln
    210                 215                 220

Pro Phe Lys Lys Thr Thr Gly Ala Ala Gln Glu Glu Asp Ala Cys Ser
225                 230                 235                 240

Cys Arg Cys Pro Gln Glu Glu Glu Gly Gly Gly Gly Tyr Glu Leu
                245                 250                 255

<210> SEQ ID NO 3
<211> LENGTH: 24
<212> TYPE: PRT
<213> ORGANISM: Mus musculus

<400> SEQUENCE: 3

Cys Arg Val Cys Ala Gly Tyr Phe Arg Phe Lys Lys Phe Cys Ser Ser
1               5                   10                  15

Thr His Asn Ala Glu Cys Glu Cys
            20

<210> SEQ ID NO 4
<211> LENGTH: 22
<212> TYPE: PRT
<213> ORGANISM: Drosophila

<400> SEQUENCE: 4

Cys Pro Val Cys Phe Asp Tyr Val Ile Leu Gln Cys Ser Ser Gly His
1               5                   10                  15

Leu Val Cys Val Ser Cys
            20

<210> SEQ ID NO 5
<211> LENGTH: 26
<212> TYPE: PRT
<213> ORGANISM: Dictyostelium

<400> SEQUENCE: 5

Cys Pro Ile Cys Phe Glu Phe Ile Tyr Lys Lys Gln Ile Tyr Gln Cys
1               5                   10                  15

Lys Ser Gly His His Ala Cys Lys Glu Cys
            20                  25

<210> SEQ ID NO 6
<211> LENGTH: 6
<212> TYPE: PRT
<213> ORGANISM: Mus musculus
<220> FEATURE:
<221> NAME/KEY: SITE
<222> LOCATION: (1)...(6)
<223> OTHER INFORMATION: Xaa = Any Amino Acid

<400> SEQUENCE: 6

Val Gln Asn Ser Xaa Asp
1               5

<210> SEQ ID NO 7
<211> LENGTH: 12
```

```
<212> TYPE: PRT
<213> ORGANISM: Artificial Sequence
<220> FEATURE:
<223> OTHER INFORMATION: An artificial peptide

<400> SEQUENCE: 7

Cys Arg Pro Gly Gln Glu Leu Thr Lys Ser Gly Tyr
 1               5                  10

<210> SEQ ID NO 8
<211> LENGTH: 24
<212> TYPE: PRT
<213> ORGANISM: Artificial Sequence
<220> FEATURE:
<223> OTHER INFORMATION: A conserved pattern
<221> NAME/KEY: SITE
<222> LOCATION: (1)...(24)
<223> OTHER INFORMATION: Xaa = Any Amino Acid

<400> SEQUENCE: 8

Cys Xaa Xaa Cys Xaa Xaa Xaa Xaa Xaa Xaa Xaa Xaa Cys Xaa Xaa
 1               5                  10                  15

Xaa His Xaa Xaa Xaa Cys Xaa Cys
            20

<210> SEQ ID NO 9
<211> LENGTH: 4
<212> TYPE: PRT
<213> ORGANISM: Mus musculus

<400> SEQUENCE: 9

Cys Arg Cys Pro
 1

<210> SEQ ID NO 10
<211> LENGTH: 4
<212> TYPE: PRT
<213> ORGANISM: Artificial Sequence
<220> FEATURE:
<223> OTHER INFORMATION: A consensus sequence
<221> NAME/KEY: SITE
<222> LOCATION: (1)...(4)
<223> OTHER INFORMATION: Xaa = Any Amino Acid

<400> SEQUENCE: 10

Cys Xaa Cys Pro
 1

<210> SEQ ID NO 11
<211> LENGTH: 25
<212> TYPE: DNA
<213> ORGANISM: Artificial Sequence
<220> FEATURE:
<223> OTHER INFORMATION: A primer

<400> SEQUENCE: 11
acctcgaggt cctgtgcatg tgaca                                          25

<210> SEQ ID NO 12
<211> LENGTH: 25
<212> TYPE: DNA
<213> ORGANISM: Artificial Sequence
<220> FEATURE:
<223> OTHER INFORMATION: A primer

<400> SEQUENCE: 12
atgaattctt actgcaggag tgccc                                          25
```

```
<210> SEQ ID NO 13
<211> LENGTH: 11
<212> TYPE: PRT
<213> ORGANISM: Mus musculus

<400> SEQUENCE: 13

Cys Arg Pro Gly Gln Glu Leu Thr Lys Gln Gly
 1               5                  10
```

MURINE 4-1BB GENE

This application is a continuation-in-part of application Ser. No. 07/922,996, which is a continuation-in-part of application Ser. No. 07/267,577 filed Nov. 7, 1988 now abandoned.

The subject matter described herein was in part a subject invention of NIH Grants Nos. IR23AI23058-03, RO1 AI28175 and P60 KD20542 of which the present inventor was the Principal Investigator and either the Donald Guthrie Foundation for Medical Research Inc. of Guthrie Square, Sayre, Pa. 18849-1669 or Indiana University School of Medicine of Indianapolis, Ind. 46202, was the Grantee.

FIELD OF THE PRESENT INVENTION

The present invention relates to a previously unknown receptor protein which were isolated and identified based on specific expression of the T cell genes using a technique identified by the present inventor in a publication (Proc. Natl. Acad. Sci. USA. 84, 2896–2900, May 1987, Immunology), and more particularly relates to the receptor protein, 4-1BB, a monclonal antibody against 4-1BB, a ligand protein for detecting the presence of 4-1BB binding sites on cells and methods of using these proteins and antibody.

BACKGROUND OF THE PRESENT INVENTION

Lymphokines are the proteins by which the immune cells communicate with each other. Scientists produce them in sufficient quantities for therapeutic use against immunologic diseases. The immune system of humans and other species requires that white blood cells be made in the bone marrow, which white blood cells include phagocytes, lymphocytes and B cells. As presently understood, the phagocytes include macrophage cells which scavenge unwanted materials such as virus protein from the system. The lymphocytes include helper T cells and killer T cells and B cells as well as other cells, including those categorized as suppressor T cells.

The B cells produce the antibodies. The killer T cells physically pierce the cell and the helper T cells facilitate the whole process. In any event, the immune process is facilitated by lymphokines. Interleukin 1, secreted from macrophages activate the helper T cells and raise the body temperature causing fever which enhances the activity of the immune cells. The activated helper T Cells produce Interleukin 2 and Interleukin stimulates the helper and killer T cells to grow and divide. The helper T cells also produce another lymphokine, B cell growth factor (BCGF), which causes B cells to multiply. As the number of B cells increases, the helper T cells produce another lymphokine known as the B cell differentiating factor (BCDF), which instructs some of the B cells to stop replicating and start producing antibodies. T cells also produce a lymphokine, gamma interferon (IF), which has multiple effects like Interleukin 2. Interferon helps activate killer T cells, enabling them to attack the invading organisms. Like BCGF, interferon increases the ability of the B cells to produce antibodies. Interferon also affects the macrophages to keep them at the site of the infection and help the macrophages to digest the cells they have engulfed. Gathering momentum with each kind of lymphokine signal between the macrophages and the T cells, the lymphokines amplify the immune system response and the virus protein or other foreign matter on the infected cells is overwhelmed. There are many other lymphokines, maybe a hundred or more, which participate in the immune process. Many lymphokines are known and many are not.

Lymphokines are sometimes called intercellar peptide signals. Among scientists there is widespread use of cloned cell lines as lymphokine producers and the isolation of lymphokine mRNA has become a common technique. The present invention relates to a previously unknown receptor protein which was isolated and identified based on specific expression of the T cell genes using a technique identified by the present inventor in a publication (Proc. Natl. Acad. Sci. USA. 84, 2896–2900, May 1987, Immunology). The protocol reported in this publication can be used by scientists to detect virtually all of the lymphokines because the method is designed to detect virtually all the mRNA expressed differentially and the mRNA sequences of the immune cells are expressed differentially as they relate to the T cells and the killer T cells even though the level of expression is low and the quantity of the secreted lymphokine protein is low. The present inventor believes that the analysis described in the above identified publication can reveal biologically important molecules such as lymphokines because there are many indications that biologically important or active molecules are coded by the most scarce messages. An example is a transforming growth factor (TGF) which is present as only one of a million clones. There are many known lymphokine proteins and they include the interferons, interleukin-1,2,3,4,5,6,7, colony-stimulating factors, lymphotoxin, tumor necrosis factor and erythropoietin, as well as others.

Most T cell factors have been classically identified by recognizing biologic activities in assays, purifying the protein information. An alternative approach is to isolate putative T cell genes based upon specific expression and then demonstrate the function of the unknown molecule. Using the aforesaid modified differential screening procedure, the present inventor has recently cloned a series of T cell subset-specific cDNAs from cloned helper T (HTL) L2 and cloned cytolytic T lymphocyte (CTL) L3.

A series of T-cell subset-specific cDNAs were isolated from cloned murine T-cells by employing a modified differential screening procedure (88, 89). The nucleotide sequence and expression properties of some of the cDNA species have been reported (90). One of the genes not previously characterized, 4-1BB, was studied further. Apparent full length cDNAs corresponding to fourteen species of the 16 initial isolates were sequenced and were found to constitute five different species. Three of the five were identical to previously reported cDNA sequences of proenkephalin, T cell replacing factor and HF gene (a serine esterase). The other two, represented as L2G25B and 4-1BB, were novel sequences of unknown function. The open reading frames of 4-1BB and L2G25B code for 245 and 92 amino acids, respectively. The predicted proteins of 4-1BB and L2G25B include 22 and 23 amino acid-long putative signal sequences, respectively. The protein backbones of mature proteins encoded by 4-1BB and L2G25B are composed of 234 amino acids with molecular weight of 25000 and 69 amino acids with molecular weight of 7880, respectively. 4-1BB contains two potential N-glycosylation sites while L2G25B has none. 4-1BB contains 23 cysteine residues in the putative mature protein.

The cDNA L2G25B encodes for the lymphokine, macrophage inflammatory protein-1α or MIP-1α. MIP-1α has been described in a paper entitled, "Enhancing and Suppressing Effects of Recombinant Murine Macrophage Inflammatory Proteins on Colony Formation In Vitro by Bone Marrow Myeloid Progenitor Cells", Hal E. Broxmeyer, Barbara Sherry, Li Lu, Scott Cooper, Kwi-Ok Oh, Patricia Tekamp-Olson, Byoung S. Kwon, and Anthony Cerami, Blood 76, 111–1116, 1990 and is incorporated herein by reference. This was the first time the suppressing activity of MIP-1α was characterized.

The cDNA clone, called 4-1BB, was originally believed to be a lymphokine based upon the early experiments disclosed herein. The later studies showed that 4-1BB is an inducible receptor-like sequence found in both cytolytic and helper T-cells. Chalupny and colleagues (132) published a paper disclosing a fusion protein consisting of the extracellular domain of 4-1BB and the Fc region of IgG$_1$. Chalupny et al. taught that the highest levels of 4-1BB Rg (4-1BB-immunoglobulin fusion protein) binding was to human vitronectin. The present inventor performed an ELISA study using 4-1BB-AP (the fusion protein of the present invention) and human vitronectic. No binding of 4-1BB-AP based on alkaline phoshatase activity was observed. To rule out the possibility that 4-1BB-AP was binding to proteins extrinsically attached to the cell surface, B-Cell lymphomas were washed in acid conditions prior to the binding assay; 4-1BB-AP still bound specifically to mature B-cell lymphomas. Based on the data reported by Chalupny et al. it does not appear that they teach a fusion protein capable of accurately identifying 4-1BB ligands.

SUMMARY OF THE PRESENT INVENTION

The present invention includes the receptor protein 4-1BB and the cDNA gene encoding for receptor protein 4-1BB. the nucleotide sequence of the isolated cDNA is disclosed herein along with the deduced amino acid sequence. The cDNA gene identified as p4-1BB was deposited at the American Type Culture Collection at 12301 Parklawn Drive, Rockville, Md. 20852 under ATCC No.: 67825. The cDNA, and fragments and derivatives thereof, can be used as a probe to isolate DNA sequences encoding for proteins similar to the receptor protein encoded by the cDNA. Namely, the cDNA of a human receptor corresponding to the mouse cDNA 4-1BB can be isolated from a human source using cDNA 4-1BB as a probe.

The receptor protein 4-1BB can be produced by: 1) inserting the cDNA of 4-1BB into an appropriate expression vector, 2) transfecting the expression vector into an appropriate transfection host, c) growing the transfected hosts in appropriate culture media and d) purifying the receptor protein from the culture media. The protein and fragments and derivatives can be used: 1) as a probe to isolate ligands to receptor protein 4-1BB, 2) to stimulate proliferation of B-cell's expressing 4-1BB ligands, or 3) to block 4-1BB ligand binding. B-cells that have expressed a ligand to receptor protein 4-1BB are treated with cells that have expressed receptor protein 4-1BB and B-cell proliferation is induced. The use of 4-1BB to block 4-1BB ligand binding has practical application in the suppression of the immune system during organ transplantation. A similar costimulatory immune system pathway is being analyzed for this type of application. See "Mounting a Targeted Strike on Unwanted Immune Responses", Jon Cohen, Science, Vol. 257, 8-7-92; "Long Term Survival of Xenogeneic Pancreatic Islet Grafts Induced by CTLA4Ig", Lenschow et al, Science Vol. 257, 7-8-92; and "Immunosuppresion in Vivo by a Soluble Form of the CTLA-4 T Cell Activation Molecule", Linsley et al, Science Vol. 257 7-8-92.

A monoclonal antibody against 4-1BB was developed which specifically recognizes an epitope on the extracellular domain of receptor protein 4-1BB. The monoclonal antibody is produced from a hybridoma identified as 53A2 and deposited at the American Type Culture Collection at 12301 Parklawn Drive, Rockville, Md. 20852 under ATCC No.: HB-11248. The monoclonal antibody can be used to enhance T-cell proliferation by treating T-cells that have expressed receptor protein 4-1BB with antiCD3 monoclonal antibody.

Some tumors are potentially immunogenic but do not stimulate an effective anti-immune response in vivo. Tumors may be capable of delivering antigen-specific signals to T cells, but may not deliver the co-stimulatory signals necessary for full activation of T cells. Expression of the co-stimulatory ligand on B7 of melanoma cells was found to induce the rejection of a murine melanoma in vivo. ("Tumor Rejection After Direct Co-Stimulation of CD8$^+$ T Cells by B7-Transfected Melanoma Cells", Sarah E. Townsend and James P. Allison, Science Vol. 259, 1-5-93.). The monoclonal antibody of the present invention may be capable of the same effect as it is now known to enduce T cell proliferation and activation.

A fusion protein for detecting cell membrane ligands to receptor protein 4-1BB was developed. It comprises the extracellular portion of the receptor protein 4-1BB and a detection protein bound to the portion of the receptor protein 4-1BB. The portion of the receptor protein 4-1BB binds to the cell membrane ligands and binding can be detected by relative activity assays for the detection protein. The fusion protein is placed in the presence of a cell suspected to express the receptor protein 4-1BB. Then the cell is washed of any fusion protein not bound to the cell membrane ligands. Once the washed cells are placed in the presence of a substrate for the detection protein and the relative activity of the detection protein can be measured. The detection protein disclosed herein is alkaline phosphatase.

The primary object is to provide the teachings identifying the new receptor, 4-1BB as identified herein by its sequence.

Another object of the present invention is to provide teachings of how the new receptor may be used to isolate and identify corresponding molecules in related species.

Still another object of the teachings of the present invention is to teach the identification of the new receptor as reported herein.

Still another object of the teachings of the present invention is to teach the anti-4-1BB monoclonal antibody produced from the hybridoma 53A2 as reported herein.

Still another object of the teachings of the present invention is to teach a fusion protein comprising the extracellular portion of 4-1BB and a detection protein.

Still another object of the teachings of the present invention is to teach methods of using the cDNA 4-1BB, the receptor protein 4-1BB, the monoclonal antibody and the fusion protein.

BRIEF DESCRIPTIONS OF THE FIGURES

FIGS. 2a and 2b show the nucleotide sequence (SEQ ID NO:1) and the deduced amino acid sequence (SEQ ID NO:2) of mouse receptor 4-1BB.

FIGS. 3a, 3b, and 3c show an RNA blot analysis of ConA-stimulated L3 RNA with the expression being for different sizes of receptor 4-1BB mRNA.

FIG. 4 shows a Southern Blot analysis of mouse genomic DNA for fragments of L2G25B and 4-1BB cDNA.

Figure 5A:
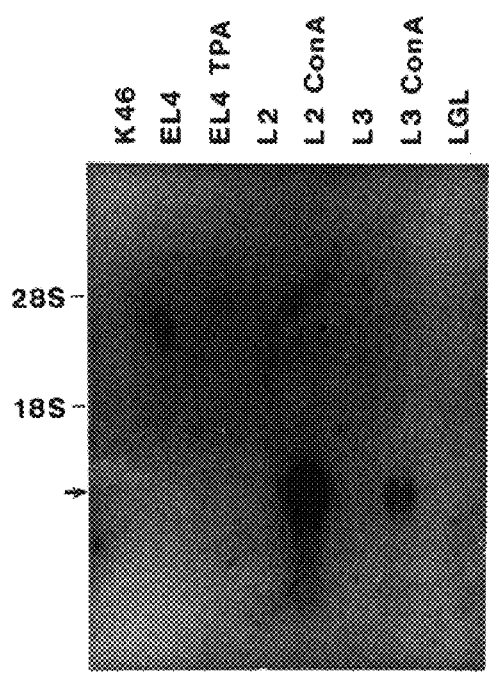
Figure 5B:
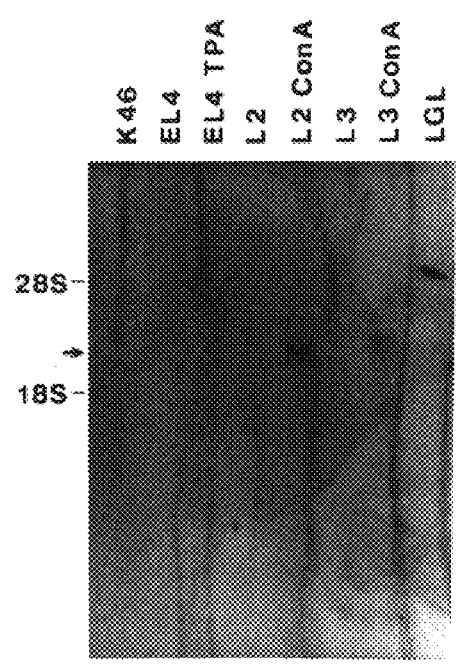

FIGS. 5a and 5b show L2G25B and 4-1BB expressed preferentially in L2 and L3 cells only after concanavalin A stimulation.

FIGS. 6a, 6b, 6c and 6d show RNA Blot patterns of lymphokine L2G25B and receptor 4-1BB in mRNA expression TCR stimulation or Il-2 treatment.

FIGS. 7a, 7b and 7c show expression of lymphokine L2G25B mRNA and receptor 4-1BB mRNA in a HTL L2 and a CTL dB45 cells.

FIGS. 8a and 8b show the expression of receptor 4-1BB mRNA in concanavalin A-stimulated hybridomas PN37 and Md90 and in a unstimulated CTL CTLLA11.

FIGS. 9a, 9b, 9c and 9d show the effect of cyclosporin A on L2G25B and 4-1BB mRNA expression.

Figure 10A:
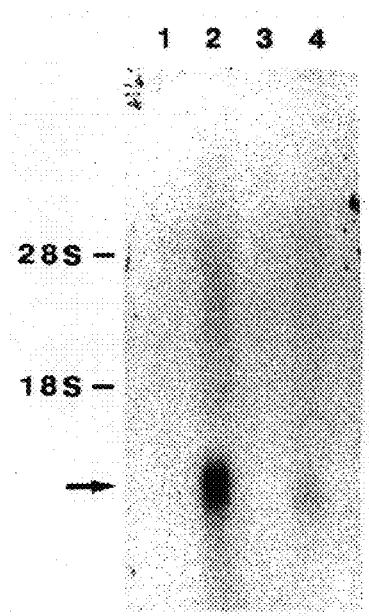
Figure 10B:
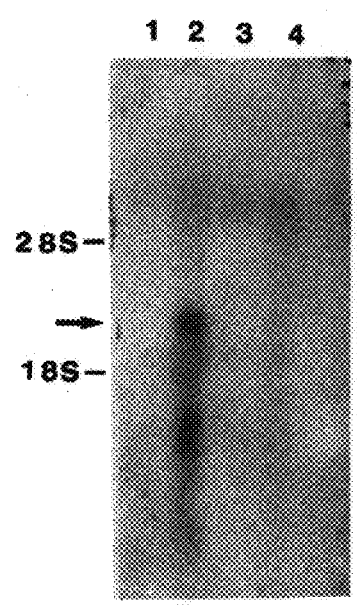
Figure 10C:
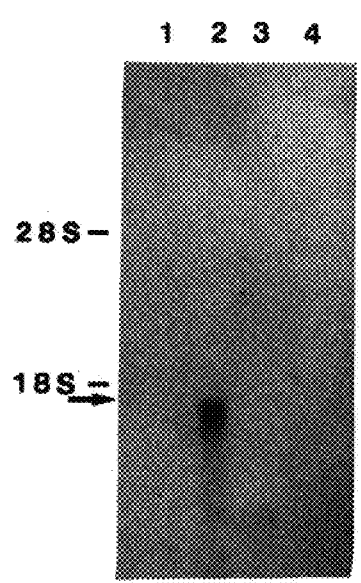

FIGS. 10a, 10b and 10c shows the expression of lymphokine L2G25B and receptor 4-1BB mRNA in mouse splenocytes.

Figure 11:
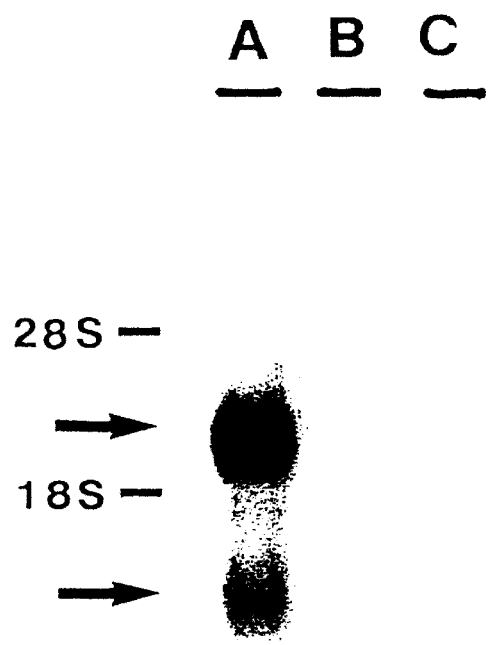

FIG. 11 shows the expression of 4-1BB on RNA in CTLL-R8.

Figure 12:
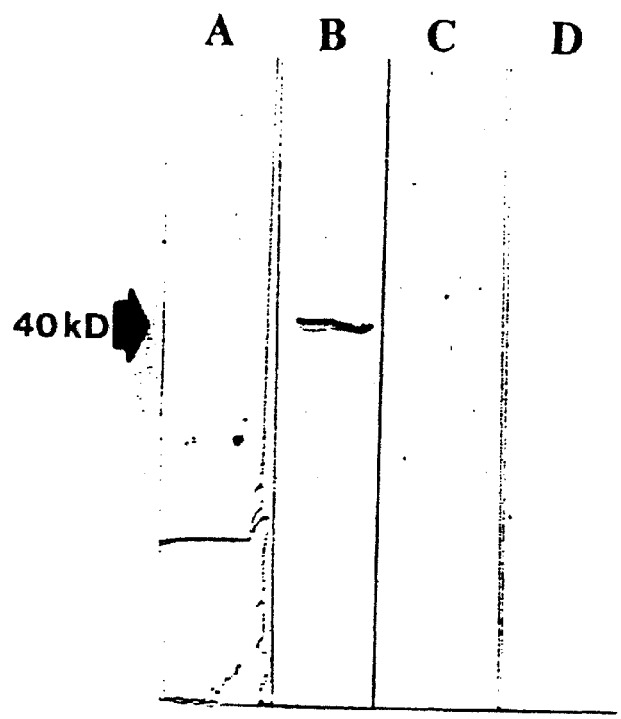

FIG. 12 shows an immunoblot analysis of CTLL-R8 cell lysates with anti-4-1BB-0 serum.

Figure 13:
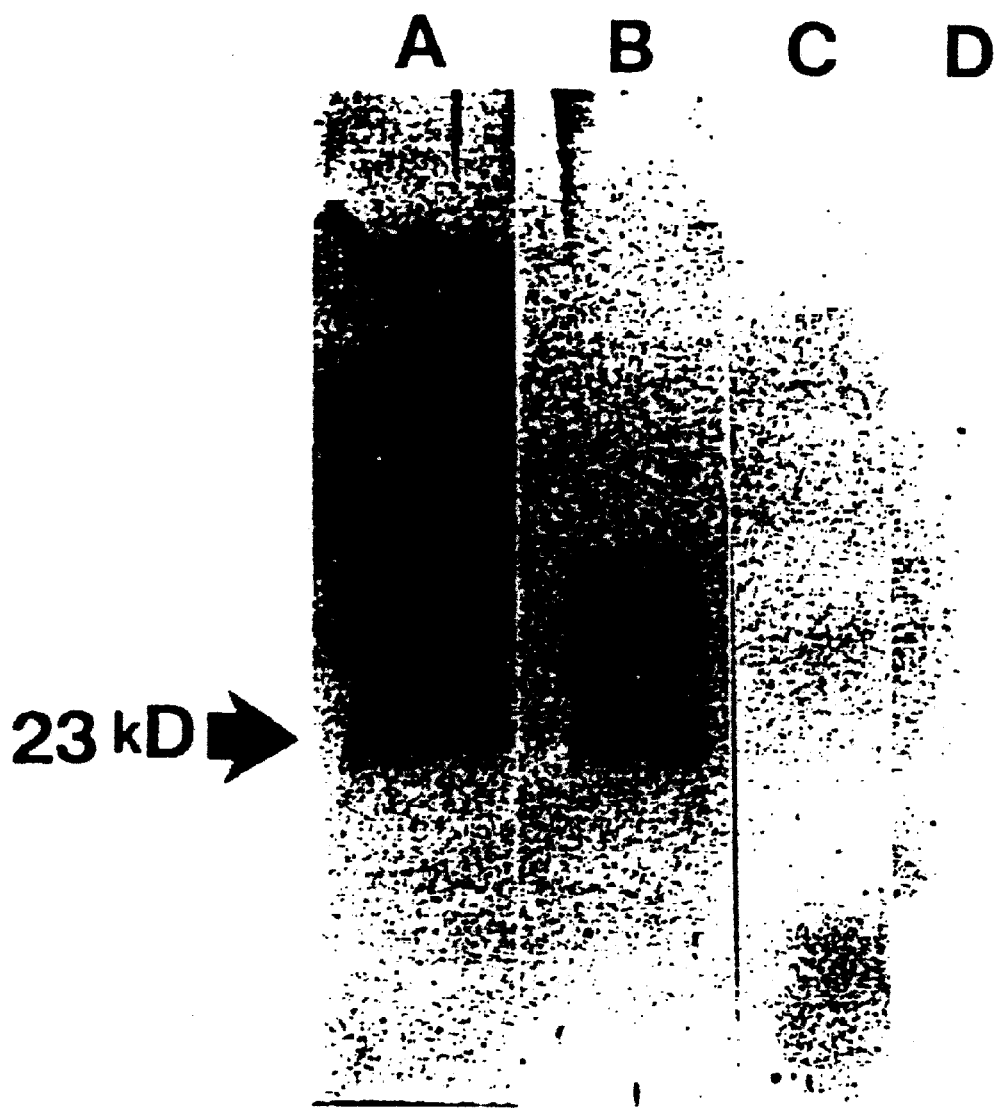

FIG. 13 shows an immunoblot analysis of the 4-1BBPs.

FIG. 14 shows representative histograms of IgG fraction of anti-4-1BB-O related fluorescence intensity of CTLL-R8 cells.

Figure 15:
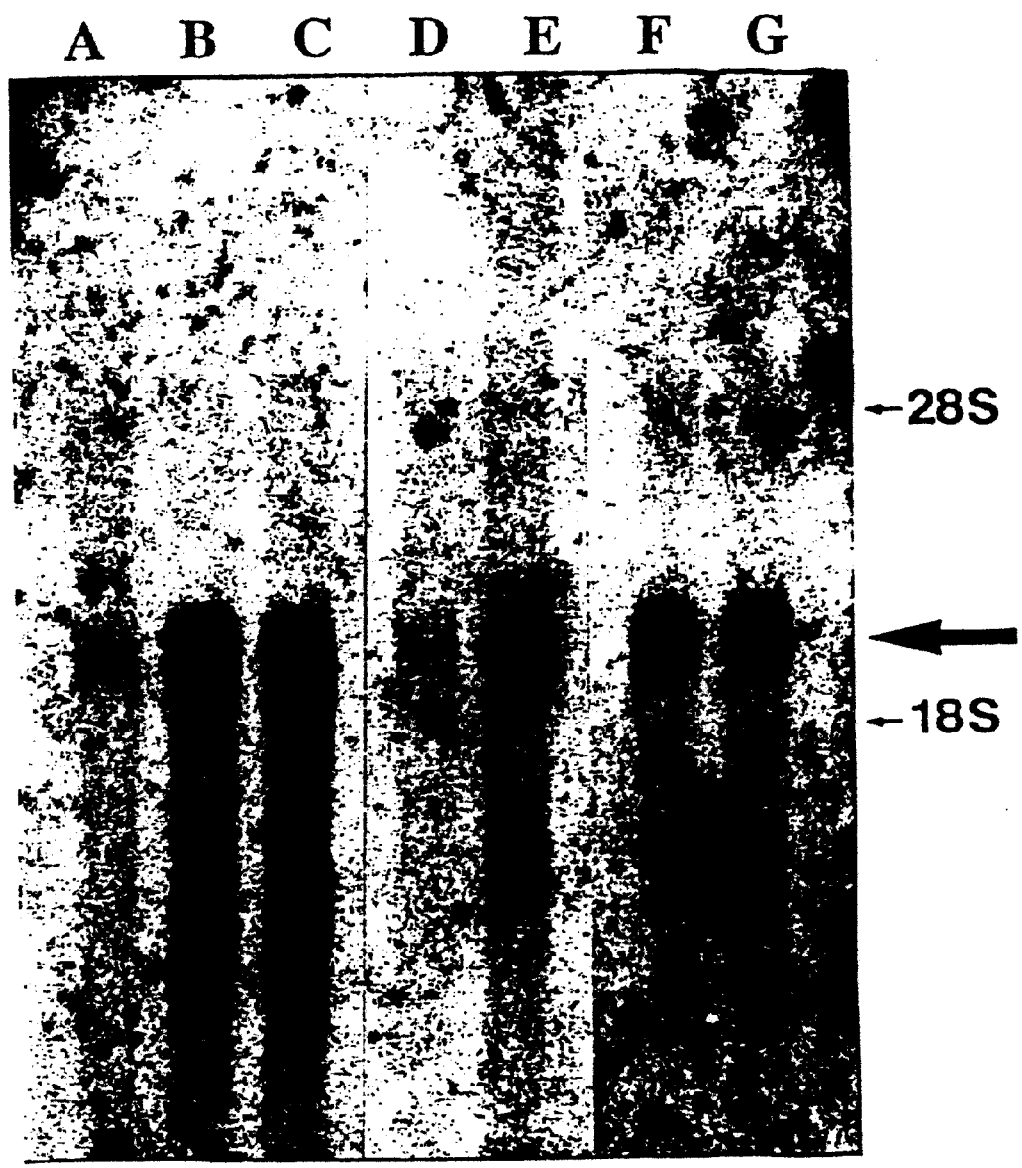

FIG. 15 shows the expression of 4-1BB RNA in mouse tissues.

Figure 16:
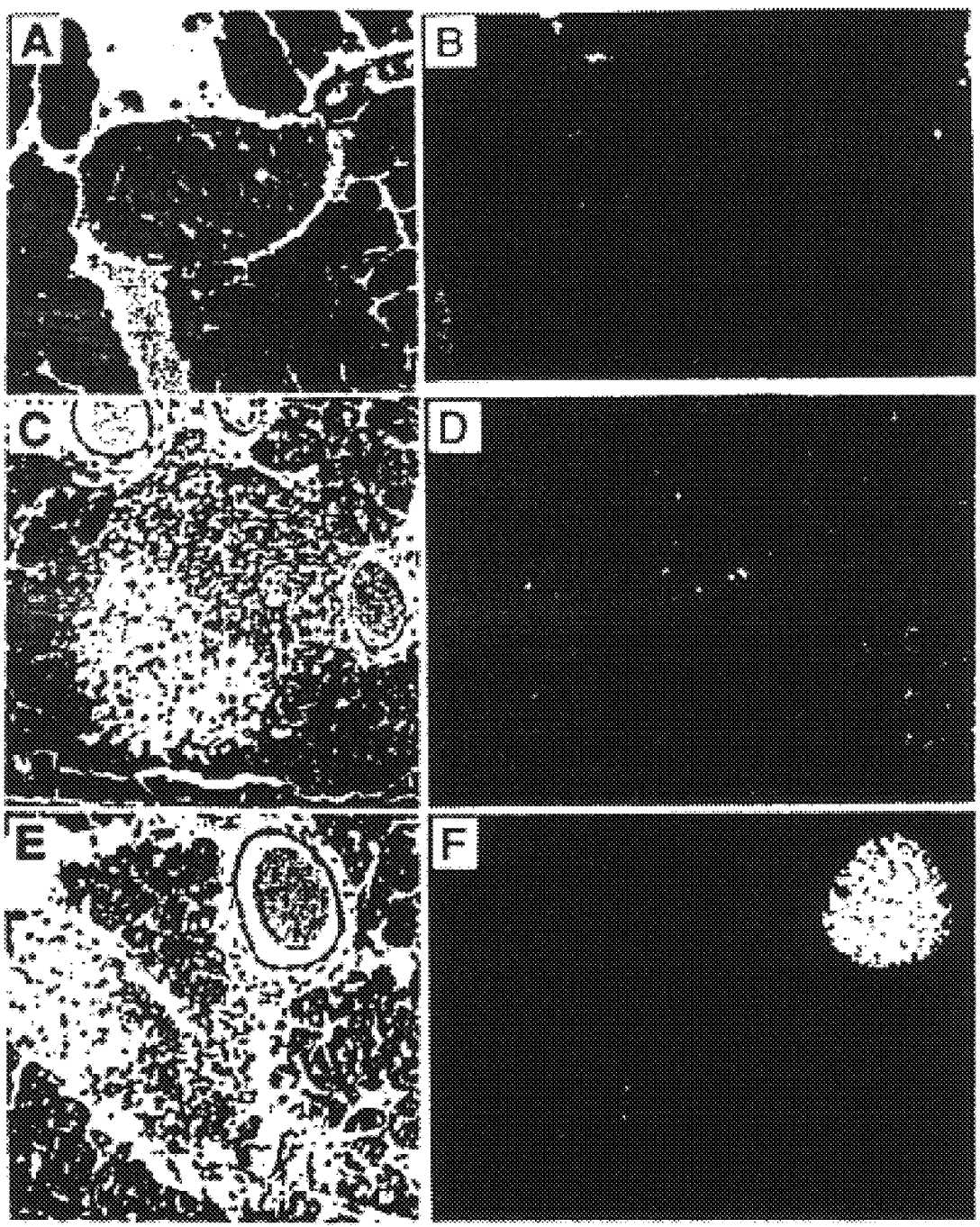

FIG. 16 shows the histology of NOD mouse pancreata and immunofluorescent staining of islets showing different stages of insulitis.

FIG. 17 shows a comparison of the 4-1BBP amino acid sequence (SEQ ID NO:3) with the amino acid sequence in sina (SEQ ID NO:4) Drosophila and DG17 (SEQ ID NO:5) of Dictyostelium.

Figure 18:
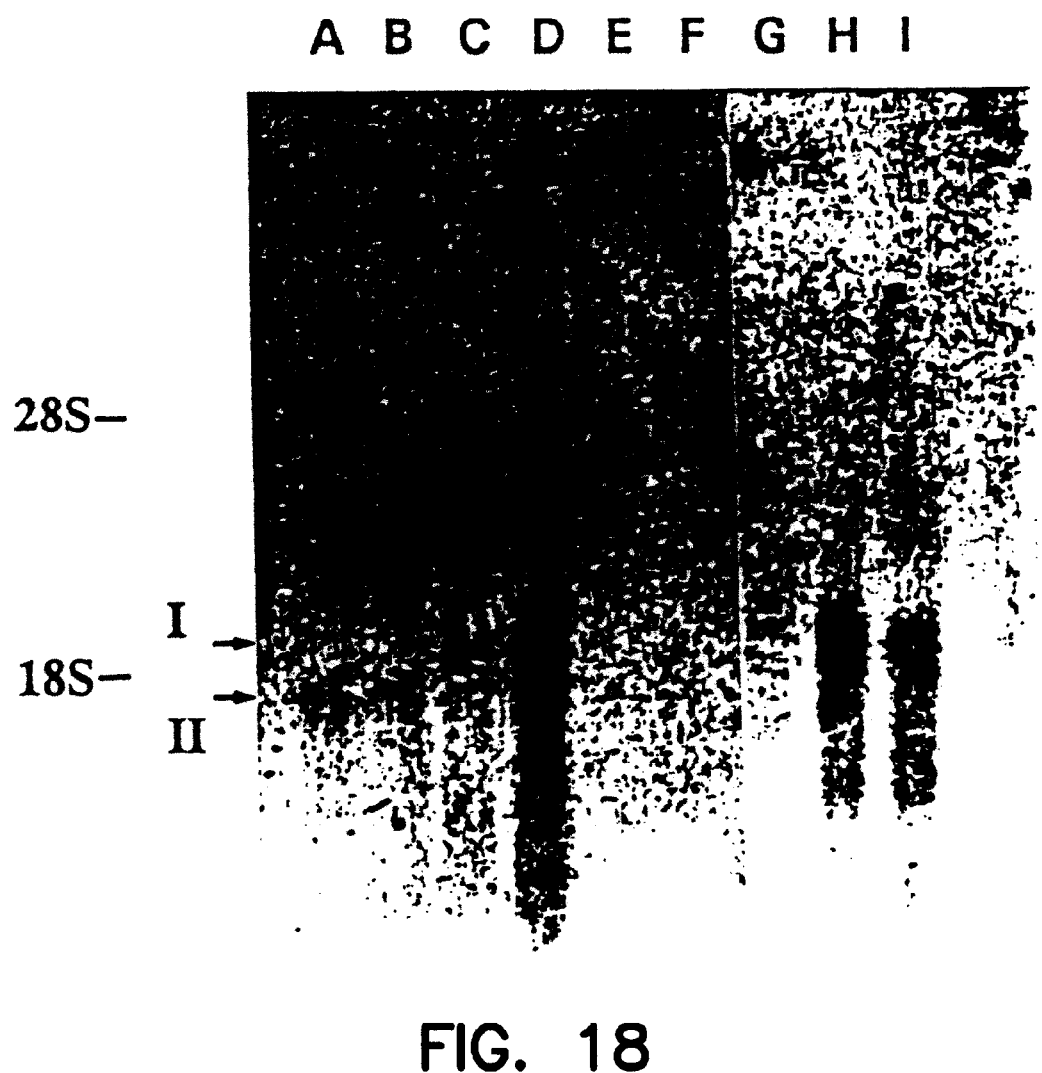

FIG. 18 shows a northern blot analysis of kidney and brain RNA.

Figure 19:
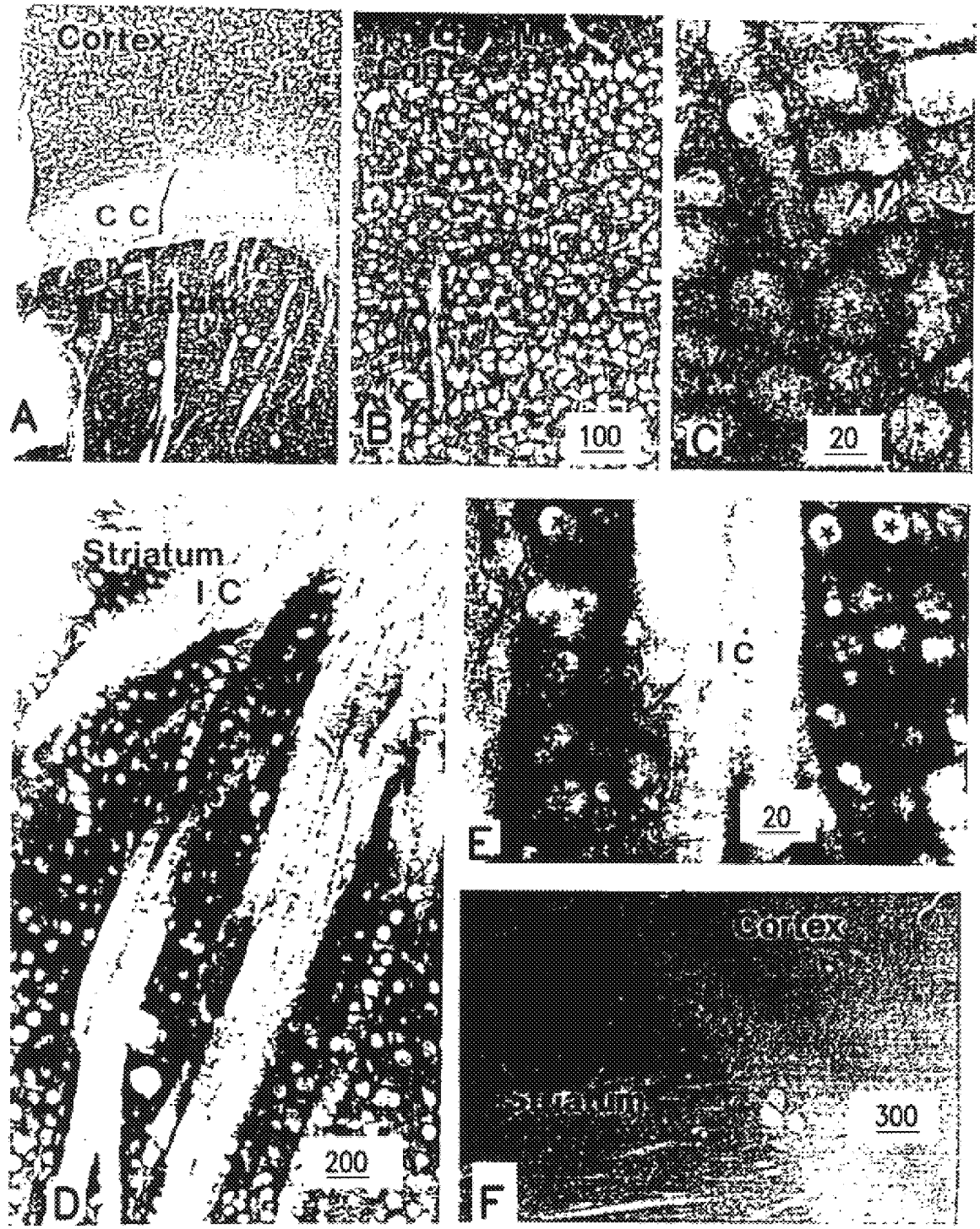

FIG. 19 shows 4-1BB immunostaining in the cortex (a,b, and d) striatum (a,d, and e) at progressively enlarged magnifications.

Figure 20:
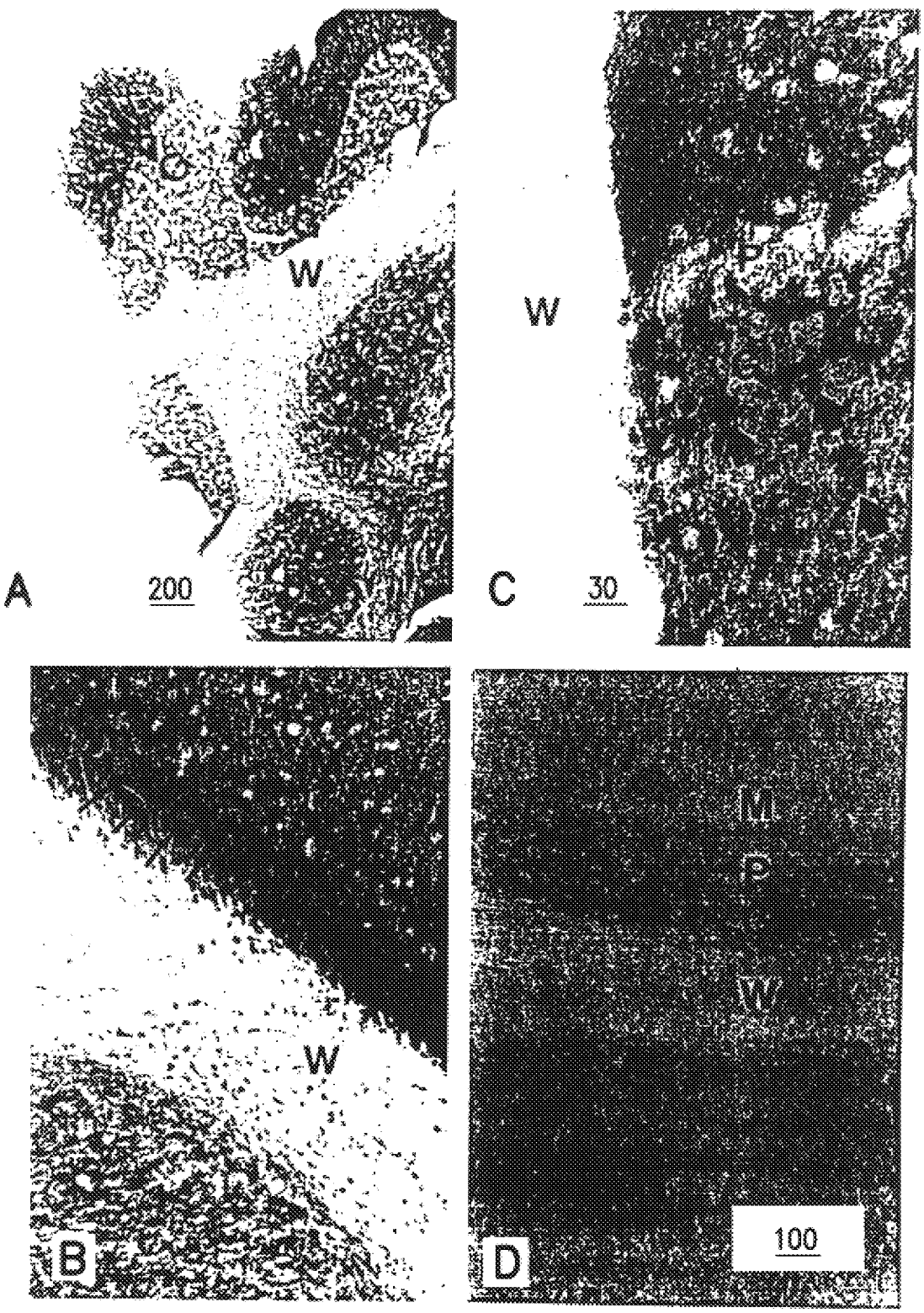

FIG. 20 shows distinct 4-1BB immunopositive reaction in the cerebellum at three progressively enlarged magnifications (a,b, and c).

Figure 21:
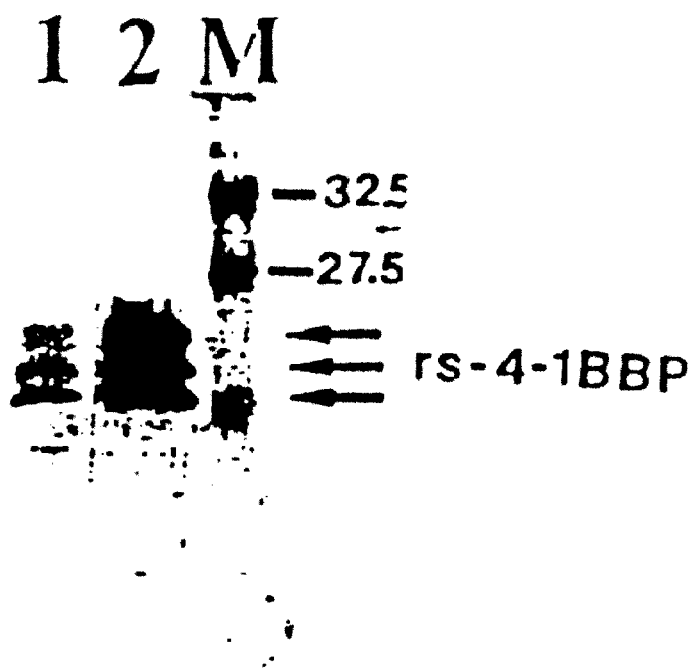

FIG. 21 shows purified re-4-1BBP in three bands of 18, 20, and 23, kDa (arrows): lane 1, Coomassie staining; lane 2, anti-4-1BB-O antibody staining; lane 3, molecular size marker.

Figure 22:
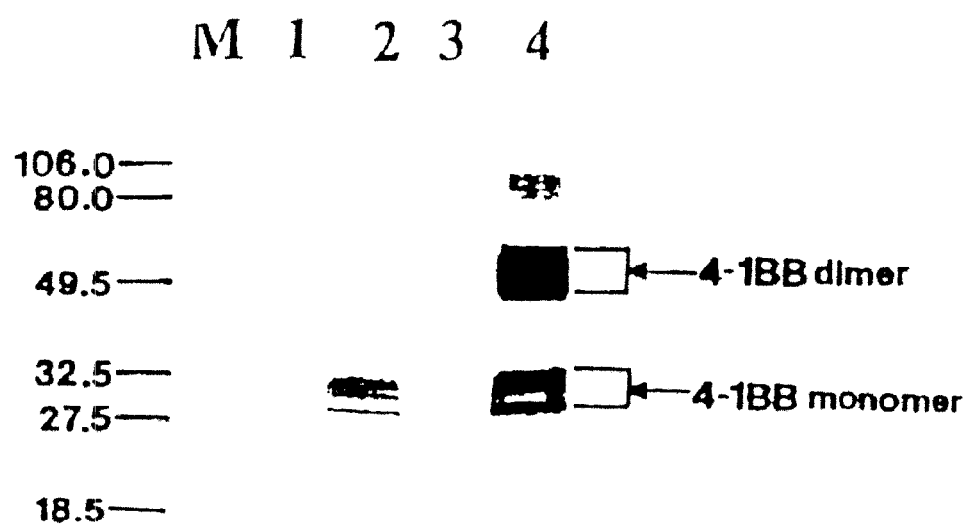

FIG. 22 shows recombinant 4-1BB protein fractionated on a 10% SDS polyacrylamide gel.

Figure 23:
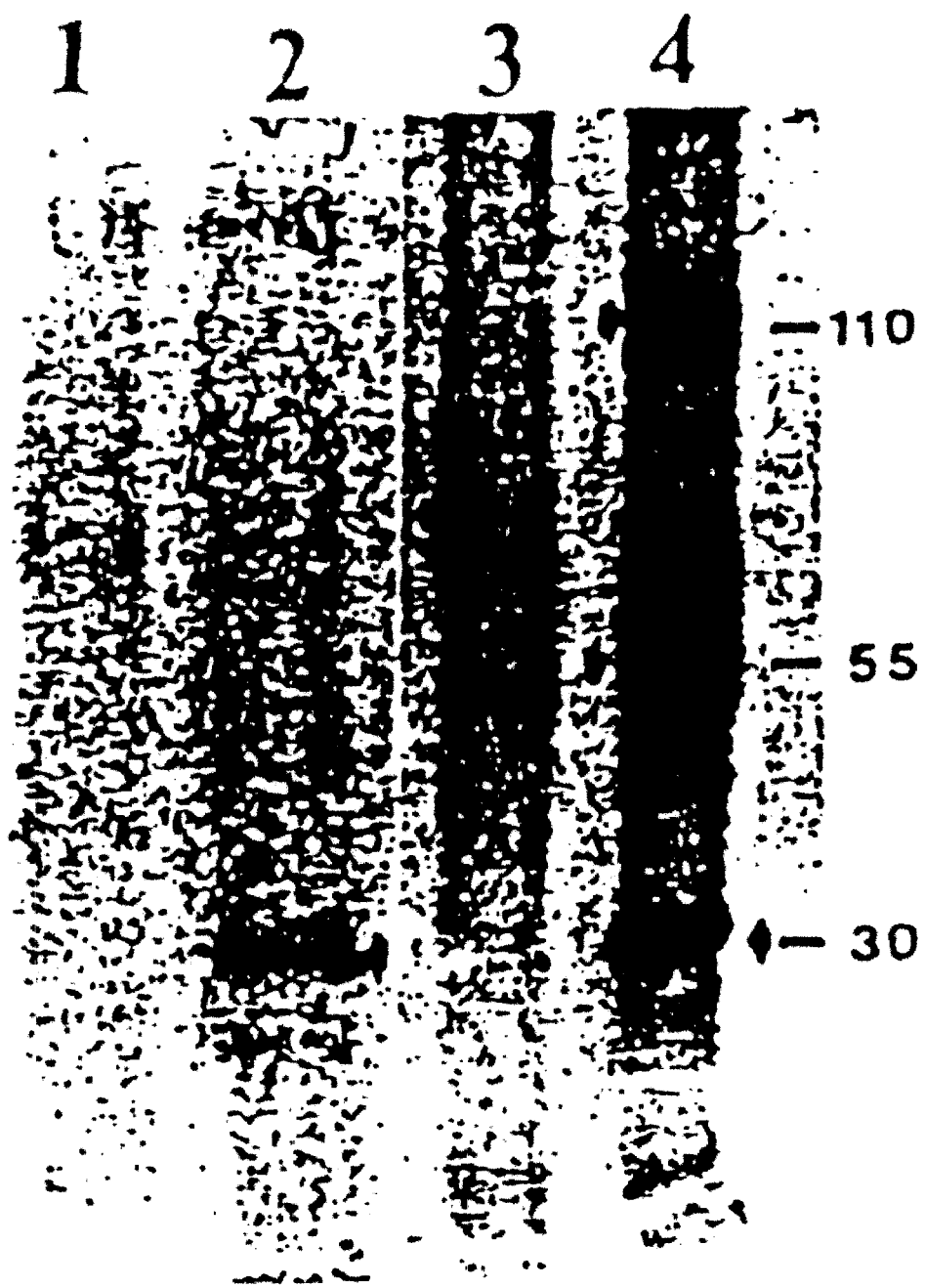

FIG. 23 shows an immunoprecipitation of cell surface 4-1BB protein synthesized by T lymphocytes.

Figure 24A:
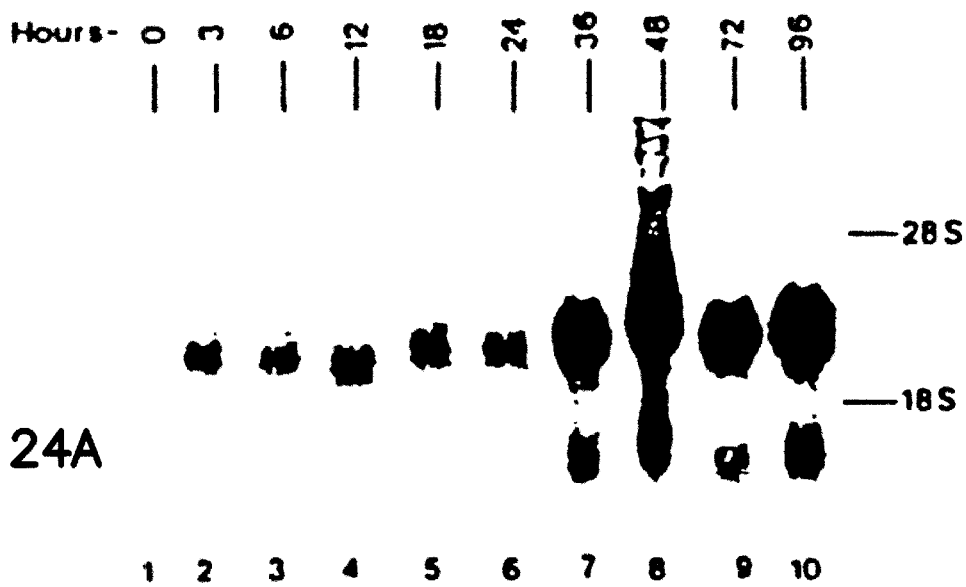
Figure 24B:

FIGS. 24a and 24B show that 4-1BB mRNA expression in induced murine splenic T cells by anti-CD3-activation.

Figure 25A:
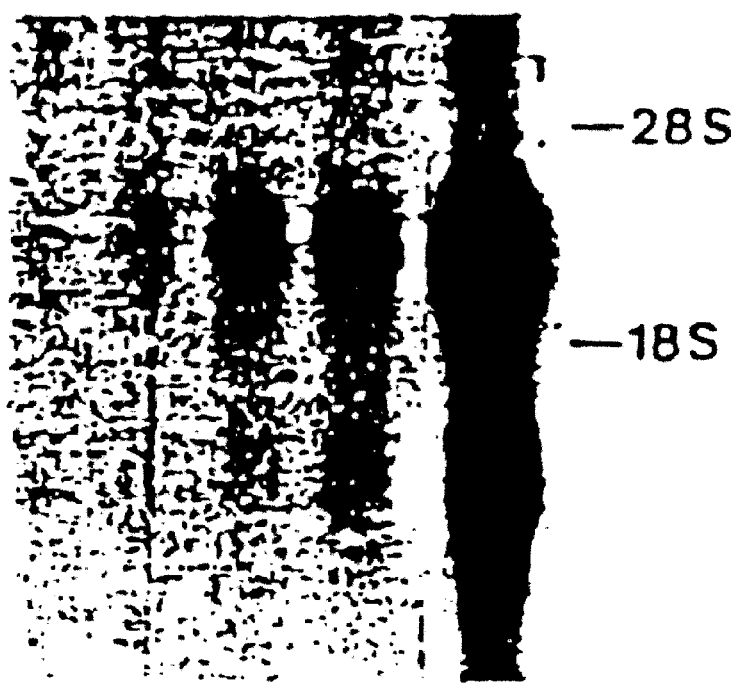
Figure 25B:
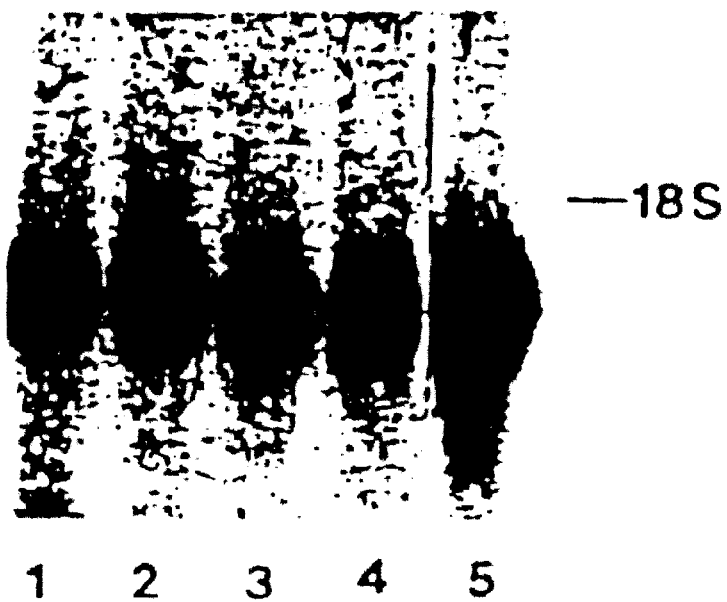

FIG. 25 shows that optimal induction of 4-1BB mRNA requires both Protein Kinase C activation and increases in intracellular $Ca^{2+}$; thymocyte culture were stimulated with medium alone (lane 1 ), 1 μM ionomycin (1) (lane 2 ), 10 ng/ml TPA (T) (lane 3 ), T+1 (lane 4 ) for 6 hours and monitored for 4-1BB mRNA expression by Northern analysis.

Figure 26A:
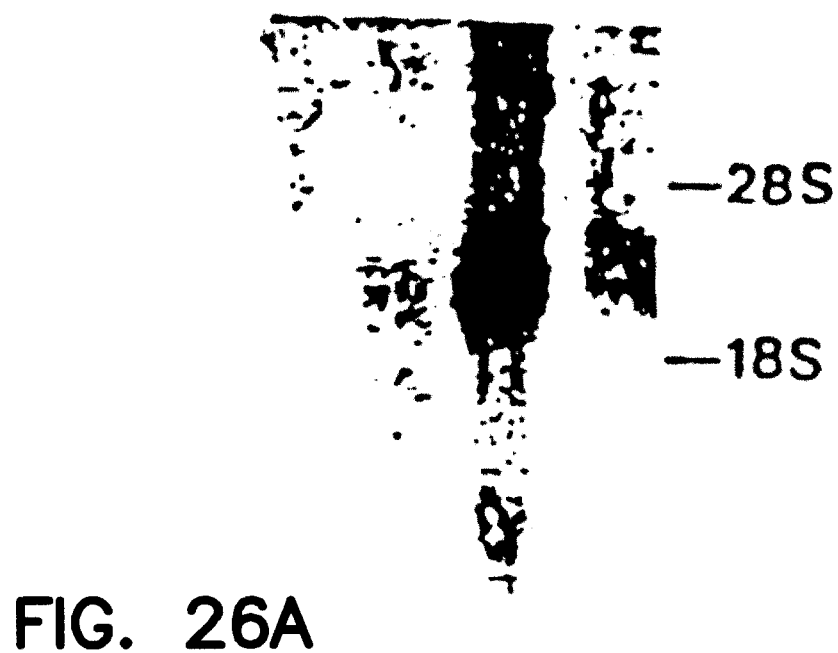
Figure 26B:

FIG. 26 shows a Northern blot analysis of Thymocytes cultures that were stimulated with medium alone (lane 1 ), 20 μg/ml CHX (lane 2 ), T+1 (lane 3 ), or CHX+T+1 (lane 4 ) for 6 hours and monitored for 4-1BB mRNA expression.

FIGS. 27a–d show that 4-1BB is expressed on the cell surface of activated thymocytes, splenic T cells, $CD4^+$ and $CD8^+$ T cells.

FIG. 28 shows a bar graph demonstrating that anti-4-1BB mAb, 53A2, enhances the prolifeation of anti-CD3-activated splenic T cells.

Figure 29A:
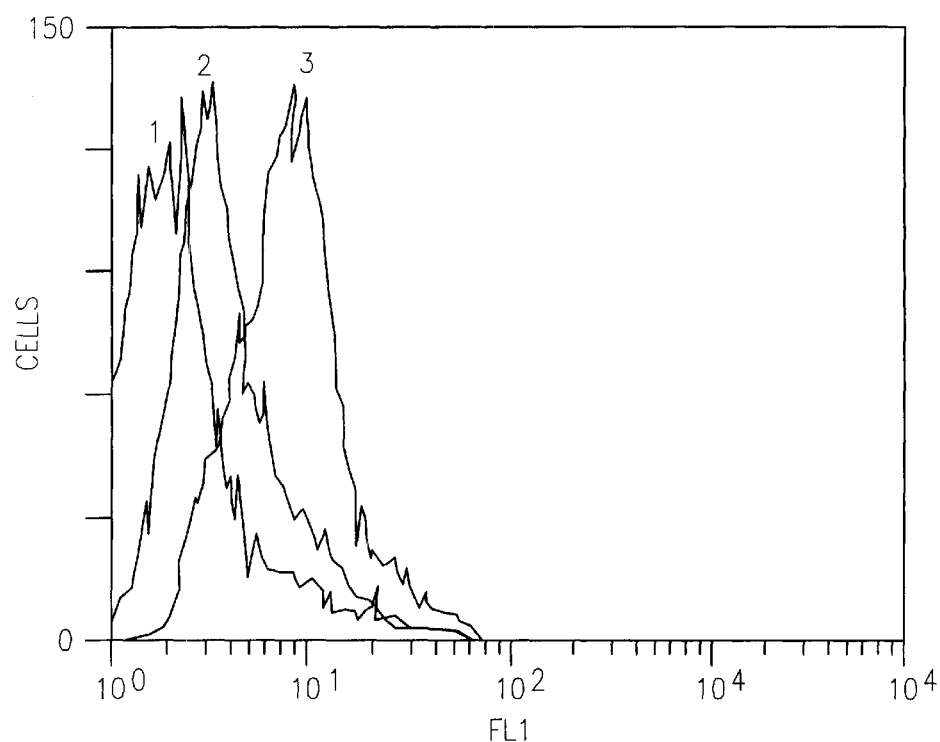
Figure 29B:
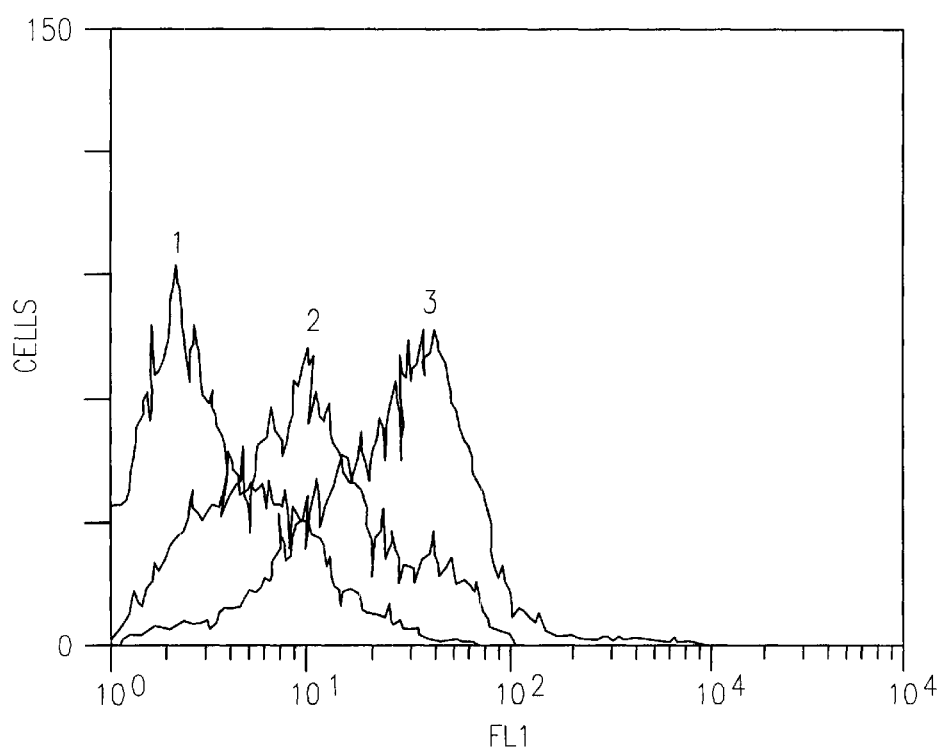
Figure 29C:
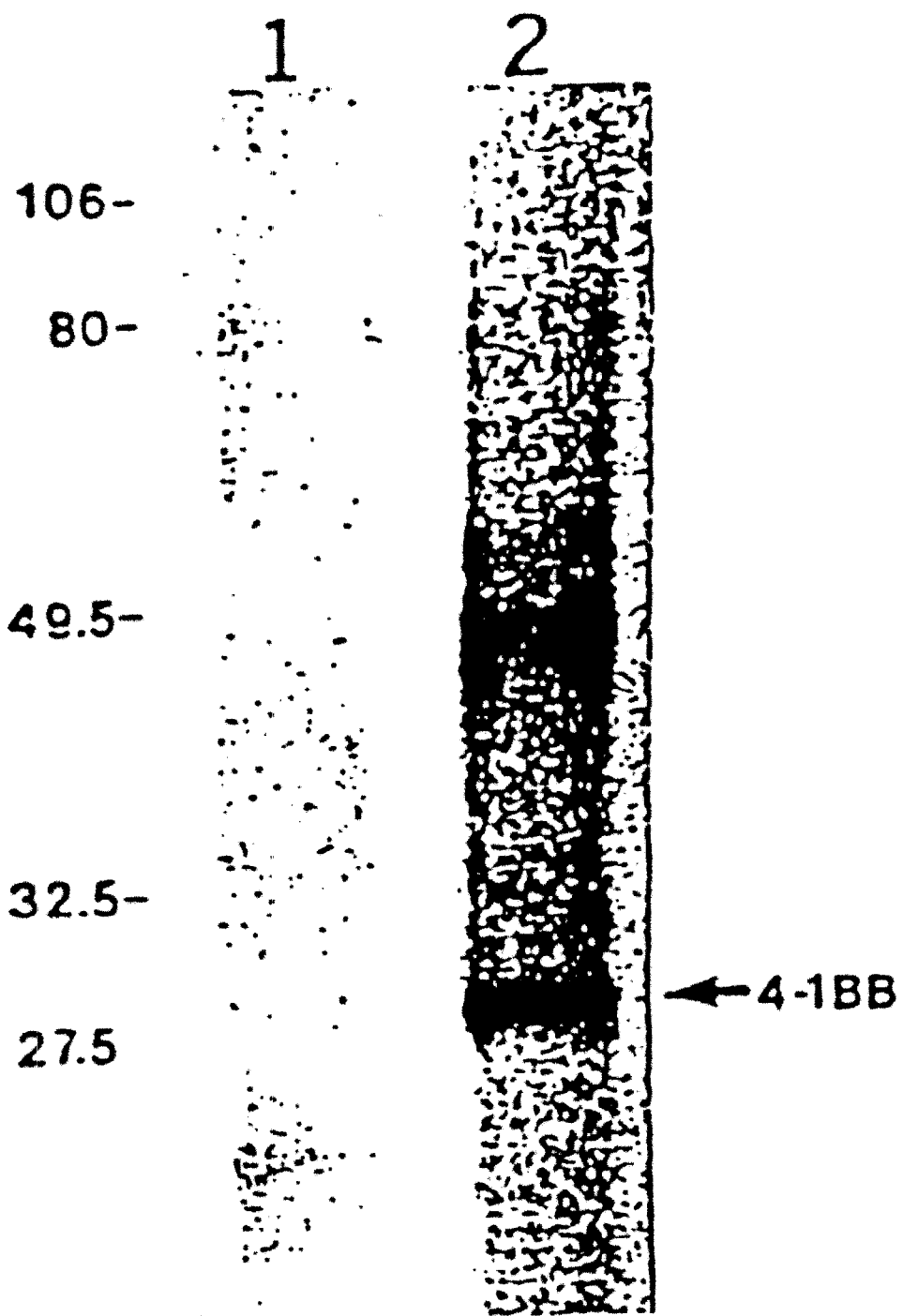

FIGS. 29a–c show specificity of 53A2 mAb to native and recombinant 4-1BB.

Figures 30A, 30B:
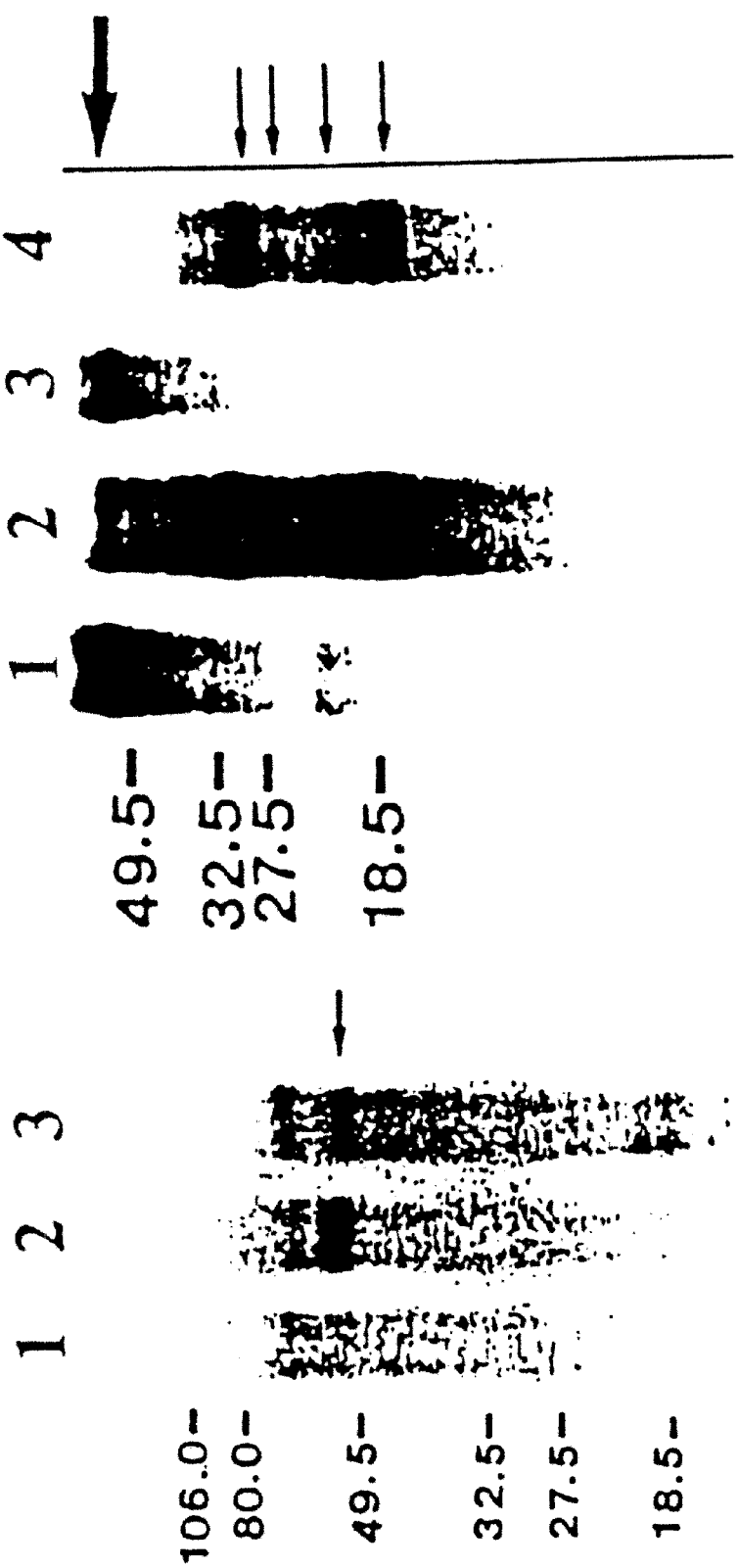

FIGS. 30a and 30b show the identification of the coimmunoprecipitated proteins.

Figures 31A, 31B:
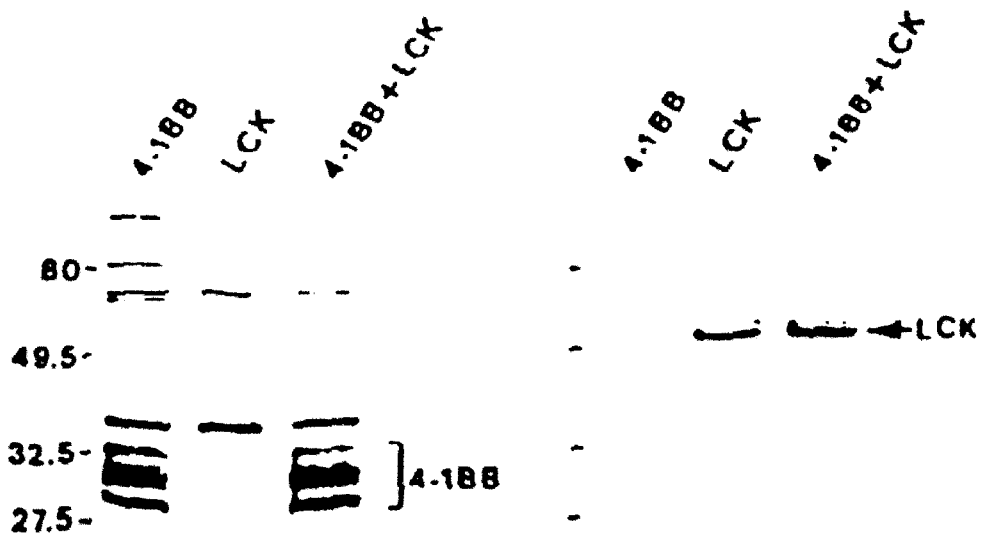
Figure 31C:
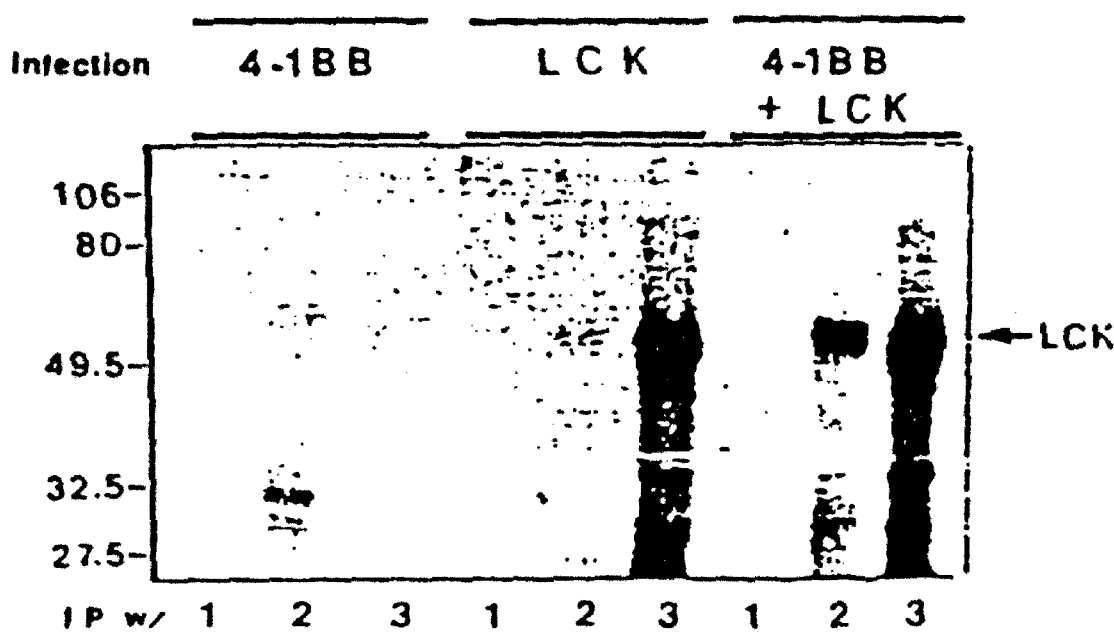

FIGS. 31a–c show an analysis of the association of 4-1BB and $p56^{lck}$ in a baculoviral expression system.

Figures 32A, 32B:

FIGS. 32a–c show an analysis of the association of 4-1BB and $p56^{lck}$ HeLa cells.

Figure 33:
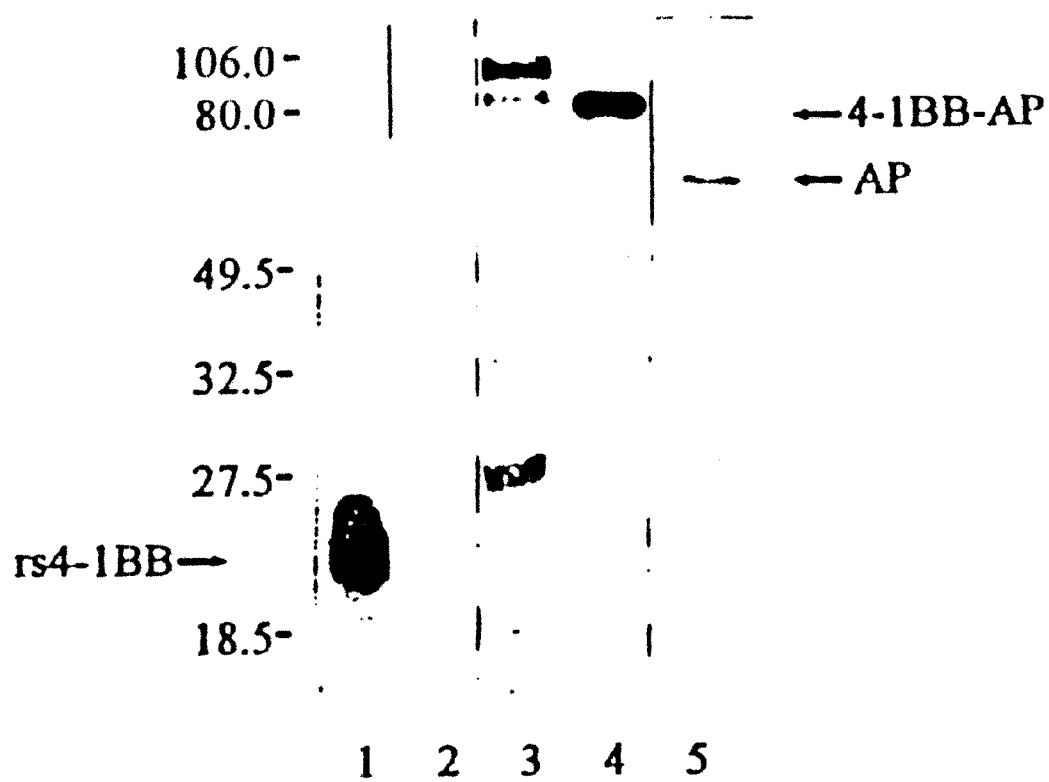

FIG. 33 is a Western analysis that shows the expression of the 4-1BB-AP fusion protein and rs4-1BB.

Figure 34A:
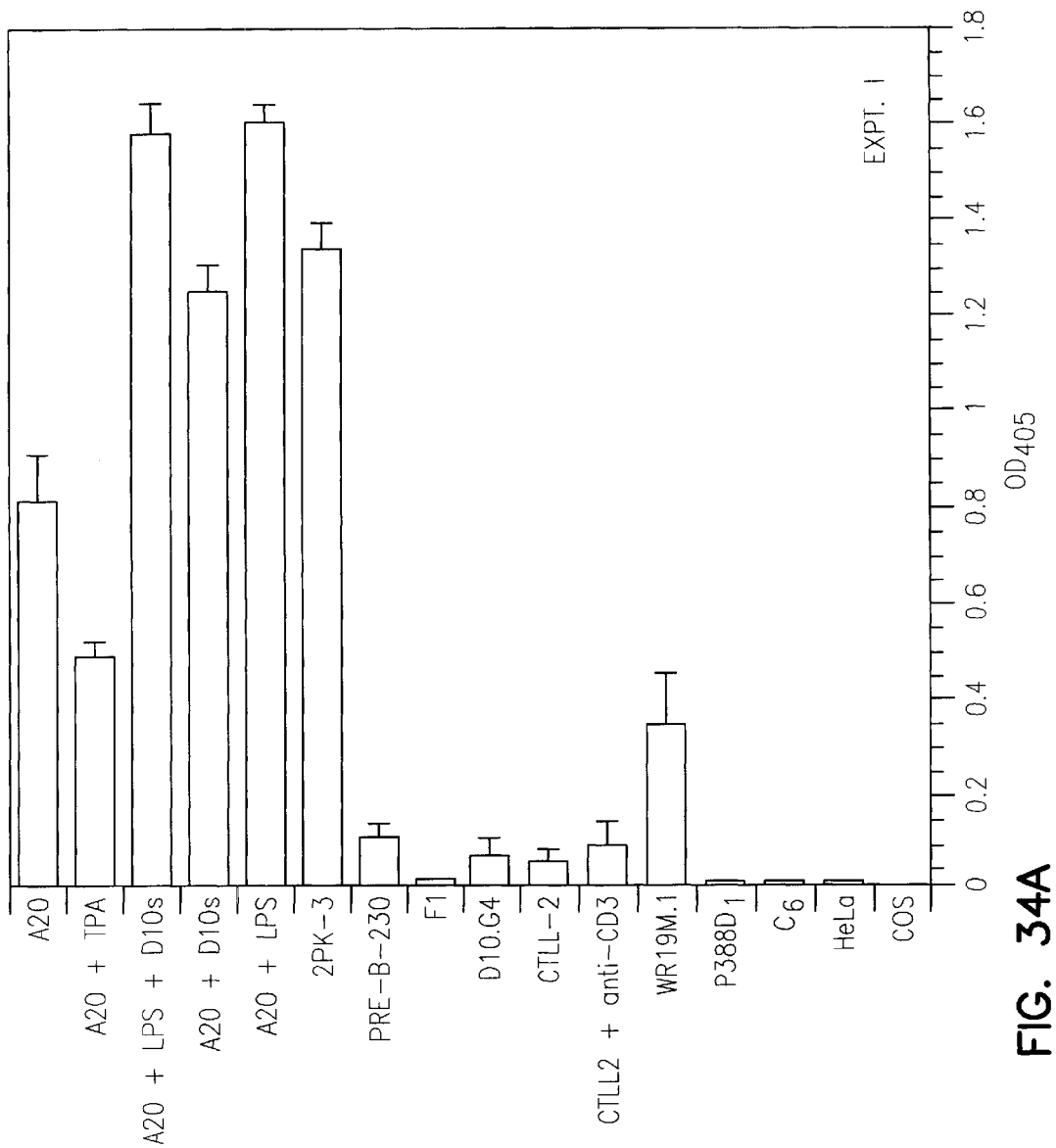
Figure 34B:
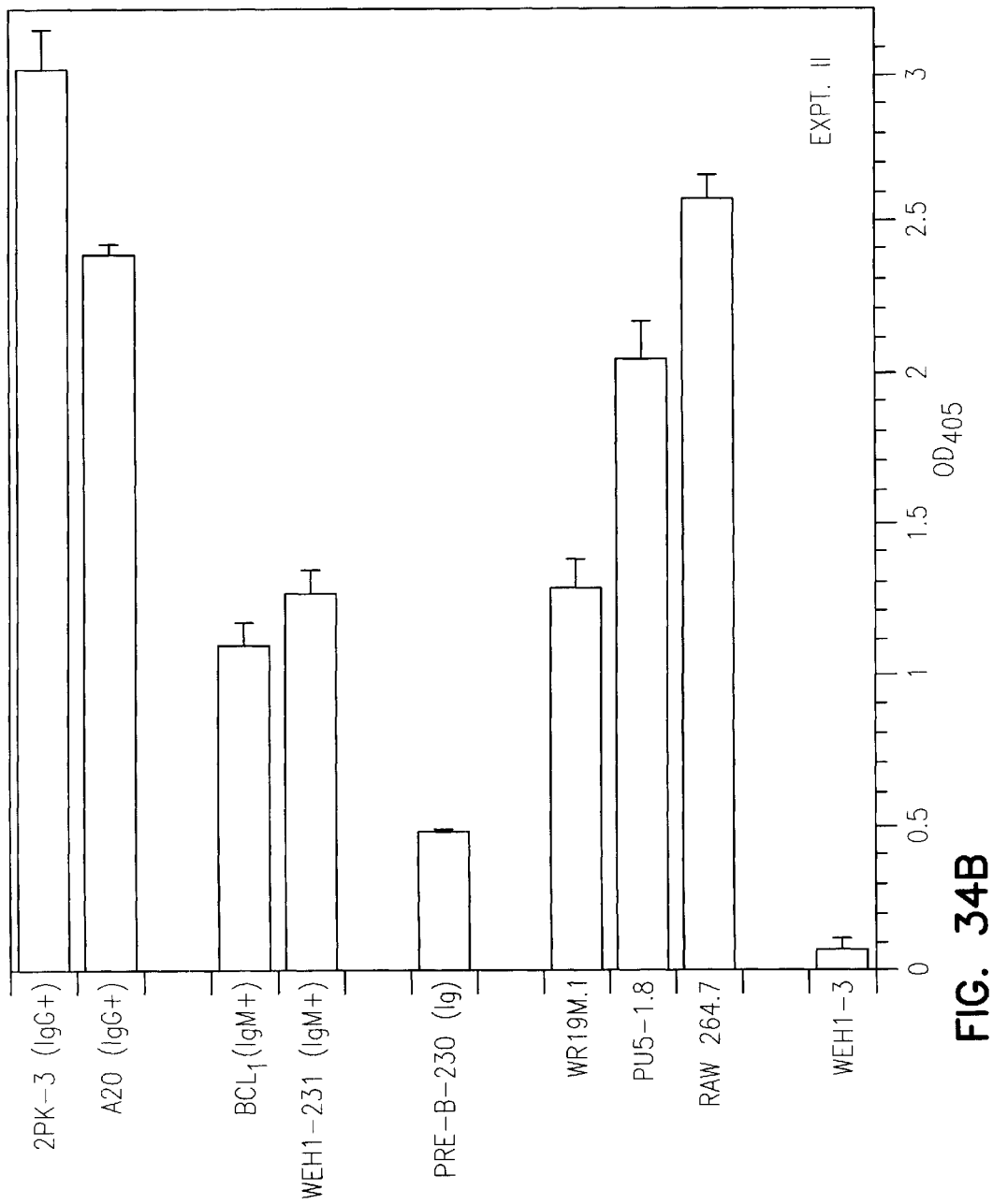
Figure 34C:
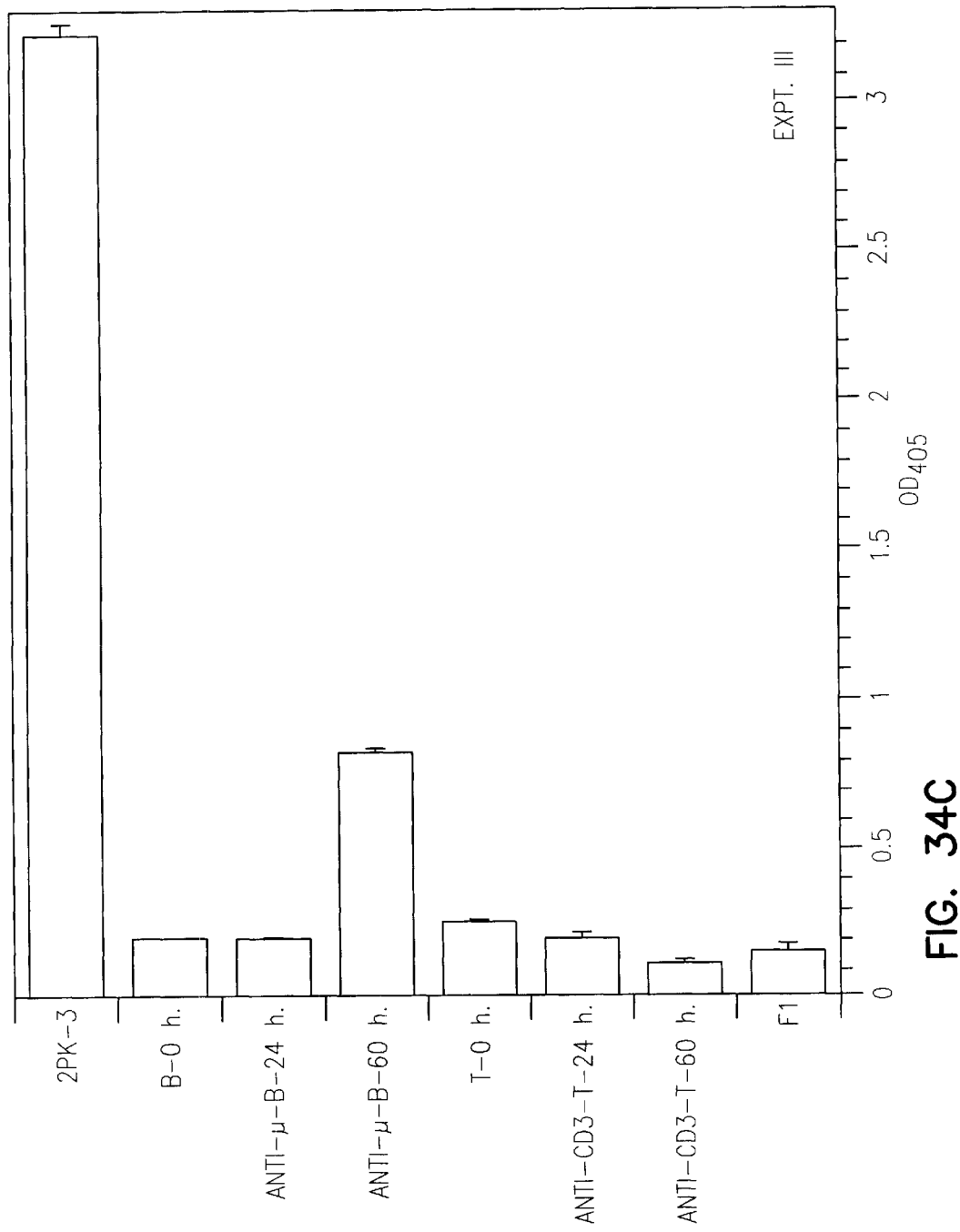

FIGS. 34a–c show the quantitative analysis of 4-1BB-AP binding to lymphoid- and nonlymphoid-cell lines.

Figure 35A:
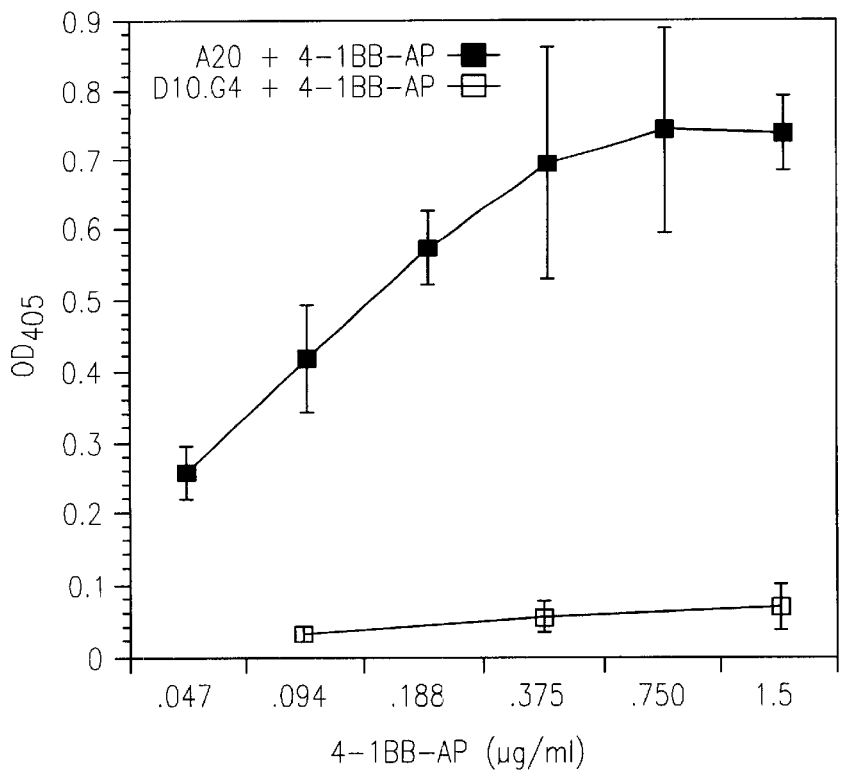
Figure 35B:
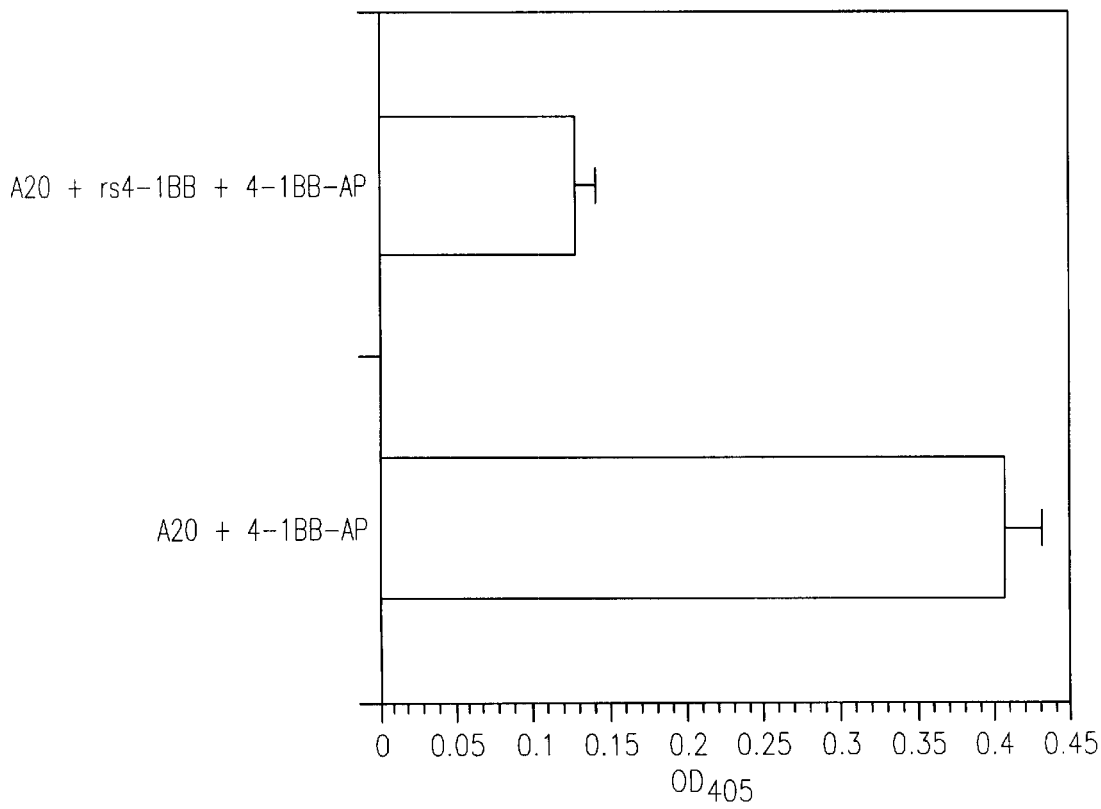

FIGS. 35a and 35b show the characterization of 4-1BB-AP binding to A20 B-cell lymphoma cells.

Figure 36:
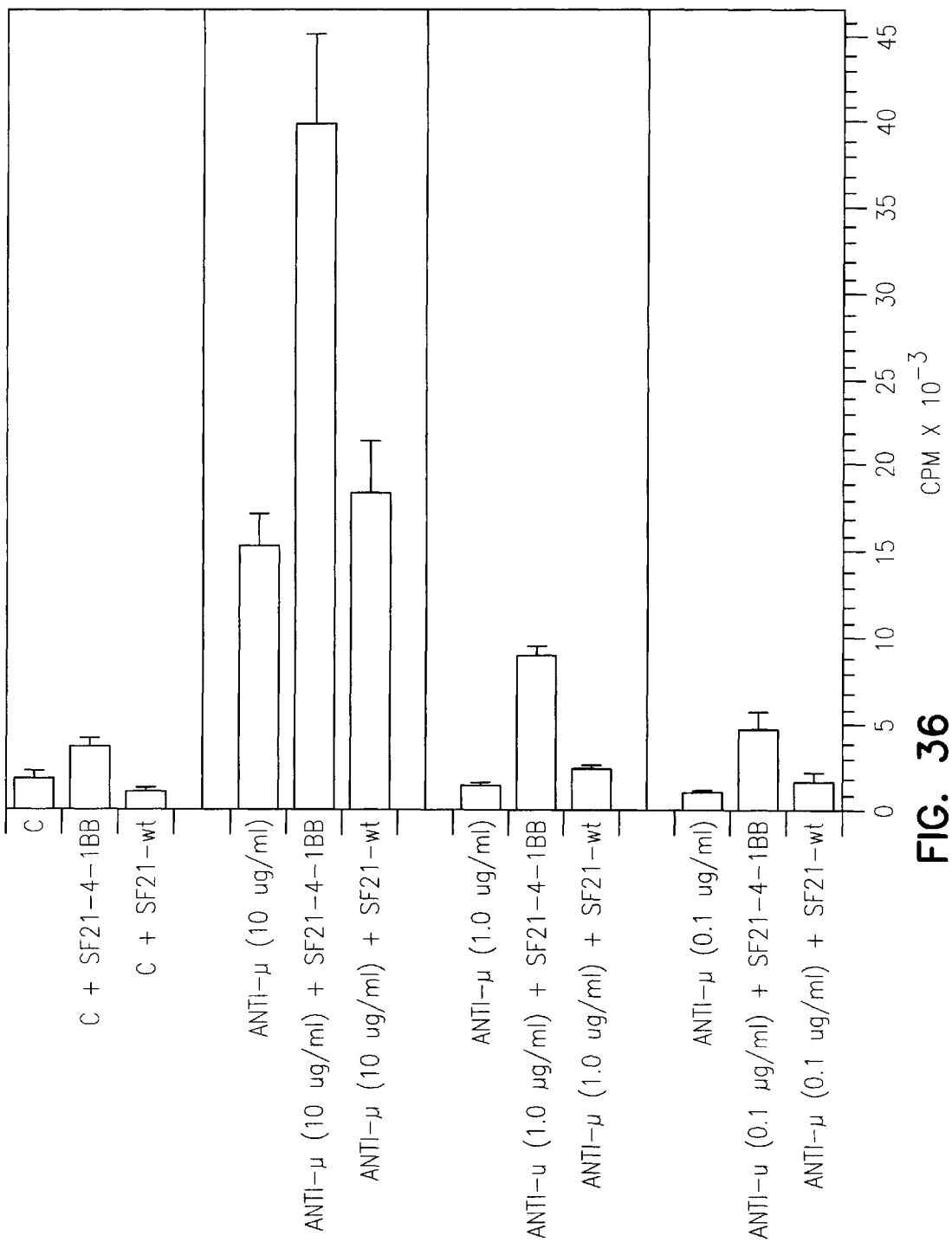

FIG. 36 shows the costimulation of anti-r-primed B cells with fixed-SF21-4-1BB cells.

DETAILED DESCRIPTION

In the following detailed description a successive series of studies are presented which characterize the receptor 4-1BB. References are made to known procedures and studies, as well as published work of the applicant. These publications are incorporated herein by reference for clarity and listed in an appendix included at the end of this detailed description.

The following abbreviations are used herein: CTL, cytolytic T lymphocyte; HTL, helper T lymphocyte; LGL, large granular lymphocytes; NK, natural killer cells; SDS, sodium dodecylsulfate; SSC, 150 mM sodium chloride/15 mM sodium citrate, pH 7.0; TPA, 12-0-tetradecanoylphorbol-13-acetate. Th, helper T lymphocytes; IL-2, interleukin 2; IL-3, interleukin 3; rIL-2, recombinant Il-2; CSF-GM, granulocyte/macrophage colony-stimulating factors; cRNA, complementary RNA; ss, single-stranded; ds, double-stranded; TCR, T-cell antigen receptor; PTA, phorbol 12-tetradecanoate 13-acetate; r, recombinant; mu, murine; hu, human; MIP, macrophage inflammatory protein; BFU-E, burst forming unit-erythroid, an erythroid progenitor cell; CFU-GEMM, colony forming unit-granulocyte erythroid macrophage, megakaryocyte, a multipotential progenitor cell; CFU-GM, colony forming unit-granulocyte macrophage, a granulocyte-macrophage progenitor cell; CFU-S, colony forming unit-Spleen, a multipotential stem cell; H-ferritin, the heavy chain subunit form of ferritin; MGF, mast cell growth factor, a c-kit ligand; CSF, colony stimulating factors; G, granulocyte; M, macrophage; Epo, erythropoietin; IL, interleukin; LD, low density; $NALDT^-$, non-adherent low density T-lymphocyte depleted; PMSF, phenylmethylsulfonyl fluoride; PBS, phosphate buffered saline; MIP-1α-R, MIP-1α receptor; rMIP-1α, recombinant MIP-1α protein; nMIP-1, native macrophage inflammatory protein-1; AcNPV, *Autographa californica* nuclear polyhedrosis virus; SDS, sodium dodecyl sulfate; LPS, lipopolysaccharide; ConA, concanavalin A; DTT, dithiothreitol; mAb, monoclonal antibody.

Initial Isolation and Sequencing of 4-1BB

MATERIALS AND METHODS

Cells cloned murine CTL L3 cells (1), are thy-1,$2^+$, Lyt-$2^+$, LFA-$1^+$, LeT4$^-$and H-2L$^d$ reactive. Cloned murine HTL L2 cells (2) are Thy-1,$2^+$, LFA-$1^+$, Lyt-$2^-$LeT4$^+$ and Mls$^{a/d}$ reactive.

Methods of isolating and maintaining the cloned helper T lymphocytes (Th), L2, and the cloned cytolytic T lymphocytes (CTL), L3, have been described in the above identified publication. To stimulate the cloned T cells, we resuspended them at $10^6$–$10^7$ cells per ml and cultured them with Con A (Pharmacia) at 10 ug/ml for L2 cells or 2 ug/ml for L3 cells or human recombinant IL-2 (rIL-2; Cetus) at $10^2$–$10^3$ units/ml. Immobilized clonotypic monoclonal antibody 384.5, which reacts with the TCR of L3 cells (2), was used to stimulate L3 cells.

Mouse thymoma cells, EL4, and mouse B-cell lines, A20.2j and K46, were maintained in RPMI 1640 medium containing 5% fetal calf serum. EL4 cells were stimulated with phorbol 12-tetradecanoate 13-acetate (PTA; 10 ng/ml) for up to 20 hr, monitoring the stimulation by IL-2 assay (3).

cDNA Libraries. RNAs of L2 and L3 cells that were stimulated by Con A for 14 hr. were extracted (4) and poly(A)$^+$ mRNA was purified on an oligo(dT)-cellulose column (5). Double-stranded (ds) cDNA was synthesized from the poly(A)$^+$ mRNA (6). The cDNA was methylated at EcoRI sites, EcoRI linkers were ligated to cDNA, and then the cDNA was enriched for molecules larger that 250,000 daltons by passage over Bio-Gel A-150m columns. The cDNAs were inserted into the EcoRI Site of gt10 bacteriophage cloning vector (7).

cDNA Probe. Six micrograms of poly(A) mRNA was denatured with 10 mM methylmercuric hydroxide and incubated in a buffer containing 100 mM Tris HCI at pH 8.3, 50 mM KCl, actinomycin D at 50 mg/ml, 30 mM 2-mercaptoethanol, 10, mM $MgCl_2$, $(dt)_{12-18}$ at 5 ug/ ml, 0.5 mM each of dATP, dCTP, and dGTP, 0.01 mM dTTP, 0.001 mM [$\alpha$-$^{32}$P]dTTP (3000 Ci mmol$^{-1}$; 1 Ci=37 GBq), and reverse transcriptase from avian myeloblastosis virus at 1000 units/ml at 46° C. for 30 min. Single-stranded (ss) cDNA was freed from its template RNA by incubation in 200 mM NaOH/10 mM EDTA at 60° C. for 30 min and passed over a 4-ml column of Sephadex G-100. The specific activity of the probe was usually ~1.6–2.0×$10^8$ cpm/ug of cDNA.

Subtracted cDNA Probe. The ss cDNA prepared from L2 RNA was hybridized to a $R_o t$ of 1200–1500 (mol of nucleotide per liter)×sec with poly(A)$^+$ mRNA of A20.2j in 0.41 M sodium phosphate buffer, pH 6.8, containing 0.1% NaDod-$SO_4$ and 1 mM EDTA, in a volume of 25–50 ul. The ss cDNA fraction was collected by chromatography through a hydroxylapatite column as recommended by the vendor (Bio-Ran). Seven percent of input cDNA was recovered in the ss fraction and used for a second round of hybridization to A20.2j poly(A)$^+$ mRNA to an equivalent $R_o t$ of 500 (mol/liter)×sec. Approximately 93% of initial input radioactivity was recovered. Starting with 6 ug of poly(A)$^+$ mRNA, approximately 5.5×$10^6$ cpm was obtained as a probe.

DNA and RNA Blot Hybridization. Recombinant phage DNA was prepared (8) and digested with EcoRI. DNA fragments were transferred to GeneScreenPlus membranes (New England Nuclear) and hybridized with ss cDNA probes (9). RNA was run on 1.2% formaldehyde denaturing agarose gel (10) and transferred to GeneScreenPlus. Probes for RNA hybridization were prepared from gel-purified cDNA inserts by the random priming method (11). Total cytoplasmic RNA of poly(A)$^+$ RNA were fractionated on 1.2% agarose-formaldehyde gels and transferred to GeneScreenplus (NEN, Boston, Mass.). Gel-purified eDNA inserts were [$^{32}$P]-labeled by nick translation and used as probes. When a Northern blot of GeneScreenplus was used multiple times for hybridization, the previous probe was removed by treating the membrane in 10 mM Tris-Hcl (pH7.0) and 0.2% SDS at 85° C. for 1 hr.

High molecular weight DNA of mouse spleens was prepared as described previously (12). Endonuclease digests of DNA were electrophoresed in 0.8T agarose gel at 4° C. The DNA was denatured, and transferred to GeneScreenPlus as described by Southern (13). The blot hybridized with [$^{32}$P]-labeled cDNA inserts.

L2 cells were stimulated with concanavalin A (10 ug/ml) for 14 hr, at a cell concentration of $10^6$–$10^7$/ml. L3 cells were stimulated with concanavalin A (2 ug/ml) for 14 hr, at a cell concentration of 2.5×$10^6$/ml. Mouse thymoma EL-4 cells (14) were stimulated with 12-0-tetradecanoylphorbol-13-acetate (TPA, 10 ng/ml) at a cell concentration of 1.0× $10^6$/ml for 20 hr; stimulation was monitored by Il-2 assay (3). B cell lymphoma K46 (15), and rat Nk cell LGL (16) were not stimulated with any of above reagents.

Figure 1A:
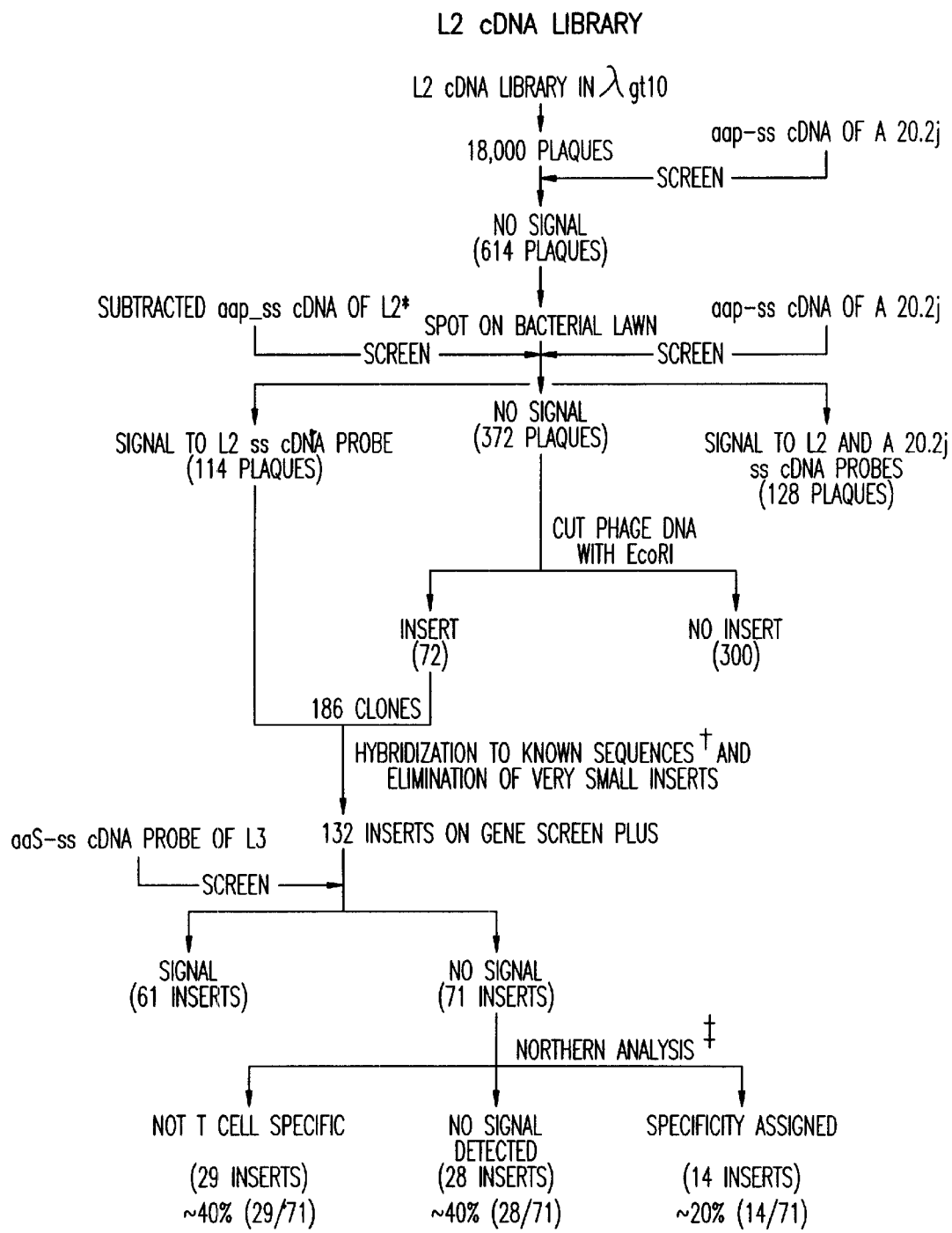
FIGS. 1a and 1b are flow sheets of the present inventor's approach to identifying L2 (helper T lymphocyte) specific and L3 (Cytolytic T lymphocyte) specific cDNA clones.
Figure 1B:
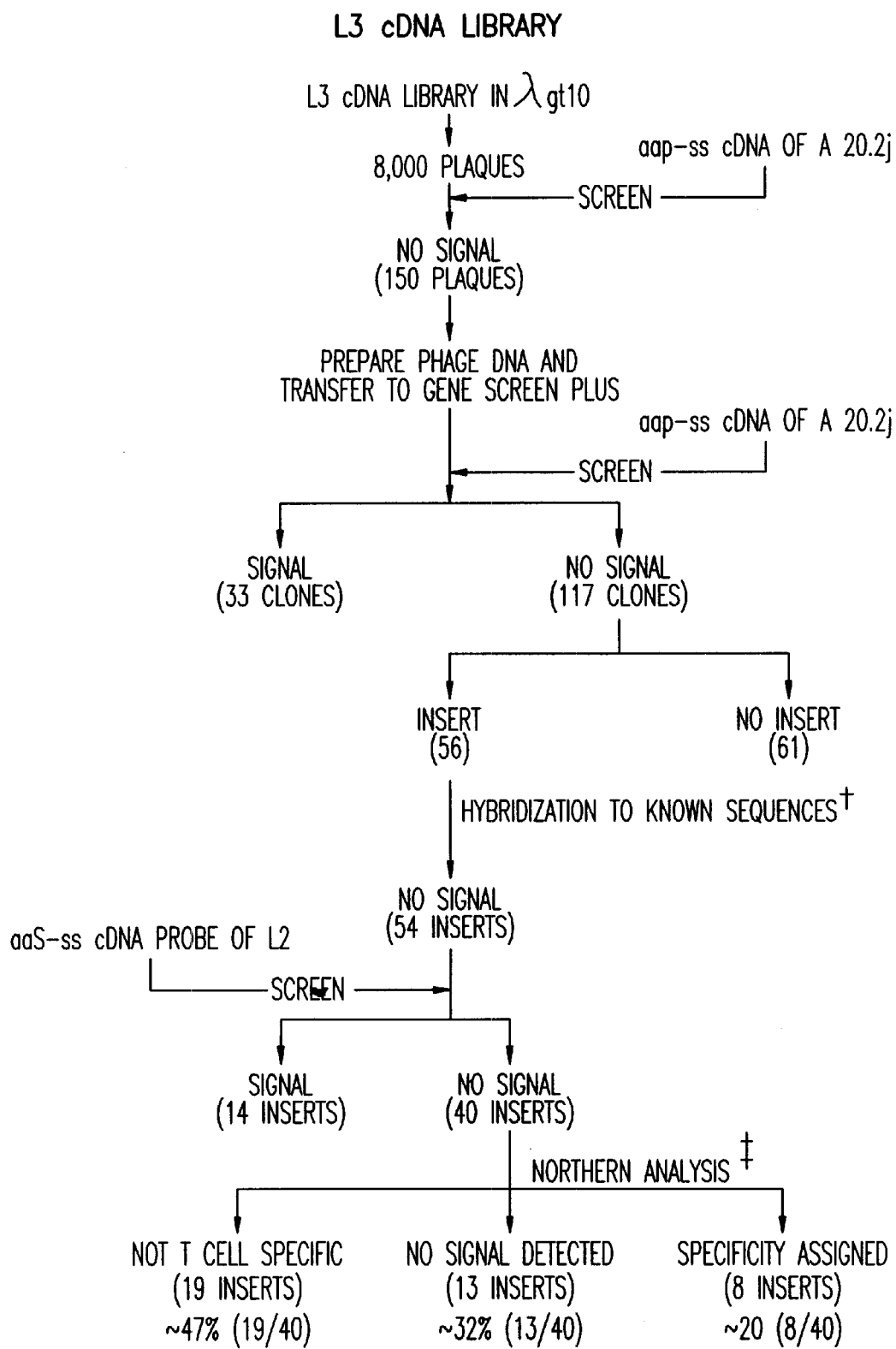

FIGS. 1a and 1b are flow sheets of the present inventor's approach to identify L2-Specific and L3-specific cDNA clones. Therein: 1) the * means that preparation of subtracted L2 cDNA probe is described in Materials and Methods; 2) the + means the probes of known sequences were prepared for cDNAs of granulocyte/macrophage colony-stimulating factors (CSF-GM), interleukin 3 (IL-3), IL-2, TCR $\alpha$-chain, TCR $\beta$-chain, c-myc, and c-fos; 3) ++ means the insert of each negative recombinant phage DNA was gel-purified and used as a probe for RNA blot hybridization ("Northern") analysis of K46, unstimulated or PTA-stimulated EL4, large granular lymphocytes (LGL), and unstimulated or Con A-stimulated L2 and L3. The [$^{32}$P]-labeled cDNA probe, prepared from poly(A)$^+$ mRNA of A20.2j, was used to screen the library. The total cDNA probe could detect a clone corresponding to 0.02–0.05% of the test mRNA (17). Of 18,000 plaques from the L2 cDNA library, 614 (3.4%) failed to hybridize to the B-cell cDNA probe. The subtracted L2 cDNA probe was hybridized to these 614 plaques and 114 (18%) gave a signal; 372 plaques gave no signal to the subtracted L2 cDNA probe or B-cell cDNA probe. Of those 372, 72 clones (19%) contained cDNA inserts. The 186 (114+72) clones from the L2 cDNA library were subjected to further analysis.

By similar analysis of approximately 8000 L3 cDNA clones, 150 plaques (2.0%) that failed to hybridize to P-labeled B-cell cDNA probe were selected. Instead of screening the 150 plaques with subtracted L2 cDNA probe, we digested recombinant phage DNA of each clone with EcoRI and immobilized the fragments on the filter. $^{35}$S-labeled B-cell cDNA probe was used to hybridize to the filters. The use of $^{35}$S for cDNA labeling and Southern analysis increased the sensitivity at least 5-fold. Fifty-six inserts (FIG. 1b) from L3 were identified, each of which failed to hybridize to the B-cell cDNA probe.

One Hundred and eighty-six L2 cDNA inserts and 56 L3 cDNA inserts were hybridized to cDNAs of CSF-GM, IL-3, IL-2, TCR $\alpha$-chain, TCR $\beta$-chain, c-myc, and c-fos. Twelve clones hybridized to cDNA, for IL-3, 6 to CSF-GM, 3 to IL-2, 2 to TCR $\beta$-chain, and 1 each to TCR $\alpha$-chain and c-myc (Table 1). Twenty-nine clones whose cDNA inserts were less than 50 base pairs (bp) were eliminated from further study. The blots containing 132 L2 cDNA and 54 L3 cDNA inserts were hybridized to S-labeled ss cDNA probe prepared from poly(A)$^+$ mRNA of unstimulated L3 or of unstimulated L2, respectively. Sixty-one inserts of L2 cDNA hybridized to the L3 cDNA probe and 14 inserts of L3 cDNA hybridized to the L2 cDNA probe.

TABLE 1

T-cell specific cDNA clones isolated from L2 and L3 cDNA library

| Origin | Group | cDNA clone | Number of times isolated |
|---|---|---|---|
| L2 | 1 | CSF-GM | 6 |
| | 2 | IL-3* | 12 |
| | 3 | IL-2 | 3 |
| | 4 | TCR α-chain | 1 |
| | 5 | TCR β-chain | 2 |
| | 6 | c-myc | 1 |
| | 7 | pBK791 | 4 |
| | 8 | pBK642 | 1 |
| | 9 | pBK671 | 1 |
| | 10 | pBK631 | 3 |
| | 11 | L2G53#3 | 1 |
| | 12 | L2G95#3 | 1 |
| | 13 | L2G95#4 | 1 |
| | 14 | L2G25#4 | 1 |
| | 15 | L2S35#3 | 1 |
| | | Total | 39 |
| L3 | 1 | TCR β-chain | 2 |
| | 2 | L3G29#4 | 1 |
| | 3 | L3G25#4 | 1 |
| | 4 | L3G14#2 | 1 |
| | 5 | L3G10#6 | 1 |
| | 6 | L3G7#1 | 1 |
| | 7 | L3G18#3 | 1 |
| | 8 | L3G26#1 | 2 |
| | | Total | 10 |

T-cell-specific cDNA clones were isolated from ~18,000 clones of L2 library and 8000 clones of L3 library. After enrichment of T-cell-specific sequences, cDNA clones for CSF-GM, IL-3, IL-2, TCR α-chain, TCR β-chain, and c-myc were detected by hybridization with the corresponding full-length cDNA provided by other laboratories. By cross-hybridization, the other clones (14 from L2 and 8 from L3) turned out to represent 16 different genes (9 from L2 and 7 from L3). Those cDNA clones representing 16 different genes were subjected to further analysis.

A partial sequence analysis revealed that the IL-3-related clones contained two different species.

The 71 (132-61) inserts from L2 and 40 (54-14) inserts from L3 were used as probes with blots of 10 ug of poly(A)$^+$ mRNA from K46, LGL (rat NK cell) (18), unstimulated or PTA-stimulated EL4, and 10 ug of total RNA from unstimulated or Con A-stimulated L2 or L3 cells.

Among these inserts, 29 (~40%, 29/71) from L2 and 19 (~47%, 19/40) from L3 hybridized to K46 or all lanes. Fourteen inserts (~20%, 14/71) from L2 hybridized only to Con A-stimulated L2, or both of L2 and L3 RNA. Those cDNA inserts represented nine different cDNAs. From L3, 8 (20%, 8/40) were T-cell specific, representing seven different genes; one gene was inducible by Con A in both L2 and L3, three genes were expressed constitutively and inducible by Con A only in L3 cells; and the rest were inducible by Con A in L3 cells.

A in L3 cells but not found in unstimulated L3 cells. Twenty-eight inserts (40%, 28,71) from the L2 cDNA library and 13 inserts (~32%, 13/40) from the L3 library did not hybridize to any of the RNAs. Because less L2 or L3 RNA was available for blot hybridization analysis, we have not been able to eliminate the possibility that those inserts not expressed in K46, EL4, or LGL could still be expressed in L2 or L3 at a low level.

Screening of cDNA Library and DNA Sequencing. L2 and L3 cDNA libraries which were previously prepared were rescreened with cDNA insert of each of 14 T Cell-specific genes. Typically 10 positive clones were chosen for each species and the sizes of cDNA inserts were determined. The longest cDNA inserts were employed for nucleotide sequence analysis. DNA restriction fragments, subcloned in M13 vectors (19), were sequenced by the dideoxy chain termination technique (20) employing Sequinase (U.S. Biochemical, Cleveland, Ohio.), with modification made to accommodate 2"-deoxyadenosine 5"-[α[$^{35}$S] thio] triphosphate (21).

Nucleotide and Protein Sequence Comparison. Full length cDNA and predicted protein sequence were compared with the sequences in the GeneBank (NIH) DNA Sequence Library, European Molecular Biology Laboratories (EMBL) and National Biomedical Research Foundation (NBFR). Predicted protein were analyzed by Pepplot program.

Table 2 summarizes T cell cDNAs identified from 14 hr ConA-stimulated L2 and L3 cDNA libraries. Besides the cDNAs listed in the table, CSF-GM, IL-2, IL-3, α-, β- T cell receptor and c-myc cDNAs were identified by cross-hybridization of T cell enriched cDNAs with the corresponding full-length cDNA provided by other laboratories.

TABLE 2

SUMMARY OF cDNA CLONES IDENTIFIED

| Full Length cDNA | cDNA Clone* Isolated Previously | Specificity of Expression | Identification |
|---|---|---|---|
| 4-1BB | L3G29$3, L3G25#4, L3G14#2 | L2 and L3 | previously unknown |
| L2G25B | L2G25#4, | L2 and L3 | previously unknown (MIP-1α) |
| | L2G95#4, L2G53#3, L2G95#3 | | (related to PLD78) |
| L2S35 | L2S35#3, L2PBK671 | L2 only | proenkephalin |
| 8-1R | L2PBK791, L2PBK642, L2PBK631 | L2 and EL-4 | T cell replacing factor |
| L3G10 | L3G10#6, L3G18#3 | L3 only | HF gene (serine esterase) |
| N.D.** | L3G7#1 | L3 AND EL-4 | unknown |
| N.D.** | L3G26#1 | L3 and EL-4 | unknown |

*The cDNA clones were isolated independently and described as separate clones in the above identified publication May 1987 Proc. Natl. Acad. Sci. USA. 84, 2896–2900.
**The full length version of the two clones was not isolated.

Among the 16 unidentified T cell genes two represented proenkephalin which was identical to the sequence reported by Zurawski et al (22), three were T cell replacing factor (23), and two represented T cell serine esterase gene (24).

Four species were from different regions of cDNA represented as L2G25B (800 bases pairs). L2G25B was homologous to a human cDNA PLD 78 915) of unknown function. Three Species (L3G29#4, L3G25#4 AND L3G14#2) were from different regions of 4-1BB (2,400 base pairs). There were no reports of sequences homologous to 4-1BB. L3G7#1 and L3G26#1 were not characterized vigorously since we could not isolate longer inserts and their expression was very low in L3.

In the previous studies, 13 L3 cDNAs were isolated whose specificity were not assigned by RNA blot analysis. One of them (13-1) was 64% homologous to reported T cell serine esterase (25). The sequence was reported as a new member of T cell serine esterase (26).

The nucleotide sequence of three overlapping cDNA clones represented by 4-1BB was determined according to the strategy shown in FIG. 2a. The nucleotide sequence of 4-1BB revealed a single long open reading frame, beginning with the ATG codon at nucleotide residues 1–3 (FIG. 2b.). This reading frame codes for a polypeptide of 256 amino acids with a molecular weight of 27,587. The assigned ATG is preceded by an in-frame termination codon TGA (nucleotide residues −12 to 9). The sequence flanking the assigned ATG (nucleotide residues −5 to 4) is a favored sequence for eukaryotic initiation sites (consensus; CCG/ACCATGG) described by Kozak (30). In fact, 8 out of 9 consensus sequences were identical to the sequences flanking to the assigned initiation codon. The codon specifying carboxy-terminal leucine is followed by the translational termination codon TGA (nucleotide residues 659–771). 4-1BB contains 1434 nucleotides of 3'-untranslated region which did not extend as far as polyadenylation signal nor the poly (A)$^+$ tail.

FIG. 2 shows the nucleotide sequence and the deduced amino acid sequence of 4-1BB. The nucleotides of the message strand are numbered in the 5' to 3' direction and numbers are shown on both sides of the sequence. Nucleotide residue 1 is the A of the initiation codon ATG, and the nucleotides on the 5' side of residue 1 are indicated by negative numbers. The predicted amino acid sequence is shown below the nucleotide sequence. Putative signal peptide is underlined. The potential asparagine-linked glycosylation sites are underlined. Potential polyadenylation signal is boxed. Stop codon is indicated by (- - -). Cysteine residues are highlighted by (.). An unusual feature of 4-1BB sequence is that there is a potential polyadenylation signal of AATAAA at nucleotides 1158–1163 (FIG. 2b boxed). It was believed that this signal was functional because this gene produces at least two different sizes of mRNA. We believe that this signal of AATAAA at nucleotides 1158–1163 (FIG. 2b boxed). We believe that this signal is functional because this gene produces at least two different sizes of mRNA. FIG. 3a and b shows RNS blot analysis of ConA-stimulated L3 RNA. When the blot was hybridized to L3G25#4 probe which contained sequences of 3' side to the polyadenylation signal (nucleotides 1284–1557). The probe detected one RNA species of approximately 2.4 kb. When the same blot was hybridized to L3G14#2 probe which contained sequences of 5' side to the first polyadenylation signal (nucleotides 661–855), the probe detected two mRNA species of approximately 1.5 kb and 2.4 kb.

FIG. 3 shows the expression of two different sizes of 4-1BB mRNA. Ten micrograms of poly(A)$^+$ mRNA from mouse B cell line (K46), TPA-stimulated EL-4 (EL-4 TPA) and rat NK cell line (LGL), and ten micrograms of total RNA from unstimulated L3 (L3) and concanavalin A-stimulated L3 (L3 ConA) were fractionated on a 1.4% formaldehyde agarose gel, transferred to GeneScreenPlus and hybridized to [$^{32}$P]-labeled L3G25#4 (a), L3G14#2 (b) and L3G20#3 (c) sequentially. L3G25#4 and L3G14#2 represent cDNA fragments of the 3' side and %' side to boxed AATAAA sequence, respectively.

L3G20#3 is an anonymous cDNA from L3 cDNA library and is used to show that each lane of the blot contains a similar amount of RNA. Positions of 28S and 18S rRNA markers are each indicated. Arrows indicate the specific hybridization signal.

The deduced sequence of the first 22 amino acids of 4-1BB has characteristics of the signal peptide of secretory and membrane-associated protein (27), which mainly contains hydrophobic amino acids. We putatively assigned the first 22 amino acids as a signal peptide. A possible cleavage site of the signal peptide is after glycine residue at alanine (FIG. 2b). Gly-ala at amino acidpositions 22 and 23 is one of the favorable signal peptidase cleavage sites(*). Thus the protein backbone of processed 4-1BB protein is composed of 234 amino acids with a molecular weight of 25,000. We found two potential asparagine-linked glycosylation signals (22,23) at amino acid positions 129 and 138 as underlined in FIG. 2b. The predicted 4-1BB protein contains unusually large numbers of cysteines. There are 23 cysteine residues in the putative mature protein as dotted in FIG. 2a.

There is a stretch of 26 amino acids that constitutes hydrophobic domain toward the carboxy terminus of the protein (amino acids at positions 182–211). Whether this region serves as a membrane-spanning domain is not known. This region is followed by the 45 amino acids which constitute a hydrophilic region.

Southern Blot Analysis. As shown in FIG. 4, fragments of L2G25B and 4-1BB cDNA each detect single restriction fragment of approximately 15 kb and 18 kb in both C57BL/6 and BALB/c, DNA, respectively. The data indicate that the genes encoding the two molecules exist as a single copy in C57BL/6 and BALB/c mice. FIG. 4 shows a Southern Blot analysis of mouse genomic DNA. Genomic DNA from C57BL/6 (lanes 1,3) and BALB/c (lanes 2,4) was digested with EcoRI restriction enzyme, fractionated on a 0.8% agarose gel, transferred to Gene- Screenplus and hybridized to [$^{32}$P] labelled L2G25B (lanes 1,2) and 4-1BB (lanes 3,4).

The protocol developed by the present inventor and reported and published as identified hereinabove for a modified differential screening of a cDNA library by which one can detect a broad representation of the mRNA expressed differentially in two different cell types, was applied to the systematic analysis of HTL and CTL gene expression and allowed us to isolate T cell subset specific genes. This approach offers an alternative to the classical protein purification for identifying molecules and genes. Advantages of this method are: 1) The approach identifies the existence of molecules which otherwise may be difficult or impossible to recognize or isolate; 2) Even molecules which exist at a low level in the natural source can be produced in quantity by recombinant DNA technologies and in turn provide enough protein to permit study of function and possibly clinical applications; and 3) It is a straightforward method for identifying mutations of the gene using the nucleic acid probe. As an illustration of the usefulness of this approach, the genes for T-cell antigen receptors and X-linked immunodeficiency (xid) genes were cloned and characterized in this fashion (31). This approach has already proven to be useful in isolating known as well as previously unrecognized T-cell mediators.

Using the same concanavalin A stimulated L2 cells, Prystowsky et at (32) identified 10 different lymphokine activities from culture supernatants; they include IL-2, IL-3 BCSF, CSF, IFN- and five unidentified factors which affect macrophage activities. In the course of the studies cDNAs were isolated and identified for IL-2, IL-3, CSF, T cell replacing factor and proenkephalins from the concanavalin A-stimulated L2 and cDNA library (2 and unpublished observations). Therefore, it was considered possible that L2G25B and 4-1BB represented the unidentified soluble mediators of Prystowsky et al which affect macrophage activities.

By applying a modified differential screening of L2 and L3 cDNA library, two novel T cell genes were isolated. Correlation of these T cell molecules with functional activities was shown by the following evidence. L2G25B was shown to code for a lymphokine and 4-1BB was shown to have similar activity, however, 4-1BB was later shown to be a receptor protein.

Figure 6A:
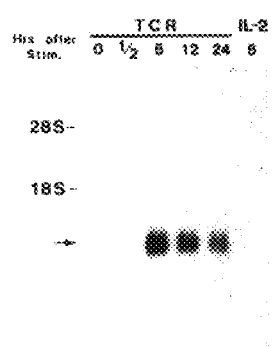
Figure 6B:
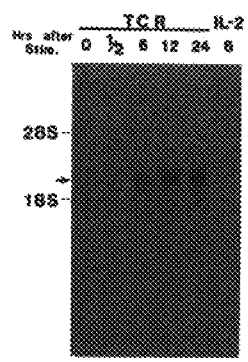

T-cell-specific expression of L2G25B and 4-1BB. L2G25B was isolated from an L2 cDNA library, and 4-1BB was isolated from and L3 cDNA library by the aforesaid modified differential screening (5). As shown in FIGS. 6a and 6b, L2G25B and 4-1BB were expressed preferentially in L2 and L3 cells only after concanavalin A stimulation. The sizes of transcripts were approximately 800 bases for L2G25B and 2400 bases for 4-1BB. The abundance of the two transcripts was 5~10 fold higher in L2 cells than in L3 cells. The two transcripts were not detectable in K46 B cells, EL-4 thymoma cells or rat large granular lymphocytes. L2G25B mRNA was consistently more abundant than 4-1BB mRNA. FIG. 5 shows T cell-specific expression of L2G25B and 4-1BB mRNA. Poly (A)$^+$ mRNA was prepared from mouse B cell line (K46), unstimulated EL-4 (EL-4), TPA-stimulate EL-4 (EL-4 TPA) and rat NK cell line (LGL), and total RNA was prepared from unstimulated L2 (L2), concanavalin A-stimulated L2 (L2 ConA), unstimulated L3 (L3) and concanavalin A-stimulated L3 (L3 ConA). Ten micrograms of total RNA or ten micrograms of poly(A)$^+$ RNA was fractionated on a formaldehyde/agarose gel, transferred to GeneScreenplus and hybridized to [P]-labelled L2G25B(a) and 4-1BB(b) sequentially. Positions of 28S and 18S rRNA markers are each indicated. An arrow indicates the specific hybridization signal.

L2G25B and 4-1BB mRNA were inducible by TCR stimulation, but not by Il-2 stimulation. The inducibility of the two cDNA clones was tested after L3 TCR stimulation by clonotypic antiTCR mAb, 384.5, or Il-2. As shown in FIGS. 6a and 6b, the expression of the two cDNA was inducible by TCR stimulation but not by Il-2 stimulation in L3 Cells. L2G25B mRNA was detectable at 0.5 hr after TCR stimulation, peaked at 6 hr, and decreased thereafter until at least 24 hr. 4-1BB mRNA was detectable at a very low level in unstimulated L3 cells in this experiment. The induction of 4-1BB mRNA occurred approximately 6 hr after TCR stimulation and remained level until 24 hr.

Figure 6C:
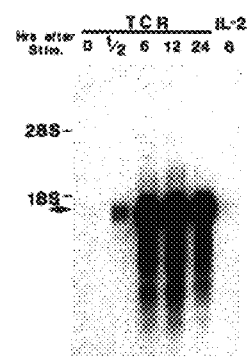
Figure 6D:
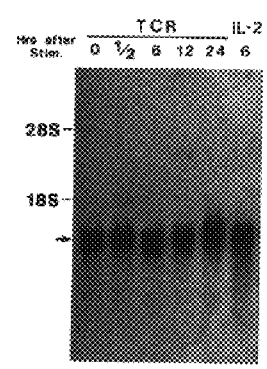

FIG. 6c shows the kinetics of IFN-δ mRNA expression in the same RNA blot as used in FIG. 6a and 6b. IFN-δ mRNA was detectable at 0.5 hr after TCR stimulation, peaked at 12 hr and declined slightly until 24 hr. There was a low level of IFN-δ mRNA in unstimulated L3 cells. When we compared the peak level of L2G25B and 4-1BB mRNA with that of IFN-δ mRNA, IFN-δ mRNA was at least 20 fold higher than that of L2G25B mRNA and a least 50 fold higher than that of 4-1BB mRNA. FIG. 6d demonstrates that all six lanes contained almost identical amounts of RNA. The probe was a serine protease cDNA (L3G10#6) isolated from L3 cells. In summary, the pattern of the two cDNA expression was similar to that of IFN-δ expression. FIG. 6 shows patterns of L2G25B and 4-1BB mRNA expression after TCR stimulation or IL-2 treatment. L3 cells were stimulated with clonotypic antiTCR mAb 384.5 for 0, ½, 6, 12 or 24 hr or with rIl-2 for 6 hr. Ten ug of total RNA was fractionated on a formaldehyde/agarose gel, transferred to GeneScreenplus and hybridized to [$^{32}$P]-labeled L2G25B(a) 4-1BB(b), IFN-δ (c) and L3G10#6(d) cDNA. L3G10#6 is a serine protease cDNA isolated from L3 cell cDNA library, which was identical to HF gene (24). L3G10#6 was used to show that each lane contains almost equal amounts of RNA. Positions of 28S and 18S rRNA markers are each indicated. An arrow indicates the specific hybridization signal.

L2G25B and 4-1BB mRNA are inducible by TCR stimulation in other cloned HTL, CTL and hybridomas. As shown in FIGS. 7a and 7b, L2G25B and 4-1BB mRNA are also inducible in HTL L2 and CTL dB45 after TCR stimulation with antiTCR mAb F23.1. The mRNA level for the two cDNA was also much lower than that of IFN-δ in L2 and dB45 cells (FIG. 7c). L2 cells show the highest level of expression of the three cell clones. FIG. 7 shows expression of L2G25B and 4-1BB mRNA in HTL L2 and a CTL dB45 cells. HTL L2 and CTL dB45 cells were stimulated with antiTCR mAb F23.1 for 6 hr. L3 cells were stimulated with anti TCR mAb 384.5 for 6 hr. Ten ug of total RNA from unstimulated L3 (lane a) and stimulated L3 (lane 2), unstimulated dB45 (lane 3), stimulated dB45 (lane 4), unstimulated L2 (lane 5) and stimulated L2 (lane 6) was fractionated on formaldehyde/agarose denaturing gel, transferred to GeneScreenplus and hybridized to [$^{32}$P] labeled L2G25B(a), 4-1BB(b), and IFN-δ (c) cDNA. A fraction of RNA in each lane was degraded and detected as RNAs in lower molecular sizes. 4-1BB mRNA was inducible by concanavalin A in two cytotoxic hybridomas, PN37 and Md90 (FIG. 8a) and detectable in unstimulated CTLLA11 CTL (FIG. 8b) clones.

FIG. 8 shows expression 4-1BB mRNA in concanavalin A-stimulated hybridomas PN37 and Md90, and in an unstimulated CTL CTLLA11. FIG. 8a shows BW5147, PN37 and Md90 cells were stimulated with concanavalin A for 4 hr. Ten ug of poly(A)$^+$ mRNA from unstimulated and stimulated each of these cells was fractionated, transferred to nitrocellulose filter and probed with [$^{32}$P]-labelled 4-1BB cDNA. FIG. 8b shows ten ug of poly(A)$^+$ mRNA from mouse melanoma cells (melanocyte) and ten ug of total RNA from unstimulated L2 (L2), CTLLA11 (A11) and L3 (L3) cells was fractionated, transferred to Gene-Screenplus and hybridized to [$^{32}$P] 4-1BB cDNA.

Figure 9A:
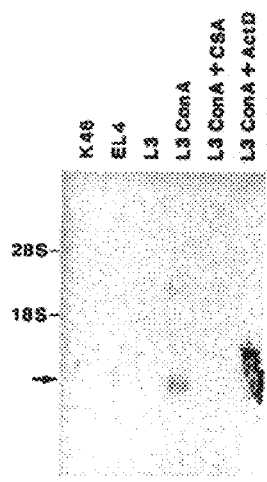
Figure 9B:
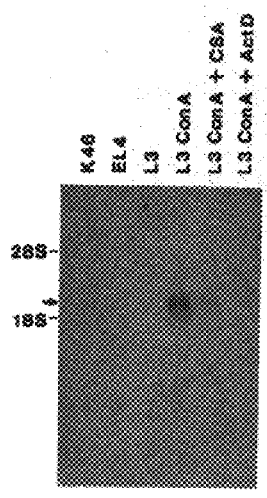
Figure 9C:
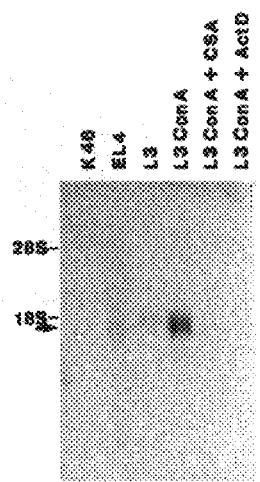
Figure 9D:
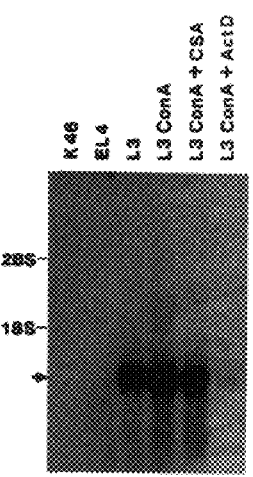

Effects of cyclosporin A on L2G25B and 4-1BB transcription. To test the possibility that the two cDNAs represent two different soluble extracellular mediators, we next examined the effect of cyclosporin A on RNA expression. Cyclosporin A inhibits mitogen or antigen-induced T-cell proliferation (33). It has also been shown to block the induction of expression of several lymphokine genes including 11-2 and IFN-δ ((34). The inhibition of lymphokine production occurs at a pretranslational level (35). In contrast cyclosporin A appears to have no effect on the inducible expression of c-fos and Il-2 receptor genes in T cells. As shown in FIGS. 9a and 9b, cyclosporin A inhibited the induced accumulation of L2G25B and 4-1BB mRNA. The same findings were seen with IFN-δ (FIG. 9c). A low level of expression of L2G25B mRNA was seen in TPA-stimulated El-4 cells in this experiment. FIG. 8d shows that cyclosporin A had minimal or no effect on the level of serine protease (probe, L3G10#6) mRNA and shows that the three lanes contained almost equal amounts of RNA (EL-4 or K46 cells did not express L3G10#6 mRNA). This data strongly suggested that L2G25B and 4-1BB expression would show some of the same activation requirements as other known lymphokines.

FIG. 9 shows the effect of cyclosporin A on L2G25B and 4-1BB mRNA expression. L3 cells were stimulated with concanavalin A, concanavalin plus cyclosporin A or concanavalin IA plus actinomycin D. Ten ug of total RNA from unstimulated L3(L3), concanavalin A-stimulated L3 (L3 ConA), concanavalin A plus cyclosporin A-treated L3 (L3 ConA+CsA) and concanavalin A plus actinomycin D-treated L3 (L3 ConA+ActD) cells and ten ug of poly(A) mRNA from K46 (K46) and TPA-stimulated EL-4 cells (EL-4) were fractionated, transferred to GeneScreenplus membrane and hybridized to [$^{32}$P] labelled L2G25B(a), 4-1BB(b), IFN-δ

(c) and L3G10#6(d) cDNA. Cyclosporin A treatment did not alter the level of L3G10#6 mRNA but almost completely abrogated the induced expression of other 4 mRNA species. An arrow indicates a specific hybridization signal.

L2G25B and 4-1BB mRNA were inducible in normal mouse spleen cells. To find out if the expression of these genes were not unique to certain cloned T cells or hybridoma cells, splenocytes from C57BL/6, and BALB/c mice were stimulated with concanavalin A and tested for mRNA expression. As shown in FIGS. 10a and 10b the two mRNA were detectable after concanavalin A stimulation in C57BL/6 and BLAB/c mouse splenocytes. They were also inducible in Swiss Webster mouse splenocytes (data not shown). As shown in FIG. 9c IFN-δ mRNA was detectable in concanavalin A-stimulated BALB/c splenocytes (for unknown reasons IFN-δ mRNA was not detectable in concanavalin A-stimulated C57BL/6 splenocytes in this experiment). RNA preparations for Figure c were different from those for Figures a and b. This data suggested that these molecules could be induced in normal mouse spleen cells by appropriate stimulii as in the cloned T cells.

FIG. 10 shows the expression of L2G25B and 4-1BB mRNA in mouse splenocytes. Splenocytes were obtained from C57BL/6 and BALB/c mice and stimulated with concanavalin A for 14 hr. Ten ug of total RNA from unstimulated BALB/c (lane 1) and stimulated BALB/c (lane 2), unstimulated C57BL/6 (lane 3) and stimulated C57BL/6 (lane 4) splenocytes was fractionated, transferred to Gene Screen plus end hybridized to [$^{32}$P]-labelled L2G25B(a), 4-1BB(b) and IFN-δ (c) cDNA. A portion of L3G29 cDNA (approximately 200 pairs in the middle of the molecule) consistently detected an additional RNA species of approximately 1500 bases. The additional hybridization signal is seen in FIG. 10b.

L2G25B and 4-1BB share properties which suggested that they encode soluble T cell mediators. The properties are; 1) the mRNA of the two was preferentially expressed in T cells; 2) The mRNAs of the two genes were present in undetectable amount in T cells until induced by concanavalin A, or by TCR stimulation; 3) The small size of the mRNA of L2G25 was consistent with features of several analyzed lymphokine cDNAs such as interleukins 2,3 and 5; 4) The patterns of expression were very similar to that of the lymphokine IFN-δ; 5) Both had a potential signal sequence and an AT rich 3' untranslated region consistent with a lymphokine gene (28) and 6) Cyclosporin A inhibited the induced mRNA expression corresponding to the two cDNAs. Using the same concanavalin A stimulated L2 cells, Prystowsky et al (32) identified 10 different lymphokine activities from culture supernatants; they included IL-2, IL-3, BCSF, CSF, T cell replacing factor and proenkephalins from our concanavalin A-stimulated L2 cDNA library (5 and unpublished observation). Therefore, L2G25B and 4-1BB were considered as possible candidates for the unidentified soluble mediators of Prystowsky et al which affected macrophage activities.

Isolation of human lymphokines and receptors homologous to L2G25B and 4-1BB. L2G25B and 4-1BB cDNA may be used as probes to isolate human lymphokines or receptors homologous to these type clones. Each cDNA will be radio-labeled and hybridized to human genomic DNA blot under various stringency and washing conditions using standard laboratory techniques known to those skilled in the art.

The species difference in nucleotide sequences between human and mouse will determine the degree of homology by clone hybridization experiments. On the determination of the optimal hybridization and washing conditions under which the probes detect a signal in the human genomic DNA blot, then a human genomic library in lambda vector may be screened with radio labeled L2G25B and 4-1BB. The hybridizing human clones may then be isolated and the nucleotide sequences determined.

The genomic human clone corresponding to mouse clone L2G25 and 4-1BB may then be used as a probe to survey human T cells which express mRNA by RNA blot analysis. When the human T cells which express the RNA homologous to L2G25B and 4-1BB are discovered and isolated, the RNA may then be used to construct a cDNA library. Then the cDNA library may be screened with the human genomic clone corresponding to L2G25B and 4-1BB and isolate the human cDNA clones corresponding to L2G25B and 4-1BB.

Plasmid p4-1BB may be used to grow the receptor 4-1BB. To do so: one must insert the cDNA of 4-1BB into an appropriate prokaryotic or a eukaryotic expression vector such as a Bovine Papilloma virus expression vector; and transfecting that expression vector into mouse fibroblasts or other appropriate transfection hosts; and grow the then transfected mouse fibroblasts in an appropriate culture media; and then purifying the lymphokine protein from the culture media.

cDNA in the form of plasmid p4-1BB in Ecoli NM 522 has been deposited at the American Type Culture Collection under ATC No: 67825 and will be available after this Patent Application issues.

An Inducible Receptor-like Molecule, 4-1BB, is Expressed in Infiltrating Mononuclear Cells of Diabetic NOD Mice The transcript of 4-1BB was inducible by concanavalin A in mouse splenocytes, T-cell clones, and hybridomas. The expression of 4-1BB transcripts was inhibited by cyclosporin A. The 4-1BB mRNA was inducible by antigen receptor stimulation but was not inducible by Il-2 stimulation in the cloned T-cells (91). The 4-1BB cDNA encodes a peptide of 256 amino acids containing a putative leader sequence, a potential membrane anchor segment, and other features of known receptor proteins. Therefore, the expression pattern of 4-1BB resembles those of lymphokine mRNAs while the sequence appears consistent with those of receptor proteins.

The deduced amino acid sequence of 4-1BB is similar to tumor necrosis factor receptor (92). The 4-1BB protein is also a member of the nerve growth factor receptor super family, for the deduced amino acid sequence of 4-1BB predicts a cysteine-rich extracellular domain (93). Shaw et al. (94) mapped the amino acid sequence involved in the p56$^{lck}$ binding in the cytoplasmic domains of $T_4$ and $T_8$ antigens. The 4-1BB protein contains the consensus amino acid sequence which can bind to the p56$^{lck}$ in the putative cytoplasmic domain.

The primary purpose of the research reported herein was to further develop our understanding of the biological function of this molecule. In this context, an antiserum was prepared which recognizes the 4-1BB protein and determined the protein expression in various tissues of normal and pathologic mice.

As a diseased tissue, the pancreas of the diabetic NOD mouse was chosen for study. The NOD mouse has become an important model of Type I, or insulin-dependent diabetes mellitus (36, 37, 95). In both humans and NOD mice, an autoimmune pathogenesis is suggested by the presence of lymphocytic infiltrations in the pancreatic islets that appear to result in selective β-cell destruction (96). The infiltrating T-lymphocytes appear to be activated by triggering agents, possibly auto-antigens, upon infiltration into the pancreas. As a step to further understanding the biological functions of this molecule, the possibility that 4-1BB is expressed in the infiltrating mononuclear cells in the pancreatic islets of NOD mice was explored.

MATERIALS AND METHODS

Cells. CTLL-R8, a mouse cytolytic T-cell line, (97) was grown in DMEM (Gibco Laboratories, Grand Islands, N.Y.) containing 100 units/ml of penicillin, 100 μg of streptomycin, 4 units/ml of rIL-2 (Boehringer-Mannheim, Indianapolis, Ind.) and 10% FBS. RAW 264.7, a murine macrophage cell line (38–42), and EL-4, a mouse thymoma cell line were cultured in DMEM, containing 10% FBS, 25 mM Hepes, 1 mM sodium pyruvate, 100 units/ml of penicillin and 100 μg/ml of streptomycin. COS-1 cells were grown in DMEM containing 10% FBS, 100 units/ml of penicillin, and 100 μg/ml of streptomycin.

Antibody Preparation. Five oligopeptides representing different regions of the deduced 4-1BB protein (4-1BBP) sequence were synthesized (Applied Biosystems, Foster City, Calif.). Two sequences, named 4-1BB-0 and 4-1BB-11, stimulated the production of antibodies. The amino acid sequence of the oligopeptide 4-1BB-0 was a 12-mer from amino acids 105–115 of the deduced 4-1BBP. Oligopeptide 4-1BB-11 was a 25-mer from amino acids 133–157 of the deduced 4-1BBP. A tyrosine residue at the C-terminus of the oligopeptide 4-1BB-0 was added for labeling with $[^{125}I]$ if needed. The peptides were conjugated to keyhole limpet hemocyanin (KLH) using a heterobifunctional cross linker, m-maleimidobenzoyl-N-hydroxysuccinimide ester (98).

Rabbits were immunized with peptide-KLH (100 μg per dose) emulsified in Freund's complete adjuvant. The rabbits received one intracutaneous injection in 4 foot pads and one intramuscular injection two weeks apart. After two weeks, the rabbits received three consecutive intravenous injections (50 μg per dose) without adjuvant. The serum was obtained 5 days after the final injection, and the titer was measured by ELISA using the peptide as the antigen.

Flow Cytometry. $1\times10^7$ CTLL-R8 cells were incubated with preimmune or IgG fraction of anti-4-1BB-rabbit serum on ice for 30 min. Cells were washed three times in RPMI 1640 containing 5% FBS. Then the cells were incubated on ice for 30 min with fluorescein isothiocyanate (FITC)-conjugated goat anti-rabbit immunoglobulin. The cells were washed again with phosphate buffered saline (pH 7.4) containing 10% bovine serum albumin. Flow cytometry was performed using an EPICS 753 (Coulter) fluorescence-activated cell sorter.

Immunocytochemistry and Histology. The cells were cultured on sterile cover slides coated with poly-L lysine. For some experiments, CTLL-R8 cells were stimulated with concanavalin A (5 μg/ml) for various lengths of time. The cells on coverslips were washed three times with phosphate-buffered saline (PBS), pH 7.4, for 5 min and fixed by treating with 3.7% formaldehyde in PBS at room temperature for 10 min and with methanol at −20° C. for 4 min. Subsequently, the cells were treated with acetone at −20° C. for 1 min.

To prepare nonpathologic tissue slides, C57B1/6 mice were perfused with 4% paraformaldehyde in PBS through the heart. After perfusion, organs were excised and cut in blocks of 1–2 mm thickness. The organs included the brain, heart, lung, thymus, liver, spleen, pancreas, and kidney. These tissue blocks continued to be fixed in 4% paraformaldehyde for 24 hrs. The tissue blocks were further cut with a vibratome into slices of 40 μm thickness. Lung specimens were cut with a cryostat after being frozen in Tissue-Tek O.C.T. (Miles Scientific, Naperville, Ill.).

Streptavidin-biotinylated alkaline phosphatase complex (ABC-Ap) (DAKO Corporation, Denmark) was used to stain cells or frozen sections of lung. A positive reaction was indicated by red staining with a fast red. Horseradish peroxidase-antiperoxidase (PAP) was used to stain the vibratome sections of other organs. The anti-4-1BB-0 rabbit serum was used as primary antibodies and pre-immune rabbit sera were used as controls. Meyer's hematoxylin or methyl green was used for counter staining.

To study the immuno-cytochemistry of the NOD mouse pancreas, the pancreas was fixed in Carnoy's B solution (75% ethanol and 25% glacial acetic acid) and was processed to make a paraffin block. The paraffin sections were deparaffinized, rehydrated in graduated alcohols and immersed in PBS, while frozen sections were used after fixation in cold acetone. Appropriately diluted antibodies were incubated with the sections for 3 hrs at room temperature, followed by washing in PBS for 5 min and incubation with FITC-labeled protein A (1:40 diluted in PBS with 0.05% Evan's blue) for another 3 hrs at room temperature. Pictures were taken with an Olympus BH-2 fluorescent microscope. Parallel with immunofluorescence staining, the sections were stained with hematoxylin and eosin, allowing the grading of insulitis to be scored as described elsewhere (99).

NOD Mouse. The colony of NOD mice was obtained from the Second Department of Internal Medicine, Kobe University School of Medicine, Kobe, Japan. These animals were maintained on regular mouse chow and tap water ad libitum at the University of Calgary. At the age of 10 weeks, the 5 NOD mice were treated with cyclophosphamide (Horner, Montreal, Quebec, Canada) at the dose of 150 mg/Kg body weight twice at 3-day intervals. At the age of 26 weeks, they were sacrificed and pancreata were excised.

Immunoblot Analysis. Cells grown in petri dishes were washed in PBS and lysed by adding TNE buffer (50 mM Tris HCl, pH 8.0, 1% NP-40, 2 mM EDTA) on ice for 2 hrs. The TNE buffer contained the protease inhibitors aprotinin and leupeptin at 100 μg/ml each. The cell lysate was harvested and centrifuged for 5 min. The supernatant containing approximately 1 mg/ml of protein was denatured by boiling for 2 min in a sample buffer consisting of 62.5 mM Tris HCl, pH 6.8, 10% glycerol, 1% SDS, 1% β-mercaptoethanol and 0.001% bromphenol blue. The proteins were resolved on 12% SDS-PAGE (polyacrylamide gel electrophoresis) and transferred electrophoretically onto an Immobilon membrane (Millipore, Bedford, Mass.). The membranes were blocked to prevent nonspecific antibody binding by incubating in 5% nonfat dry milk in TBST (50 mM Tris HCl, pH 7.4, 0.15 M NaCl and 0.05% Tween-20) for 1 hr at room temperature. The membranes were then treated with primary antibodies or primary antibodies treated with oligopeptides at room temperature for 1 hr. After four washes with TBST, the membranes were incubated with a secondary antibody against rabbit IgG(H+L) —alkaline phosphatase conjugate (Zymed, Inc., S. San Francisco, Calif.) at 1:100 dilution as recommended by the manufacturer. The rabbit antiserum absorbed by an oligopeptide was prepared as follows. The rabbit antiserum was incubated with various concentrations of the oligopeptide (0, 0.1, 1.0, and 10 μg/ml) in TBST buffer and 1% dry nonfat milk, then microcentrifuged at 14,000 rpm for 20 min, and the supernatant was used as a primary antibody after further dilution in TBST.

The reactive bands were visualized by incubating the membrane with chromogenic substrates, p-nitroblue-tetrazolinum chloride (NBT) and 5-bromo-4-chromo-3-indolyl-phosphate (BCIP) (Bio Rad, Richmond, Calif.) in 0.1 M Tris, pH 9.5, 0.1 M NaCl, and 5 mM $MgCl_2$.

Construction of the Expression Plasmid of Truncated 4-1BB. The putative extracellular domain of 4-1BB cDNA was amplified by polymerase chain reaction (PCR) (100). An Xho1 site was created at the 5' end of the forward primer and a stop codon, (TAA), and an Eco R1 site were created in the reverse primer. The PCR product was digested with Xho1 and Eco R1 and the ~0.6 kb fragment was purified. The Xho1-Eco R1 fragment (P4-1BBs) was inserted into the PXM vector (101).

Production of the Recombinant Truncated 4-1BB Protein. COS-1 cells were grown to 30–50% confluency and were transfected with the truncated 4-1BB in the PXM vector using the DEAE dextran method (102). Forty-four hours post transfection, the culture medium was replaced with serum-free medium (Opti MEM, Gibco Laboratories, Grand Island, N.Y.). The culture medium was harvested twice every 24 hrs. The proteins in the conditioned medium were precipitated with 4 volumes of acetone at −20° C. and resuspended in a mixture consisting of a chromatography buffer (50 mM Tris, pH 7.4, 0.15 M NaCl and 0.05% Tween −80), 5M urea and 1% β-mercaptoethanol. After the removal of undissolved particles by brief microcentrifugation, the supernatant was subjected to Sephadex G-200 chromatography. The fractions that were reactive with rabbit anti-4-1BB-0 antiserum in Western blot analysis, were pooled. The truncated, thus soluble 4-1BB protein (4-1BBPs) was further enriched through fractionation with Q-Separose column (Pharmacia Fine Chemicals) with a linear gradient of Nacl from 0.0 to 1.0 M. The amino-terminal sequence of 4-1BBPs was determined by an automatic peptide sequencer PI 2090 (Proton Instrument, Tarzana, Calif.) after the protein was transferred to Immobilon-p (Millpore, Bedford, Mass.).

Northern Blot Analysis. Mouse organs were sliced into 1 mm thick pieces. A portion of each organ was stimulated by incubating in DMEM containing PMA (phorbol 12-myristate 13-acetate, 20 ng/ml) for 24 hrs. A portion of the spleen was treated with concanavalin A (10 µg/ml) in DMEM. The remaining portion of each organ was incubated in DMEM plus 10% FBS without PMA or concanavalin A for 24 hrs. The tissues were frozen in −70° C. and pulverized in liquid nitrogen before extracting RNA. RNA was extracted from the tissues and cells by the guanidinium-phenol extraction procedure (103). The RNA was fractionated on a 1.4% formaldehyde denaturing agarose gel, transferred to a Gene-Screen Plus membrane, and hybridized to $^{32}$P-labeled probes.

RESULTS

Specificity of Antioligopeptide Antisera to 4-1BB and Expression of 4-1BB Protein. The only information previously available on the 4-1BB was the nucleotide sequence of the cDNA and the predicted amino acid sequence. In order to study the 4-1BB protein (4-1BBP), polyclonal antibodies were raised against oligopeptides representing five different portions of the predicted 4-1BBP. To aid in proving that the putative antisera contain antibodies which uniquely recognize the 4-1BBP, a search for cell lines that express 4-1BB mRNA was made. CTLL-R8 cells produced a high level of 4-1BB mRNA while a macrophage cell line, Raw 264.7, or unstimulated EL-4 cells did not produce detectable amounts of 4-1BB mRNA (FIG. 11). FIG. 11 shows the expression of 4-1BB on RNA in CTLL-R8. Cytoplasmic RNA was prepared from mouse CTL line, CTLL-R8 (lane A), macrophage cell line, RAW 264.7 cells (lane B) and unstimulated EL-4 cells (lane C). Ten micrograms of total RNA was fractionated on a formaldehyde/agarose gel, transferred to a Gene Screen Plus, and hybridized to 4-1BB cDNA probe. Arrows indicate the specific signals. Positions of 28S and 18S rRNA markers are indicated.

We then tested whether any of the antibodies recognized the three cell lines differentially. Two antisera among five tested had a positive reaction to CTLL-R8 cells while the antibodies did not stain RAW 264.7 or EL-4 cells. One anti-oligopeptide antiserum, anti-4-1BB-0, stained CTLL-R8 cells at a higher dilution (1:1600) than did the other one, anti-4-1BB- 11. The staining pattern of CTLL-R8 cells revealed a diffuse granular distribution in the cytoplasm and uniform staining on the cell membrane (data not shown). When the lysates of CTLL-R8, RAW 264.7 and EL-4 cells, were prepared and an immunoblot analysis performed with the anti-4-1BB-0 serum, a unique band of 40 kD was recognized in the CTLL-R8 cells but not in the RAW 264.7 or EL-4 cells (FIG. 12).

FIG. 12 shows an immunoblot analysis of CTLL-R8 cell lysates with anti-4-1BB-0 serum. Lanes A and B contain approximately 20 µg of CTLL-R8 cell lysate. Lanes C and D contain approximately 20 µg protein of RAW 264.7 and EL-4 cell lysate, respectively. Lane A reacted with preimmune rabbit serum. Lanes B, C and D reacted with anti-4-1BB-0 serum (1:1600). The arrow indicates the 40 kD protein band on Lane B.

To prove further the specificity of the antioligopeptide antisera, an expression plasmid was prepared containing a truncated 4-1BB cDNA. The membrane anchor and cytoplasmic domains were eliminated from the 4-1BB cDNA. The truncated cDNA was inserted into the PXM vector and expressed in COS-1 cells. The culture medium of the transfected COS-1 cells was concentrated and fractionated by Sephadex G-200 chromatography. An aliquot of each fraction was run on SDS-PAGE, transferred to the Immobilon membrane (Millipore, Bedford, Mass.), and treated with the anti-oligopeptide antiserum, anti-4-1BB-0. A peak of protein was found which reacted with the anti-4-1BB-0. There was no detectable amount of the 4-1BBP in the COS-1 cell lysate. The soluble 4-1BBP (4-1BBPs) fraction was further purified through Q-sepharose column. The molecular size of the 4-1BBPs was approximately 23 kD on a 10% SDS-PAGE.

Next, a series of immunoblots was prepared containing the 4-1BBPs. The blots were stained with unabsorbed or absorbed anti-4-1BB-0 antiserum. FIG. 13 shows an immunoblot analysis of the 4-1BBPs. Lanes A, B, C, and D contain the cell culture supernatant of COS-1 cells which were transfected with truncated 4-1BB expression plasmids. Lane A reacted with unabsorbed anti-4-1BB-0 serum. Lanes B to D reacted with anti-4-1BB-0 serum absorbed by 0.1 µg/ml (lane B), 1 µg/ml (lane C) and 10 µg/ml (lane D) of the 4-1BB-0 peptide. The arrow with the 23 kD indicates the bands seen on lanes A and B. FIG. 13, lane A, shows the 4-1BBPs band (23 kD) from the COS-1 cell medium reacted with anti-4-1BB-0. The 4-1BBPs band gradually disappeared when the anti-4-1BB-0 was absorbed by the increasing amount of the oligopeptide 4-1BB-0. As shown in FIG. 13, lane B, the antibodies to the 4-1BB protein were not absorbed completely by 0.1 µ/ml of the 4-1BB-0 peptide. However, when the concentration of 4-1BB-0 was increased to 1.0 µg/ml (lane C) and 10 µg/ml (lane D), the anti-4-1BB-0 antibodies were completely absorbed, showing no 4-1BBPs bands.

The amino-terminal sequence of the purified 4-1BBPs was determined. The sequence was Val-Gln-Asn-Ser-X-Asp (SEQ ID NO:6). The amino acid sequence at positions 1, 2, 3, 4 and 6 was identical to that of the mature 4-1 BBP predicted from the cDNA sequence. Amino acid at position 5 which is supposed to be Cys was not determined. These results indicate that the deduced amino acid sequence and assignment of signal sequence are correct. When the potential transmembrane domain was removed from the complete 4-1BB molecule, the protein was secreted. These results suggested that 4-1BBP was likely to be associated with the cellular membrane as predicted by the primary structure.

The 4-1BBP expression was analyzed by flow cytometry and cell sorting using an EPICS 753 fluorescence-activated cell sorter (Coulter). FIG. 14 shows representative histograms of IgG fraction of anti-4- 1 BB-O related fluorescence intensity of CTLL-R8 cells. X-axis represents fluorescence intensity and Y-axis, cell numbers. A: Unsorted CTLL-R8 cells stained with IgG fraction of anti-4-1BB-O. B and C: The stained population in A was separated from the rest of the cells, cultured for 8 days, and stained with either preimmune (B) or IgG fraction of anti-4-1BB-O (C). Flow cytometry and cell sorting were performed with an EPICS 753 fluorescence-activated cell sorter (Coulter).

Figure 14A:
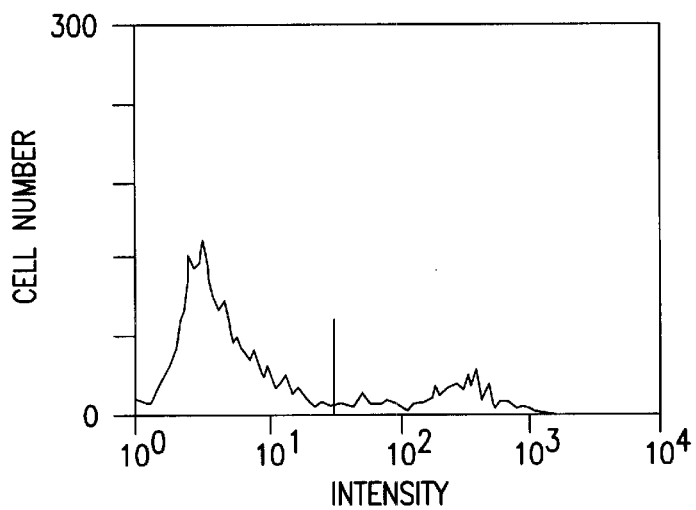
Figure 14B:
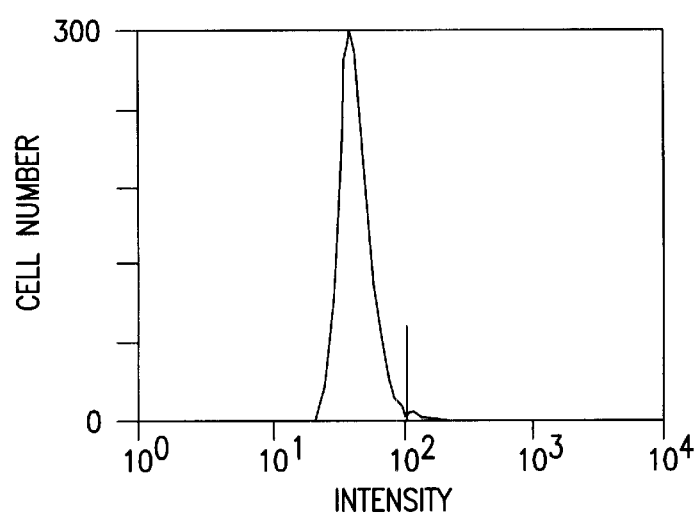
Figure 14C:
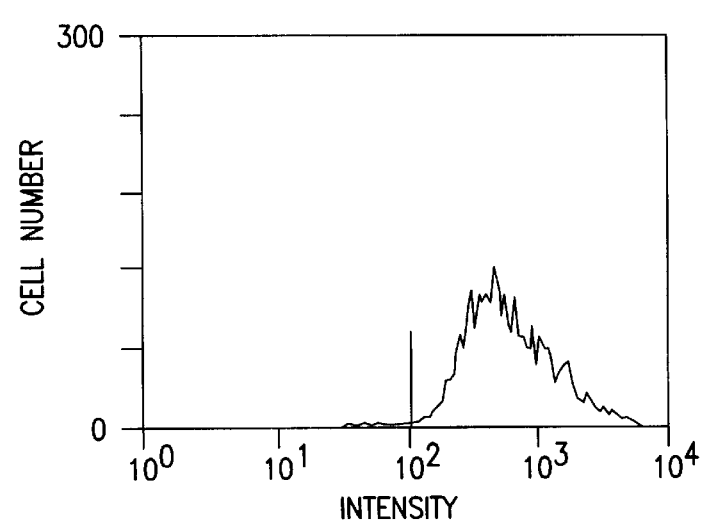

When the CTLL-R8 cells were stained with IgG fraction of the anti-4-1BB-O rabbit serum, approximately 21% of the cells were labeled (FIG. 14A). Next, a sort for the 4-1BB$^+$ cells was performed and these cells were cultured in the presence of 20 units/ml of rIl-2. These cells were cultured for 8 days before testing 4-1BBP expression by flow cytometry again. When these cells were stained with anti-4-1BB-O serum, 98.3% of this cell population was labeled (FIG. 14C), while preimmune serum stained the cells at background level (FIG. 14B). These results indicated that the 4-1BB protein was expressed on the cell surface and perhaps represented a receptor.

The Tissue Distribution of 4-1BB. RNA was extracted from tissues of various organs and tested for the expression of 4-1BB mRNA. 4-1BB mRNA was detected in the spleen, kidney, and heart; but no RNA was detectable in the liver, adrenal gland, or pancreas. The RNA level was markedly elevated when the spleen and heart were treated with PMA, but other organs did not show 4-1BB RNA induction after PMA treatment (FIG. 15).

FIG. 15 shows the expression of 4-1BB RNA in mouse tissues. The total RNA from the spleen (lanes A, B, and C), heart (lanes D and E), and kidney (lanes F and G), was fractionated on formaldehyde-denaturing agarose gel, transferred to Gene Screen Plus, and hybridized to a $^{32}$P-labeled 4-1BB cDNA probe. Each lane contains 20 µg of RNA. Lane A: unstimulated spleen RNA, lane B: concanavalin A-stimulated spleen RNA, lane C: PMA-stimulated spleen RNA, lane D: unstimulated heart RNA, lane E: PMA-stimulated heart RNA, lane F: unstimulated kidney RNA, and lane G: PMA-stimulated kidney RNA. Positions of 28S and 18S rRNA markers are indicated. An arrow indicates the specific hybridization signal.

The 4-1BBP was detected in the medullary tubules and medullary rays of the kidney (data not shown). A small number of mononuclear cells in the alveolar septae of the lungs and some lymphocytes in the spleen showed weak staining. The pancreas, liver, testes, and ovary expressed neither 4-1BB mRNA nor 4-1BBP. The detailed description of tissue distribution of the 4-1BBP will be published elsewhere.

4-1BB Expression in Infiltrating Mononuclear Cells. In serial sections of the pancreata, 40 islets were observed after hematoxylin-eosin staining. FIG. 16 shows the histology of NOD mouse pancreata and immunofluorescent staining of islets showing different stages of insulitis. Pancreas sections of A, C, and E were stained with the standard hematoxylin and eosin staining technique, while those of B, D, and F were stained with anti-4-1BB-0 serum and FITC-conjugated protein A. B, D, and F are the corresponding islets to A, C, and E, respectively. A and B: early-stage insulitis, C and D: intermediate-stage insulitis, and E and F: late-stage insulitis. Note the strong immunofluorescent staining in the mononuclear cells at the periphery of islets showing the early stage of insulitis, while the staining is not apparent in the islets showing the late stage of insulitis.

Among those islets, 10 showed no insulitis and 12 showed signs of early insulitis in which lymphocytes had infiltrated only to the periphery of each islet (FIG. 16A). The remaining 18 islets showed intermediate or late stage insulitis in which the lymphocytes had infiltrated into the islets and showed signs of islet destruction (FIGS. 16C and 6E). The serial sections were then stained with anti-4-1BB-0. None of the 10 intact islets showed 4-1BB expression (Table 3). However, mononuclear cells accumulated at the periphery of the islets were stained with the anti-4-1BB-0 serum in the early stage of insulitis (FIG. 16B). All 12 of the early insulitis islets demonstrated the same staining pattern (Table 3). 4-1BB expression diminished gradually in the mononuclear cells during the intermediate to late stages of insulitis (FIGS. 16D and 6F). Seven of the 18 islets of intermediate to late stage insulitis showed weak staining in the infiltrating mononuclear cells, and the remaining 11 islets showed no staining. These results indicate that the 4-1BB protein is most likely associated with T-cell functions during the early phase of activation. Such an early expression of 4-1BB protein is well corroborated with the finding that 4-1BB mRNA was detectable as early as 30 min after the T-cells are stimulated with lectins or antibodies to T-cell receptors.

TABLE 3

Expression of the 4-1BB protein in the insulitis lesion of NOD mice according to the grade of insulitis.

| Stage of Insulitis | No. | 4-1BB Expression | | |
| --- | --- | --- | --- | --- |
| | | Strong | Weak | None |
| Intact islets | 10 | 0 | 0 | 6 |
| Early | 12 | 12 | 0 | 0 |
| Intermediate/Late | 18 | 0 | 7 | 11 |

The insulitis lesion was arbitrarily classified as early, intermediate, and late-stage insulitis according to the morphological criteria as follows. Early insulitis was defined as an accumulation of mononuclear cells at the periphery of or just within the islet. In intermediate insulitis, the mononuclear cells infiltrated the center of the islets but left the architecture of the islets relatively well-preserved. In late insulitis, the architecture of islets was distorted, and infiltration by mononuclear cells was markedly increased. The expression of the 4-1BB protein was scored as strong, weak or none. The strong expression indicates that more than 50% of the infiltrating mononuclear cells were positive (FIG. 15B), while weak expression means only a few cells were positive (FIG. 15D).

DISCUSSION

The 4-1BB cDNA was isolated based upon its preferential expression in T-cells. These experiments demonstrated that 4-1BB is expressed constitutively in renal medullar cells and that expression is induced in the spleen and heart by PMA treatment. In the spleen, T-cells are likely to respond to PMA or concanavalin A and are probably responsible for the increase of 4-1BB mRNA. However, it is not known which cells in the heart respond to PMA to produce 4-1BB mRNA.

The earlier studies showed that the protein backbone of the natural 4-1BBP is composed of 233 amino acids with an Mr of 25 kD. This protein therefore must undergo an extensive post-translational modification to be 40 kD protein. The deduced 4-1BBP contains both N- and O- glycosylation sites. Occasionally anti-4-1BB-0 serum recognizes 38 and 34 kD extra bands, which were believed to represent 4-1BBP with different degrees of glycosylation. The protein backbone of truncated 4-1BB is composed of 162 amino acids with an Mr of 18 kD. Since the truncated form produced by COS-1 cells resolves at 23 kD, this form of 4-1BB also undergoes post-translational modification. In fact, when the 4-1BBPs were produced in baculoviral expression system 4-1BBPs constituted three bands of 18 kD, 20 kD and 23 kD which, are believed to represent 4-1BBPs with different degrees of glycosylation (unpublished observation).

The primary structure of 4-1BB, the flow cytometric analysis of 4-1BBP expression, and the secretion of 4-1BBPs indicate that the 4-1BBP is associated with the cellular membrane. Why a certain population of CTLL-R8 cells expressed 4-1BB constitutively was not known. Perhaps a group of cells changed its properties during the long in vitro maintenance. CTLL-R8 was a cloned CTL which lost killing activity in the course of in vitro maintenance.

To determine more about the functions of this receptor-like molecule, it was decided to find the ligands. The truncated, thus secretory and soluble, 4-1BBPs have been value in determining the function of 4-1BB. It was postulated that if the 4-1BBPs competed for the membrane form of 4-1BB with the specific ligand, the 4-1BBPs might function as a specific inhibitor.

It was believed that the infiltrating mononuclear cells which are stained by anti-4-1BB-0 antibodies are activated T-lymphocytes because only splenocytes stimulated with Con A or anti-TCR antibody expressed 4-1BB mRNA. Detailed studies on the surface markers of infiltrating cells that are stained by anti-4-1BB-0 antibodies were underway. It is interesting that 4-1BBP is expressed in the early phase of insulitis and disappears when T-cells infiltrate into islets. It was postulated that 4-1BBP might be a receptor which transduces signals from the membrane to the nucleus necessary for the immediate early phase of inflammation or antigen recognition. This is in contrast to the expression of other molecules such as perforin (104). Perforin, a potential molecule for tissue damage (91), is produced when T-cells infiltrate the islets. The expression of perforin in the early stage of insulitis was almost undetectable (unpublished observations).

The dynamic functions of T cells in a successful immune system are accomplished through mediators which are produced when T cells are activated. These mediators are in the form of cell surface receptors and soluble secretory molecules. Identification of new mediators and the demonstration of their functions can lead to the discovery of unknown functions of T cells and to the development of ways to manipulate the immune system in the treatment of disease.

Expression of a Novel T-cell Molecule, 4-1BB. in the Brain

The responses of both the immune and nervous systems to environmental change are mediated by soluble secretory proteins and receptors. Although, to date few biological molecules which are shared by these systems have been identified, the linking of the immune and nervous systems has been the focus of much speculation and had stimulated widespread interest.

A series of T-cell subset-specific cDNAs were cloned from cloned helper and cytolytic T-lymphocytes by employing a modified differential screening procedure. The transcript of one of the clones, 4-1BB, was detected in the T-lymphocytes when the T-cells were activated by either an antigen receptor stimulation or concanavalin A (Con A). This induced expression was inhibited by cyclosporin A. The predicted 4-1BBP contained an unusually large number of cysteins. These residues were arranged with a spacing similar to those in several groups of proteins including the epidermal growth factor receptor. The potential 4-1BB sequence showed similarities with the sequences of the tumor necrosis factor receptor and the nerve growth factor receptor (97). The receptor feature of 4-1BB and the resemblance to the nerve growth factor receptor prompted us this investigation with the brain. Using Northern blot analysis of mRNA and immunocytochemistry for detecting 4-1BB protein (4-1BBP), and it was unexpectedly found that the 4-1BB protein has a high and constitutive expression in the brain, an organ which contains abundant receptor elements and is ontogenically separate from the immune system. The following report deals with the expression of 4-1BB in the nervous system and focuses on its distribution in the brain and in the peripheral nerves.

METHOD & MATERIALS

Northern Blot Analysis. Mouse organs were sliced into pieces of 1 mm thickness, and a portion of each organ was incubated in PMA (Phorbol Myristic Acetate, 20 ng/ml) containing Dulbecco's minimum essential medium (DMEN, GIBCO) and 10% fetal bovine serum (FBS) for 24 hrs. A portion of spleen was treated with ConA (10 $\mu$g/ml) in DMEM and 10% FBS. The remaining portion of each organ was incubated in DMEM and 10% FBS without PMA or ConA for 24 hrs. The tissues were frozen at −70° C. and pulverized in liquid nitrogen before extracting RNA. RNA was extracted from the tissues and cells by guanidium-phenol extraction procedure (86, 87). The RNA was fractionated on a 1.4% formaldehyde denaturing agarose gel, transferred to a Gene Screen Plus membrane, and hybridized to a $^{32}$P-labeled 4-1BB cDNA probe.

Antibody Preparation. An oligopeptide representing amino acids 105–115 of the deduced 4-1BBP sequence was synthesized (Applied Biosystems). The sequence was NH$_2$—CRPGQELTKSGY—COOH (SEQ ID NO:7). A tyrosine residue at the C-terminus of the peptide was added for possible radioactive labeling with [$^{125}$I]. The peptide was conjugated to keyhole limpet hemocyanin (KLH) with a [heteroblifunctional] heterobifunctional cross linker, m-maleimidobenzoyl-n-hydroxysuccinimide ester (88, 107). was NH$_2$—CRPGQELTKSGY—COOH. A tyrosine residue at the C-terminus of the peptide was added for possible radioactive labeling with [125I]. The peptide was conjugated to keyhole limpet hemocyanin (KLH) with a heteroblifunctional cross linker, m-maleimidobenzoyl-n-hydroxysuccinimide ester (88, 107).

Rabbits were immunized with peptide-KLH (100 $\mu$g/dose) emulified in Freund's Complete adjuvant. In two week intervals they received one intracutaneous injection in each of four foot pads and one intramuscular injection. After two weeks, the rabbits received three consecutive I.V. injections without adjuvant. The serum was obtained five days after the final injection and the titer was measured by ELISA using peptide as the antigen. The specificity of these antibodies to 4-1BBP (anti 4-1BB-O) was shown in pervious studies.

Immunocytochemistry. the procedure for immunocytochemistry was published previously (108). In brief, C57B1/6 mice were perfused with formaldehyde made fresh intracardially under deep anesthesia from 4% paraformaldehyde and 0.1 M phosphate-buffered saline (PBS). Brains and muscle from the gluteal region were then removed, left in the same fixative overnight, and sliced into 40 um sections for immunocytochemical staining. The 4-1BB (1:200) antiserum was used for positive staining, and antiserum preabsorbed with 4-1BB (10 $\mu$g/ml) was used as control. The Sternberger's peroxidase-anti-peroxidase (PAP) indirect-enzyme method was used for staining. The PAP reaction was done with 0.003% $H_2O_2$ and 0.05% 3'3-diaminobenzidine. The primary and secondary antibodies were diluted with PBS containing 0.2% Triton-X100 and 1% normal sheep serum. The primary antibodies were incubated overnight and the secondary antibodies were incubated for one hour. Rabbit antiserum against purified mouse laminin (E.Y. Labs, San Mateo, Calif.) was used as a control antiserum.

RESULTS

Similarity of 4-1BBP to other Known Proteins. The 4-1BBP shows a similarity to the nerve growth factor receptor, the tumor necrosis factor receptor, CD40, and the Shope fibroma virus T2 proteins as described by Smith et al (97). A search was made for the proteins which contain regions similar to those of 4-1BBP and found two other potential proteins which were encoded by seven in absentia (sina) and by DG17. Sina genes are required by the R7 photoreceptor cell of the Drosophila eye for correct R7 cell development (109). The N-terminal cysteine-rich region of the sina protein is extensively similar to the 4-1BBP (FIG. 17) and is also similar to the protein product of the Dictyostelium DG17 gene, whose expression is specifically induced during aggregation by cAMP (110).

FIG. 17 shows a comparison of the 4-1BBP amino acid sequence with the amino acid sequence in sina of Dorsophila and DG17 of Dictyostelium. The amino acids which are shared are boxed. Numbers represent the positions of the left-most residues relative to the N-terminus. Gaps (-) are introduced to allow for maximal alignment.

This region forms the pattern of C-X,-C-X$_9$-H-X$_3$C-X-C (SEQ ID NO:8); and the cysteines and histidine are conserved in a similar space in 4-1BB, sina, and DG17 proteins. Ten of 24 amino acids between the 4-1BB and sina proteins are identical. Between 4-1BB and DG17 proteins, 11 of 24 amino acids are identical, and 3 of 24 are conservative substitutions. The conserved pattern suggests that these amino acids are functionally important.

4-1BB mRNA Expression. As shown in FIG. 18, 4-1BB RNA was detected in the brain (lanes A and B), and heart (lanes C and D)_and the spleen (lanes G, H. and I) while 4-1BB RNA was not detected in the pancreas (lanes E and F). FIG. 18 shows a northern blot analysis of kidney and brain RNA. Total cytoplasmic RNA from brain (A and B), heart (C and D) and spleen (E,F, and G) were fractionated on 1.2% formaldehyde denaturing agarose gel and hybridized to [$^{32}$P]-labeled 4-1BB cDNA probe. Lane A: unstimulated brain RNA; Lane B: PMA-stimulated brain RNA; Lane c: unstiumlated heart RNA; Lane D: PMA-stimulated heart RNA; Lane E: unstiumlated spleen RNA; Lane F: PMA-stimulated spleen RNA, and Lane G: ConA-stimulated spleen RNA. Positions of 28S and 18S are indicated by 28 and 18, respectively. The arrow I indicated 4-1BB RNA from brain and the arrow II indicates 4-1BB RNA from spleen and heart.

4-1BB RNA was inducible in the heart and the spleen (lands D and H) by PMA, and by ConA in the spleen (lane I), but was not inducible in the brain. The size of the Brain 4-1BB RNA (FIG. 18, Arrow II) is smaller than that of 4-1BB RNA's from other tissues (FIG. 18, Arrow I). In addition, the mRNA level in the brain is lower than that in other tissues. Such a result is surprising since this protein is detected at a high level in the brain. This may indicate that the 4-1BB m RNA has a long half-life and may undergo several rounds of translation.

Immunocytochemistry: a) General distribution of 4-1BB immunoreaction in the brain. Brain tissue (FIGS. 19 and 20) exhibited the most intense 4-1BB immunoreactive staining of all tissue examined, including liver, kidney, and muscle. Generally, dark staining products are densely distributed in the gray matter where neuronal soma, dendrite, and fiber terminals reside (FIG. 18). Except the neuronal soma and distinct fiber bundles, most of the gray matter was stained. In the brain region, where only glial cells accumulate, no staining was identified. Thus, definitive localization of 4-1BB-like protein in the brain was strictly limited to the gray matter. No staining was observed in the major fiber bundle such as corpus callosum, cingulum bundle, internal capsule bundle, fimbria-fornix, medial longitudinal fascicularis, or medial forebrain bundle.

FIG. 19 shows 4-1BB immunostaining in the cortex (a,b, and d) striatum (a,d, and e) at progressively enlarged magnifications. 4-1BB staining is seen in the majority of gray matter but is absent in neuron and glial cell bodies, white matter, and in fiber bundles (see corpus callosum, CC in a, and internal capsules, IC and d and e). Granular shape of 4-1BB staining (arrows) is seen around the neuronal bodies (stars in c and e) but not around glial bodies within fiber bundles (d and e). The 4-1BB positive granules in the striatum (e) resemble the dopamine terminals.

FIG. 20 shows distinct 4-1BB immunopositive reaction in the cerebellum at three progressively enlarged magnifications (a,b, and c). The 4-1BB positive reaction is most intense in molecular layer (M), lighter on Purkinje layer (P), and forms glomerulus-like patches (arrows) in the granular layer (G). It is generally absent in the cell bodies of Purkinje, granular layer (G). It is generally absent in the cell bodies of Purkinje, granular neurons, and glial cells. It is completely absent in axons in the fiber bundle in the white matter (W). The majority of the 4-1BB stainings are accumulated in the terminal regions, where synapsis occurs. It was negatively stained when the antiserum was preabsorbed with antigen, 4-1BB peptide (d). Scales: a=200 um, b,d,=100 um, and c=30 um.

High magnification (100x oil lens) of light microscopic photographs showed that these distinctly stained 4-1BB immunoreactive products are granular in shape with a size of 0.46–0.55 um. These 4-1BB granules seem to reside among neurons and on the surface of neuronal soma (FIG. 19) and perhaps also on the dendrites/proximal axons. The density of the 4-1BB-like granules varies from region to region, and density distribution is often coincident with that of neuronal fiber terminals. The most intense 4-1BB positive staining was see in the striatum and closely resembles dopamine-fiber terminals in the straitum (FIGS. 19$d,e$).

Immunocytochemistry: b) Specific Regions. Unique distribution of 4-1BB-like staining was observed in a number of brain regions. In the cortex, 4-1BB-like granules were packed in the molecular layer and were distributed with sparse accumulation in layers II to VI (FIGS. 19a,b,c). They were relatively homogeneous among layers except in the frontal cortex, where a band of dense immunoreaction was located in layer IV, and in the temporal cortex, where a dense but relatively narrower band was located within the molecular layer (not shown).

The most densely distributed immunoreactive granules were in the striatum (FIG. 19d) and in the molecular layers of the cortex (FIGS. 19a,b,c), hippocampus, and cerebellum (FIG. 20). In the cerebellum, the staining pattern was unique in that the 4-1BB-like granules were densely packed in the molecular layer, loosely distributed in the Purkinje layer, accumulated as islands in the sea of granules and Golgi cells in the granular layer, and were almost blank in the fiber bundle area (FIGS. 20a,b,c, and d). The 4-1BB-like granules formed islands and did not seem to border cell bodies as seen in other brain regions. The morphology strongly resembled the glomerulus in the cerebellum. The similar island-like accumulation of 4-1BB-like immunoreactive granules also existed in the nucleus of the stria medularis (not shown).

DISCUSSION 4-1BB, although expressed constitutively in the brain, is produced in the t_cells only when t-cells are activated; therefore, the main site of in-vivo function may be the brain and not T-lymphocytes. Such a common expression of 4-1BBP may provide a clue to the communication pathway between the immune and nervous systems. 4-1BBP contains a putative zinc finger structure of the yeast elF-2B protein (57) and shared a conserved region with the sina and DG17 proteins. The sina protein is localized in the nucleus, suggesting that it has a regulatory function in cells. The 4-1BBP has been detected at the cellular membrane, cytoplasm, and the nuclear membrane (unpublished observation). The fact that the amino acid sequence of 4-1BB contains features like a zinc finger motif, a nuclear protein, and a receptor domain may indicate that 4-1BB can commute from the cell surface to the nucleus. Determining the ligand of 4-1BBP and its functions is, therefore, critical to further defining the functions of 4-1BBP.

The reasons for that the size of brain 4-1BB RNA is smaller than that of 4-1BB RNA from other tissues are not known. It is possible that brain expresses in RNA species similar to 4-1BB sequence, not the 4-1BB gene transcripts. The brain molecules detected by anti-4-1BB-O antibodies, therefore, may well be a cross-reacting protein which contains certain antigen epitopes similar to those of 4-1BBP. Nevertheless, the identification of the brain molecule detected by anti-4-1BB-O antibodies would be important because of the unique patterns of expression.

The mRNA expression and abundant immunostaining of 4-1BB-like protein in the brain indicate that 4-1BB is actively expressed and constitutes a significant component of the brain. Such abundant expression is not seen in the muscle or liner. Much of the evidence indicated that 4-1BB can be a receptor or nerve terminal in the brain and peripheral nervous system: a) morphological examination of the immunostain shows that the 4-1BB-like protein is located in the gray matter, particularly in the regions of dendrites, fiber terminals, and around the cell body of the brain, while being almost entirely absent from the white matter where synapses do not occur; b) the granule-shape morphology resembles the fiber terminals of GABAergic neurons on the substantial nigra, dopaminergic neurons on striatum, and synapsin, a synaptic membrane specific protein in the brain; c) while generally absent in the neuronal body and completely absent in and around glial cells, the protein was densely accumulated in many terminal regions of the brain; d) variable densities in regions such as cerebellum, striatum, and cortex coincided with dense fiber terminals; e) peculiar rosette patterns in the cerebellum and stria terminalis morphologically resembled the glomerulus, a specific synaptical complex in the cerebellum.

Recently, two neurotrophic factors, brain-derived neurotrophic factor (BDNF) (57), and neurotrophin-3 (NT-3) (112), were identified in addition to the nerve growth factor (NGF). These three factors closely resembled one another with 57 of the 119 residues (48%) are shared by all three proteins. Six cysteines found in these factors were absolutely conserved, and the regions of greatest similarity were mainly clustered around these cysteine residues. If BDNF and NT-3 utilize their own receptors, the receptor might have similar structural properties to NGF receptor. The structural similarity of 4-1BB to the NGF receptor allowing a suspicion that 4-1BBP actually encodes one of such known or yet unknown neurotrophic factors.

Inducible T Cell Antigen 4-1BB: Analysis of Expression and Function 4-1BB is an inducible receptor-like protein expressed in both cytolytic and helper Th cells. The 4-1BB mRNA was expressed in PMA-treated spleen and heart with constitutive expression detected in the kidney. The optional induction of 4-1BB mRNA required both PMA and ionomycin stimulation indicating that protein kinase C activation and increases in intracellular $Ca^2$ were required for its expression. 4-1BB was categorized as an early activation gene since the protein synthesis inhibitor, cycloheximide, blocked the induction of 4-1BB mRNA. A monoclonal antibody, 53A2, was prepared against recombinant soluble 4-1BB and used to characterize this molecule. 4-1BB was a 30 kDa glycoprotein and appeared to exist as both a monomer and a 55 kDa dimer on the cell surface. The 4-1BB protein may be post-translationally modified since its predicted backbone is 25 kDa. FACS analysis indicated that 4-1BB was inducible and expressed on the cell surface of activated splenic T cells and thymocytes. Crosslinking of 4-1BB on anti-CD3-stimulated T cells with 53A2 resulted in a dramatic enhancement of T cell proliferation. This suggests that 4-1BB may function as an accessory signaling molecule during T cell activation.

Recently, a number of cysteine-rich receptor proteins have been described and named as the nerve growth factor receptor (NGFR) super-family. (92) At present, the members of the NGFR super-family include NGFR (45); B cell antigen CD40 (46); the MRC OX-40 antigen (47), which is a marker of activated T cells of the CD4 phenotype; two receptors for tumor necrosis factor (TNF) called TNFR-I and TNFR-Il, which are found on a variety of cell types (48,91); SFV-T2 (121); an open reading frame (ORF) in the Shope fibroma virus which later was identified as a virally-encoded, soluble form of TNFR-I; a T cell surface antigen, CD27, which may be involved in T cell activation (49); Fas, a cell surface antigen that can mediate apoptosis (50); and Sal F19R, an ORF in the Shope sarcoma virus (51), as well as 4-1BB, which is the most distantly related member. The newest member is CD30, a Hodgkin's lymphoma antigen which may play a role in tile regulation of cellular growth and transformation (52). Members of the family are characterized by the presence of three to six patterns of cysteine-rich motifs which consist of about 40 amino acids in the extracellular part of the molecule. These molecules contain a hinge-like region immediately adjacent to the transmembrane domain. This region is characterized by a lack of Cysteine residues and a high proportion of Ser, Thr and Pro, which are likely to be glycosylated with 0-linked sugars.

4-1BB contains other interesting features in its cytoplasmic domain. Those include 1) two runs of acidic amino acids; 2) a potential $p_{56}^{lck}$ binding site; 3) five consecutive glycines at the carboxyl terminus; and 4) four potential phosphorylation sites - 1 tyrosine, 2 threonine, and 1 serine. It is especially interesting that 4-1BB contains a potential $p56^{lck}$ binding site, -C-R-C-P- (SEQ ID NO:9). The consensus sequence of $p_{56}^{lck}$ binding site is -C-X-C-P- (SEQ ID NO:10) in the CD4 and CD8 molecules (93).

To further understand the biologic function of 4-1BB, a mAb, 53A2, was prepared which recognizes the 4-1BB molecule. This reagent was used to characterize biochemical and expression properties of 4-1BB as well as assess the role of 4-1BB signaling in T cells.

MATERIALS AND METHODS

Cells

CTLL-R8 a mouse cytolytic T-cell] line, was grown in DMEM (Gibco Laboratories, Grand Islands, N.Y.) containing 100 units/ml of penicillin, 100 pg/ml of streptomycin, four units/ml of rIL-2 (Boehinger-Mannheim, Indianapolis, Ind.) and 10% fetal bovine serum (FBS). F1 is a CD4+, I-A$^d$ reactive T cell-clone which was generously provided by Dr. Scott Bryson, University of Kentucky. This clone was isolated from DBA/2 mice that had syngeneic graft-versus host disease. The clone was maintained in PRMI 1640 (Gibco Laboratories) containing 10% FBS, 50micromoles 2-ME, and antibiotics (coplete medium). Rat Con A supernatent was added at 30%. Spadoptera frugiperda (Sf-21), an insect cell line was grown in synthetic serum free medium, Ex-cell 400 (JRH Biosciences) containing antibiotics at 27° C. (53).

Preparation of Splenic T Cells

The resting murine splenic T cells were enriched by nylon wool and Percoll gradient centrifugation (54, 55). Briefly, the spleen cells of female Balb/c mice (Harlan, Indianapolis, Ind.) were adjusted to 1.5×10$^8$/ml in RPMI 1640 containing 2% fetal bovine serum (FBS). A 10 ml nylon wool column was prewashed with phosphate buffered saline, pH 7.4 (PBS) followed by RPMI 1640 containing 2% FBS, and incubated at 37° C. for 20 min before use. The spleen cells were loaded onto the column and incubated at 37° C. for 30 min. The column was washed with the above medium. The eluted cells subsequently were fractionated by centrifuging the cells at 2000×g at 4° C. for 30 min or 50–100% Percoll step gradient. The resting T cell fraction was recovered from the interface between the 50% and 80% Percoll. The enrichment of T cells were examined with EPICS Profile Analyzer (Coulter Corporation); ~91% were Thy 1.2$^+$, ~52% were L3T4$^+$ and ~24% were Lyt 2$^+$. These cells were resting since they exhibited a uniform low degree of forward angle light scatter.

Thymocyte Preparation

Thymuses from 6–8 week old Balb/c mice were aseptically removed and teased into a cell suspension. Thymocytes were washed twice in RPMI 1640 containing 2% fetal bovine serum (FBS).

Production of Recombinant 4-1BB Protein in Sf-21 Cells

To construct a plasmid that expresses extracellular portion of 4-1BB, the putative extracellular domain of 4-1BB cDNA (89) was amplified by polymerase chain reaction (PCR) (99). An XhoI site was created at the 5' end of the forward primer and a stop codon, (TAA), and an EcoRI site were created in the reverse primer. The PCR product was digested with XhoI and EcoRI and the ~0.6 kb fragment was purified. The XhoI-EcoRI fragment (4-1BBS) was inserted into the PEV-55 vectors (53), generating PEV-55–4-1BBS. The sequence of the forward primer (SEQ ID NO:11) was 5'-ACCTCGAGGTCCTGTGCATGT-GACA-3' and that of the reverse primer (SEQ ID NO:12) was 5'-ATGAATTCTTACTGCAGG-AGTGCCC-3'. primer. The PCR product was digested with XhoI and EcoR1 and the ~0.6 kb fragment was purified. The XhoI-EcoR1 fragment (4-1BBS) was inserted into the PEV-55 vectors (53), generating PEV-55–4-1BBS. The sequence of the forward primer was 5'-ACCTCGAGGTCCTGTGCATGT-GACA-3' and that of the reverse primer was 5'-ATGAATTCTTACTGCAGG-AGTGCCC-3'.

To express the entire 4-1BB protein, 1.2-kb cDNA fragment (4-1BBL) that contains all the coding sequence of 4-1BB was inserted in the EcoR1 site of PVL 1392 vector (a kind gift from Dr. Max Summers), generating PVL 1392-4-1BBL.

4-1BBS as well as 4-1BBL were transferred from these plasmids to Autographa Californica nuclear polyhedrosis virus (ACNPV) genome by cotransfection into Sf-21 cells as described (53), Ten occlusion-negative viruses for each construct were plaque-purified. AcNPV-4-1BBS and AcNPV-4-1BBL recombinant viral stocks were grown in Sf-21 cells in serum-free Ex-cell 400 medium.

Rabbit Polyclonal Antiserum Against 4-1BB Oliopeptides

Five oligopeptides representing different regions of the deduced 4-1BB protein (4-1BBP) sequence were synthesized (Applied Biosystems, Foster City, Calif.). Two sequences, named 4-1BB-0 and 4-1BB-11, stimulated the production of antibodies. The amino acid sequence of the oligopeptide 4-1BB-0 was a 12-mer from amino acids 105–115 of the deduced 4-1BBP (89). Oligopeptide 4-1BB-11 was a 25-mer from amino acids 133–157 of the deduced 4-1BBP (2). A tyrosine residue at the C-terminus of the oligopeptide 4-1BB-0 was added for labeling with [$^{125}$I] if needed. The peptides were conjugated to keyhole limpet hemocyanin (KLH) using a heterobifunctional cross linker, m-maleimidobenzoyl-N-hydroxysuccinimide ester (97).

Rabbits were immunized with peptide-KLH (100 pg per dose) emulsified in Freund's complete adjuvant. The rabbits received one intracutaneous injection in each of 4-foot pads and one intramuscular injection two weeks apart. After two weeks, the rabbits received three consecutive intracutaneous injections (50 μg per dose) without adjuvant. The serum was obtained 5 days after the final injection, and the titer was measured by ELISA.

Purification of the rs-4-1BBP

The serum-free culture supernatants of Sf-21 cells infected by AcNPV-4-1BBS were concentrated by ammonium sulfate precipitation (60% saturation). The precipitate was dissolved in a buffer containing 40 mM Tris-HCl (pH 7.8), 50 mM NaCl and 0.02% NaN$_3$ and dialyzed in the same buffer. The sample was subsequently fractionated by Sephacryl S-300 in the above buffer. The fractions containing 4-1BBS were identified by Western blotting with anti-4-1BB-0 antibodies. rs-4-1BBP containing fractions were pooled and concentrated by vacuum dialysis. The sample was again fractionated by Q-Sepharose, an anion exchange column chromatography. rs-4-1BBP-containing fractions were pooled, dialyzed against 5 mM sodium phosphate buffer pH 7.2 and were further fractionated by hydroxylapatite column. Finally, the rs-4-1BBP-containing samples were equilibrated with 50 mM sodium phosphate buffer (pH 7.2) and loaded on Sepharose. A linear gradient from 0 to 0.5 M NaCl was used to elute absorbed proteins. The rs-4-1BBP-containing fractions were pooled and concentrated by vacuum dialysis.

Production of Anti-4-1BB mAb

Eight week-old Sprague-Dawley rats were immunized with 50 μg of rs-4-1BBP emulsified in Titermax (cytRX). (subcutaneously) twice at a two-week interval. A third (intracellular) injection was given two weeks after the last immunization. Three days after the final injection the rat spleen was removed. Spleen cells were fused with SP2/0 mouse myeloma cells and cultured according to the standard method (56). ELISA was used to screen for the rs-4-1BBP-reacting clones. Seventeen clones were isolated and subcloned. One clone 53A2 (IgG$^1$) was characterized and is disclosed herein. The monoclonal antibody was purified from culture supernatant by affinity chromatography on protein G-Sepharose (Schleicher-Schnell).

Immunoblot Analysis

Cells were washed in PBS and lysed by adding TNE buffer (50 mM Tris HCl, pH 8.0, 1% NP-4–0, 2 mM EDTA) on ice for 2 hrs. The TNE buffer contained the protease inhibitors, aprotinin and leupeptin at 100 μg/ml each. The cell lysate was harvested and centrifuged at 10,000×g for 10 min at 4° C. The supernatant containing approximately 1 mg/ml of protein was denatured by boiling for 2 min in a sample buffer consisting of 62.5 mM Tris HCl, pH 6.8, 10% glycerol, 1% SDS, 1% β-mercaptoethanol and 0.001% bromphenol blue. The proteins were resolved on 12% polyacrylamide gel with SDS and transferred electrophoretically onto an Immobilon membrane (Millipore, Bedford, Mass.). The membranes were blocked to prevent nonspecific antibody binding by incubating in 5% nonfat dry milk in TBST (50 mM Tris HCl, pH 7.4, 0.15 M NaCl and 0.05% Tween-20) for 1 hr at room temperature. The membranes were then treated with primary antibodies at room temperature for 1 hr. After four washes with TBST, the membranes were incubated with a secondary antibody against rabbit or rat IgG (H+L)-alkaline phosphatase conjugate (Zymed, Inc., S. San Francisco, Calif.) at 1:100 dilution. The reactive bands were visualized by incubating the membrane with chromogenic substrates, p-nitrobule-tetrazolinum chloride (NBT) and 5-bromo-4-chromo-3-indolyl-phosphate (BCIP) (Bio Rad, Richmond, Calif.) in 0.1 M Tris, pH 9.5, 0.1 M NaCl, and 5 mM MgCl$_2$.

Immunoprecipitation of Cell Surface 4-1BB

F1 cells were labeled with [$^{35}$S] cysteine (Amersham), at a concentration of 0.1 mCi/ml for 14 hr in a cysteine-free RPMI 1640 and 5% dialyzed-FBS. Normal and anti-CD3-stimulated F1 cells were washed twice with PBS and resuspended in PBS containing 0.2% BSA and 0.1% NaN$_3$. To detect the cell surface 4-1BB antigen, cells were first incubated with 10 tg of 53A2 or unrelated rat IgG$_1$ (Zymed) at 4° C. for 1 hr. The cells were then recovered, washed and lysed in a lysis buffer (20 mM Tris.HCl, pH 7.4, 140 mM NaCl, 1% digitonin, 1 mM sodium vanadate, 5 μg/ml aprotinin and 1 μg/ml leupeptin) on ice for 15 min. The 4-1BB and 53A2 complexes were precipitated by rec-protein G Sepharose-4B (Zymed). The immunoprecipitates were run on 10% SDS-polyacrylamide gel and exposed to X-ray film after soaking the gel in EN$^3$HANCE (NEN).

Flow Cytometry

Cells (0.5×10$^6$/sample) were incubated with in RPMI 1640, 1% BSA, and 0.1% sodium azide with purified 53A2 on ice for 30 min. Cells were washed three times in RPMI 1640 containing 5% FBS. The cells were then incubated on ice for 30 min with fluorescein Isotiliocyanate (FITC)-conjugated goat anti-rat immunoglobulin. Some samples received FITC-conjugated goat anti-rat Ig only. The cells were washed again with phosphate buffered saline (pH 7.4) containing 10% bovine serum albulnin. Flow cytometry was performed using an EPICS 753 (Coulter) Florescence-activated cell sorter.

Northern Blot Analysis

Thymocytes or spleen T cells were stimulated with anti-CD3 MAb (clone 145-2C11), ionomycin PMA (Calbiochem, La Jolla, Calif.), 10 ng/me PMA (Sigma, St. Louis, Mo.), or ionomycin plus PMA. Individual wells of 96-well flat bottomed culture plates or T25 Flasks (Costar, Cambridge, Mass.) were coated with 10 micrograms/ml anti-CD3 in PBS, pH 7.0 for 3 hours at 37° C. and the washed thress times with PBS. For RNA extraction, 2 to 3×10$^7$ cells at 5×10$^6$/ml were stimulated in complete medium and harvested at the indicated time points. Total RNA was extraceted by the guanidinium-phenol extraction procedure (102). The RNA was fractionated on a 1.4% formaldehyde denaturing agarose gel, transferred to a Gene-Screen Plus membrane, and hybridized $^{32}$P labeled probes.

RESULTS

In order to study the 4-1BB protein (4-1BBP), polyclonal antibodies were raised against oligopeptides representing five different portions of the predicted 4-1BBP. To aid in proving that the putative antisera contain antibodies which uniquely, recognize the 4-1BBP, an expression plasmid was contructed contining the putative extracellular portion of 4-1BB cDNA. The trancated cDNA was expressed in a baculoviral expression system. The antibodies were tested to see if any recognized the recombinant soluble 4-1BBP (rs-4-1BBP) in the Sf-21 cell culture medium. Two antisera among five tested recognized a protein found only in the supernatant of 4-1BBS infected cells. One anti-oligopeptide antiserum, anti-4-1BB-0, stained the band at a higher dilution (1:1600) than did the other one, anti-4-1BB-11. Rs-4-1BBP was purified from Sf-21 cell culture medium.

As shown in FIG. 21 (arrows), anti-rs-4-1BBP-reacting bands were detected of approximatley 18, 20, and 23 kDa (FIG. 21: Lane 1, Coomassie blue staining; lane 2, anti-4-1BB-0 antibody staining, and lane 3, molecular size marker). Partial amino acid sequences of each of the three bands were determined. The sequences of the 3 bands were identical and were Val-Gln-Asn-Ser-X-Asp. The amino acid sequence at positions 1, 2, 3, 4 and 6 was identical to that of the mature 4-1BBP predicted from the cDNA sequence. Amino acid at position which was supposed to be Cys was not determined. Also, rs-4-1BBP could be immunoprecipitated by 53A2, an anti-4-1BB monoclonal antibody. Production of the three different sizes of rs-4-1BBP is most likely due to the differences in glycosylation. These results indicate that the deduced amino acid sequence and assignment of signal sequence were correct. When the potential transmembrane domain was removed from the complete 4-1BB molecule, the protein was secreted, which is consistent with the full length 4-1BBP being associated with the cellular membrane as predicted by the primary structure.

Biochemical Properties of 4-1BB

Full length 4-1BB cDNA (4-1BBL) was expressed, in Sf-21 cells using recombinant baculoviruses containing 4-1BBL. The cell lysates were fractionated on a 10% SDS polyacrylamide gel and transferred to Immobilon-P. The blot was incubated with 53A2, an anti-4-1BB monoclonal antibody, and stained with goat-anti-rat IgG-conjugated alkaline phosphatase.

FIG. 22 shows recombinant 4-1BB protein. Full length 4-1BB cDNA (4-1BBL) was expressed in insect cells (sf 21) using recombinant baculoviruses containing 4-1BBL. The cell lysates were fractionated on a 10% SDS polyacrylamide gel, transferred to Immobilon-p and stained with 53A2, an anti-4-1BB mAb. The monomer of 4-1BB in reducing conditions consists of three major species whose sizes are 29, 30 and 31 kDa (lane 2). Non-reducing conditions (lane 4-) produced dimerized 4-1BB whose sizes are 49 to 60 kDa. Some of 4-1BB molecules are monomerized in lane 4, showing both monomers and dimers. Lane 1, uninfected Sf 21 cell lysate; lane 2, 4-1BBL-infected Sf2l cell lysate; lane 3, MIP-1β-infected Sf21 cell lysate (unrelated to 4-1BBL); lane 4,4-1BBL-infected Sf 21 cell lysate.

Under reducing conditions, the 4-1BB monomer consisted of three major species corresponding to 29, 30 and 31 kDa (FIG. 22, lane 2). Under non-reducing conditions, 4-1BB existed as a monomer as well as a dimer of 49 to 60 kDa. The heterogeneity in size may be due to different amounts of glycosylation as seen in rs-4-1BBP (FIG. 21).

FIG. 23 shows an immunoprecipitation of cell surface 4-1BB protein synthesized by T lymphocytes. T cell (F1 clone) surface 4-1BB protein was immunoprecipitated with anti-4-1BB mAb 53A2 (lanes 2 and 4) or with rat IgG$^1$ control mAb (lanes 1 and 3). Lanes 1 and 2 were run under reducing conditions and lanes 3 and 4 were run under nonreducing conditions. Monomeric form of 4-IBB protein is indicated by all arrowhead with number 1. The dimeric and tetrameric forms are indicated by the arrowheads with numbers 2 and 3, respectively.

4-1BBP expressed on T Iylnpliocytes was immunoprecipitated with the mAb 53A2. A CD4$^+$ T cell clone F1 was labeled with [$^{35}$S]cysteine. The mAb 53A2 (FIG. 23, lanes 2 and 4) or rat IgG$^1$ control (FIG. 23, lanes 1 and 3) antibodies was first incubated with F1 cells to bind to surface 4-1BBP. The cells were subsequently washed to remove unbound antibody, lysed, and immunoprecipitated wihl protein G-conjugated Sepharose beads. Under reducing conditions, 53A2 immunoprecipltated a 30-kDa protein (FIG. 23, arrow 1 ) and under non-reducing conditions, 53A2 immunoprecipitated 30-kDa (FIG. 23, arrow 1), 55-kDa (FIG. 23, arrow 2 ) and 110 kDa (FIG. 23, arrow 3) proteins. These three bands may represent monomer, dimer and tetramer species, respectively. Whether all these three forms of 4-1BBP exist in the T cell membrane and are in a dynamic equilibrium is not known. The most abundant form appears to be the dimeric 4-1BB.

Expression of 4-1BBP in Splenic T Cells and Thymocytes

Splenic T cells were isolated by a nylon wool column and a percoll gradient. The T cells were stimulated with 10 μg/ml of immobilized anti-CD3 mAb. T cells were harvested at various time points and tested for 4-1BB mRNA expression by Northern blot analysis, As shown in FIG. 24, 4-1BB mRNA was detected by 3 hrs of stimulation. Northern analysis also indicated that 4-1BB mRNA was not expressed in LPS-activated B cell blasts or in A20 cells, a B cell lymphoma (data not shown).

FIGS. 24a and 24B show that 4-1BB mRNA expression in induced murine splenic T cells by anti-CD3-activation. Splenic T cells were isolated by a nylon wool column and a percoll gradient (cells were isolated at the 60–70% interface) and stimulated over time with 10, μg/ml of immobilzed anti-CD3 (145–2C11) in the presence of accessory cells. Cyltures were harvested at indicated time points and monitored for 4-1BB expression by Northern analysis. Each lane contains 20 μg of total RNA. Northern blot was hybridized with a 4-1BB cDNA probe (23a) and the gel was stained with ethidium bromide prior to transfer as a control for equal loading of each lane.

Thymocytes were stimulated with ionomycin, PMA or ionomycin plus PMA and tested for 4-1BB mRNA expression. As shown in FIG. 25, 4-1BB mRNA was inducible by ionomycin or PMA. Both ionomycin and PMA, however, were required for optional expression of 4-1BB mRNA, indicating that 4-1BB mRNA expression requires protein kinase C activation and increases in intracellullar $Ca^{2+}$.

FIG. 25 shows that optimal induction of 4-1BB mRNA requires both Protein Kinase C activation and increases in intracellular $Ca^{2+}$. Thymocyte culture were stimulated with medium alone (lane 1), 1 μM ionomycin (1) (lane 2), 10 ng/ml TPA (T) (lane 3), T+1 (lane 4) for 6 hours and monitored for 4-1BB mRNA expression by Northern analysis. RNA was also isolated from CTLL-R8 cells and monitored for 4-1BB mRNA by Northern analysis (lane 5). Each lane contains 10 μg of total RNA. Blot was hybridized sequentially with a 4-1BB cDNA probe (24a) and with a CHOB probe (24b) as a control for equal loading in each lane.

The induction of 4-1BB mRNA was blocked by cycloheximide treatment, indicating that 4-1BB mRNA expression requires new protein synthesis (FIG. 26). Therefore, 4-1BB is classified as a member of the early gene family (58).

FIG. 26 shows transaction factors necessary for the induction of 4-1BB mRNA expression do not pre-exist in the resting T cell. Cycloheximide (CHX), a protein synthesis inhibitor, blocks the induction of 4-1BB mRNA in TPA alld ionomycin-activated thymocytes. Thymocytes cultures were stimulated with medium alone (lane 1), 20 μg/ml CHX (lane 2), T+1 (lane 3), or CHX+T+1 (lane 4) for 6 hours and monitored for 4-1BB mRNA expression by Northern blot analysis. Each lane contains 10 μg of total RNA. Blot was hybridized sequentially with a 4-1BB-cDNA probe (24a) and with a CHOB cDNA probe (4b) as a control for equal loading in each lane.

Figure 27A:
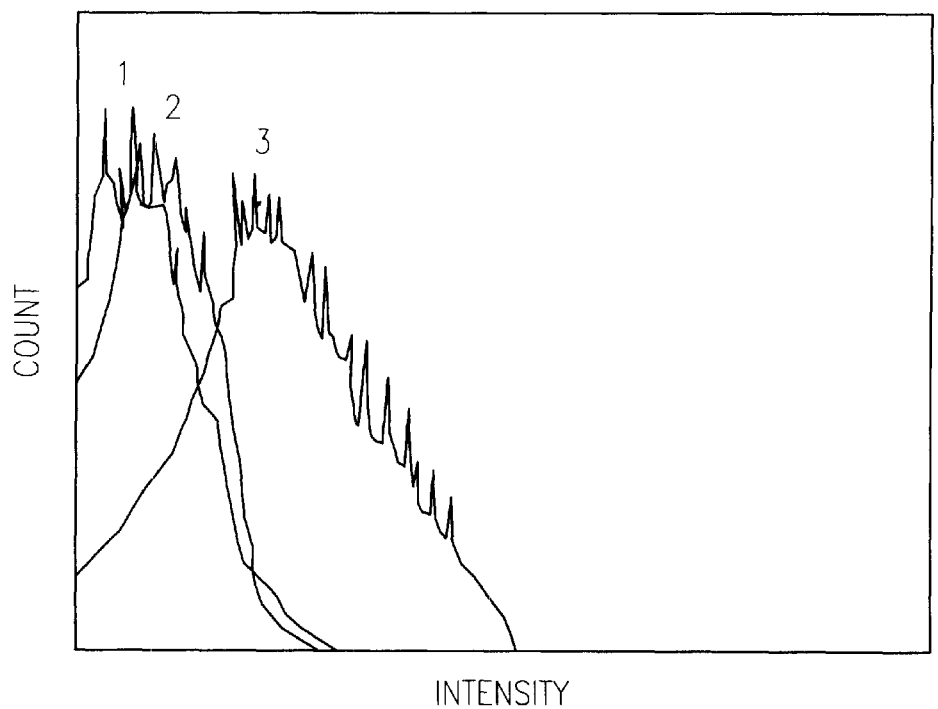
Figure 27B:
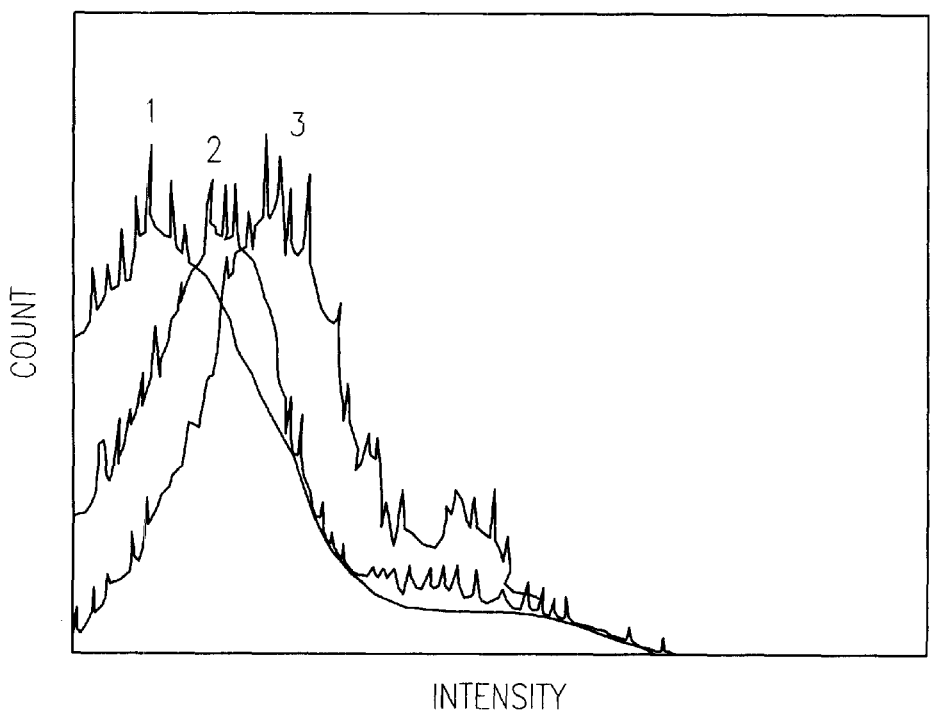
Figure 27C:
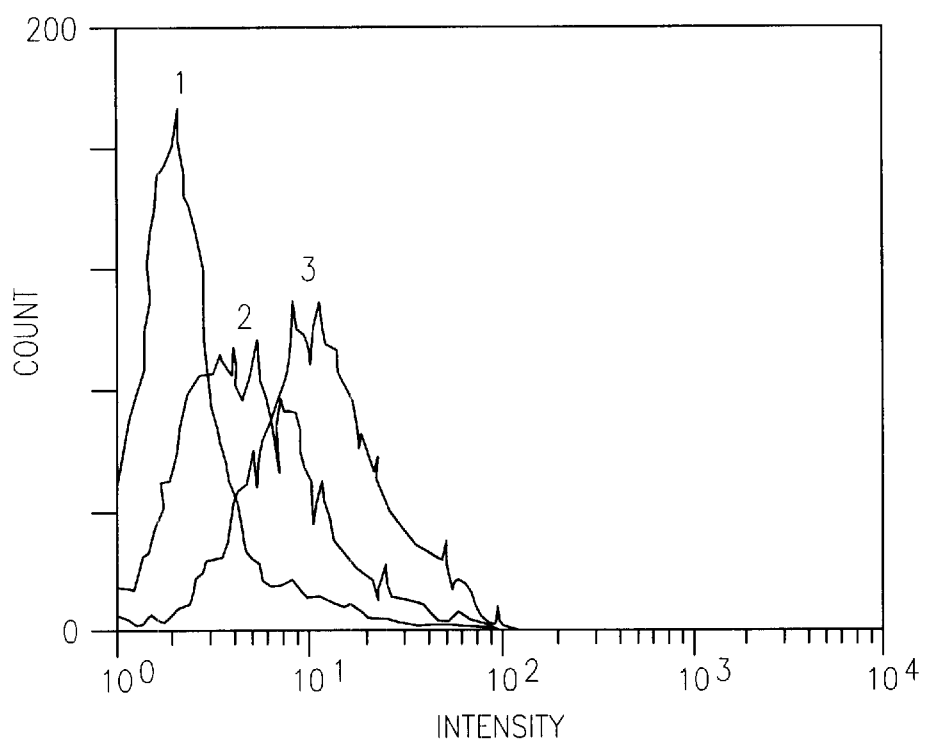
Figure 27D:
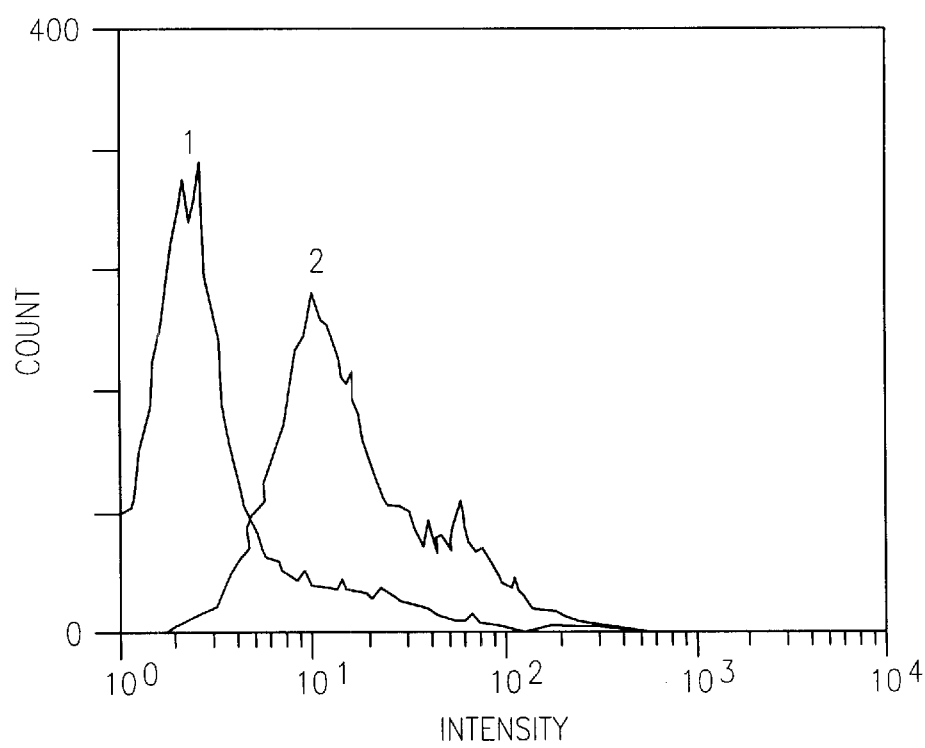

4-1BBP was expressed on the surface of activated thymocytes, splenic T cells, CD4$^+$ and CD8$^+$ T cells. As shown in FIG. 27, 4-1BBP was inducible when the thymocytes were treated with ionomycin plus PMA (FIG. 27a, peak 3) and when the splenic T cells were treated with anti-CD3 mAb (FIG. 27b, peak 3). The 4-1BBP was also induced in the CD4$^+$T cell clone, F1, by anti-CD3 mAb (FIG. 27c, peak 3) and was expressed constitutively in CTLL-R8 cells (FIG. 27d, peak 2).

FIGS. 27a–d show that 4-1BB is expressed on the cell surface of activated thymocytes, splenic T cells, CD4$^+$ and CD8$^+$ T cells. A Thymocytes were stained with FITCconjugated-goat-anti-rat IgG (anti-IgG-FITC) alone (peak 1) or with anti-4-1BB mAb plus anti-IgG-FITC on control thymocytes (peak 2) or thymocytes stimlulated with T+1 for 12 hrs (peak 3). B, Splenic T cells were stained with anti-IgG-FITC alone (peak 1) or with anti-4-1BB mAb plus anti-IgG-FITC on resting T cells (peak 2) or T cells stimulated with immobilized anti-CD3 for 12 hours (peak 3), C, A CD4$^+$ T cell clone, F1, was stained with anti-TgG-FITC alone (peak 1) or with anti-4-1BB mAb plus anti-IgG-FITC on control F1 cells (peak 2) or F1 cells stimulated with immobilized anti-CD3 for 24 hrs (peak 3). D, A CD8$^+$ T cell line, CTLL-R8, was stained with anti-IgG-FITC alone (peak 1) or with anti-4-1BB mAb plus anti-IgG-FTTC (peak 2).

Effect of the Anti-4-1BB mAb. 53A2, on Anti-CD3-stimulated T Cell Proliferation To determine whether biochemical signals delivered through 4-1BB may contribute to T cell activation, the anti-4-1BB mAb, 53A2, was potentiaily used to mimic ligand building to cell surface 4-1BB. Purified resting splenic T cells were stimulated with 10 μg/ml immobilized anti-CD3 in the absence or presence of 53A2.

FIG. 28 shows anti-4-1BB mAb, 53A2, enhances the prolifeation of anti-CD3-activated splenic T cells. Purified splnic T cells (5×10$^4$ cells/well) were stimulated in triplicate with 10 micrograms/ml immobilized anti-CD3 alone or in the presence of 10 micrograms/ml 53A2 or 10 micrograms/ml rat IgG$_1$ as a control. cultrues were incubated for the indicated times and plused for 12 to 14 hours with 1 μCi[$^3$H]thymidine. The cultures were harvested and [$^3$H] thymidine incorporation was measured by liquid scintillation counting.

In FIG. 28, on days 3–5 of activation, all enhancement of $^3$H thymidine incorporation was observed in T cells stimulated with anti-CD3 in the presence of 53A2. Enhancement of proliferation was not present when T cells were stimulated with anti-CD3 in the presence of a rat isotype-matched control antibody. In data not shown, the 4-1BB anti-peptide antiserum, 4-1BB-0, had no effect on anti-CD3-mediated T cell proliferation.

TABLE 4

|  | Day 3 | Day 4 | Day 5 |
| --- | --- | --- | --- |
| [$^3$H]Tdr Incorporation - Experiment I | | | |
| Control | 320 = 57 | 715 = 74 | 790 = 117 |
| 53A2 (10 μg/ml) | 1103 = 60 | 2268 = 232 | 3323 = 717 |
| IgG$_1$ (10 μg/ml) | 710 = 95 | 1501 = 165 | 1553 = 196 |
| αCD3 (10 μg/ml) | 3164 = 714 | 11217 = 735 | 17380 = 420 |
| αCD3 + 53A2 (10 μg/ml) | 44155 = 665 | 35796 = 370 | 60443 = 803 |
| αCD3 + IgG$^1$ (10 μg/ml) | 7945 = 1217 | 10404 = 1999 | 17843 = 2490 |
| Fold increase αCD3 vs αCD3 53A2 | 9.6× | 3.0× | 3.5× |
| [$^3$H]Tdr Incorporation - Experiment II | | | |
| Control | 336 = 185 | 284 = 35 | 120 = 26 |
| 53A2 (10 μg/ml) | 387 = 69 | 326 = 36 | 166 = 71 |
| IgG$_1$ (10 μg/ml) | 381 = 224 | 302 = 87 | 229 = 85 |
| αCD3 (10 μg/ml) | 16999 = 971 | 15823 = 209 | 6877 = 1176 |
| αCD3 + 53A2 (10 μg/ml) | 30570 = 1250 | 29875 = 343 | 10668 = 1165 |
| αCD3 + IgG$^1$ (10 μg/ml) | 17638 = 3274 | 15365 = 233 | 6238 = 110 |
| Fold increase αCD3 vs αCD3 53A2 | 1.8× | 1.9× | 1.6× |

In other experiments, the actual degree of enhancement ranged from an approximately 2–10fold increase in [$^3$H] thymidineincorporation in culturses stimulated with anti-CD3 alone (Table 4). Differences in actual enhancement of [$^3$H] thymidine incorporation, could be due to variability in the nunber or metabolic status of accessory cells in the cultures. For example, the highest-fold increase in T cells stimulated with anti-CD3 in the presence of 53A2 generally occurred when the proliferative effects of anti-CD3 were minimal (Table 4). It will be necessary to obtain T cell populations of higher purity to address this issue. These data, however, conclusively show that 4-1BB-mediated signals can contribute to T cell proliferation.

DISCUSSION

These experiments represent a further characterization of 4-1BB and show that 4-1BB may function as a cell surface receptor capable of transmitting biochemical signals during T cell activation.

The major species of 4-1BB on the cell surface appears to be a 55-kDa dimer. 4-1BB also appears to exist as a 30-kDa monomer and possibly as a 110-kDa tetramer. Since these 4-1BB species were immunoprecipitated from a homogenous population of cells (T cell clone F1), all forms potentially co-exist on each cell. A comparison of peptide digests from the 4-1BB monomer and dimer will be needed to determine whether 4-1BB exists as a homodimer on the cell surface. A variety of cell surface receptors such as the insulin receptor (59), the B cell surface immunoglobulin receptor (60), the T cell Ag receptor (61), the CD28 costimulatory receptor (62), and the CD27 T cell antigen (63) are composed of disulfide-bonded subunits. Receptor dimerization may be required for ligand binding and subsequent biochemical signaling.

4-1BB is not expressed on resting T cells but is inducible by activators which deliver a complete growth stimulus to the T cell. The combination of PMA and ionomycin is capable of mimicking those signals required for T cell proliferation. Although PMA or ionomycin alone induced 4-1BB mRNA, the combination of PMA and ionomycin resulted in optimal 4-1BB expression. Furthermore, the expression of 4-1BB was not transient. When purified splenic T cells were stimulated with immobilized anti-CD3, 4-1BB mRNA was expressed and this expression was maintained for up to 96 hrs poststimulation. Cell cycle analysis will be required to confirm that 4-1BB is expressed throughout cell cycle progression.

4-1BB is structurally related to members of the nerve growth factor receptor super-family. Although these receptors possess structurally similar ligand-binding properties (cysteine-rich regions), the cytoplasmic domains of these proteins are nonconserved which could allow for diversity in transmembrane signaling. Some members of this family are involved in the T or B cell activation process. There are in vitro functional data on the OX-40, CD4O and CD27 antigens. Antibodies against the OX-40 angment the T cell response in a mixed lymphocyte reaction (47) and antibodies against CD4O enhance B-cell proliferation in the presence of a coactivator, such as PMA or CD2O antibodies, and synergize with IL-4 in vitro to induce B-cell differentiation and to generate long-term normal B cell lines (64). One monoclonal antibody, anti-1A4, which recognizes an epitope on the CD27 molecule inhibited calcium mobilization, IL-2 secretion, helper T cell function, and T cell proliferation. On the other hand, CLB-CD27/1, another anti-CD27 mAb enhanced proliferation of human T cells stimulated with PHA or anti-CD3 mAb (63). These results indicate that the CD27 molecule plays an important role in T cell activation. Except for TNFRs, NCFR and CD4O, the ligands or cell surface molecules to which the members of the superfamily bind are not yet identified. Identification and characterization of the ligands to which the receptors bind will be helpful in better defining the physiologic role of 4-1BB.

To ascertain whether cell surface 4-1BB could contribute to T cell activation, the anti-4-1BB 53A2 was used as an agonist to 4-1BB. These data suggested that 4-1BB does in fact have the potential to function as an accessory signaling molecule during T cell activation and proliferation. The addition of soluble 53A2 to purified splenic T cells stimulated with immobilized anti-CD3 resulted in an amplification of $^3$H thymidine incorporation compared to T cells stimulated with anti-CD3 alone. This pattern of enhancement ranged from 2- to 10- fold in three independent experiments.

In the original two signal model of Bretschier and Cohn, they proposed that signal 1, the occupancy of the T cell antigen receptor (TCR), resulted in inactivation of the T cell in the absence of signal 2, which is provided by accessory cells. This has since been confirmed by a variety of studies (65). The identification of the accessory cell CD28 as a potent costimulatory receptor on T cells was a significant contribution in beginning to charactize the accessory signal (s) required for optimal T cell proliferation (66). It is possible that other cell surface molecules may contribute to these costimulatory activation requirements (67).

The biochemical signals delivered through 4-1BB are not completely known. One possibility considered was the observation that 4-1BB contains a putative $p56^{lck}$ tyrosine kinase binding doimain in its cytoplasmic tail. It was later determined that $p56^{lck}$ tyrosinase kinase binds to 4-1BB. It will also be worthwhile to determine if 4-1BB-mediated signaling can regulate genes such as IL=2 and IL-2 receptor, whose expression is required for T cell activation and subsequent proliferation.

Although the precise functions of member of the NGFR family appear to be diverse, an emerging theme is one in which these molecules may contribute in various ways to a maintenance of responsiveness or viability of the particular cell type in which they are expressed. For instance, NGF is absolutely required for viability of neurons in vitro and in vivo (68). The crosslinking of CD4O by soluble antiCD4–O monoclonal antibody blocks germinal center centrocytes from undergoing apoptosis in vitro (69). Signals delivered throug CD4O may also aid in maintenance of responsiveness to differeniation factors. The ligation of CD40 with antl-CD4O F(ab')$_2$ fragments in the presence of IL-4 induced large increases IgE synthesis (70). Also, anti-CD40 activated naive B cells treated with IL-10 and transforming growth factor-β became committed to IgA secretion (71).

In addition to sharing the molecular characteristics with the NGFR superfamily, it was noted that the 4-1BB contained a putative zinc finger structure of the yeast elF-2β protein (110). FIG. 17 shows a comparision of the 4-1BP amino acid sequence with the amino acid sequence in sina seven in absentia of Drosophila and DG17 of Dictyostelium. The amino acids that are share are boxed. Number represent the positions of the left-most residues relative to the N-terminus. Gaps (–) are introduced to allow for maximal alignment. 4-1BB also shares a conserved region with the sina seven in absentia of Drosophila, which is required for correct photoreceptor cell development (108). That particular region is also similar to the protein product of the DG17 gene of Dictyostelium, whose expression is specificaily induced during aggregation by cAMP (FIG. 17) (109).

This region forms the pattern of C-$X_2$-C-$X_9$-C-$X_3$-H-$X_3$-C-X-C (SEQ ID NO:8); and the cysteines and histidine are conserved in a similar space in 4-1BB, sina, and DG17 proteins. Ten of 24 amino acids between the 4-1BB and sina proteins are identical, and 3 of 24, are conservative substitutes. The conserved pattern suggests that these amino acids are functionally important. The sina protein is localized in the nucleus, suggesting that it has a regulatory function in cells. The fact that the amino acid sequence of4-1BB contains features like a zinc finger motif, a nuclear protein, and a receptor domain suggests that 4-1BB may play diverse roles during cellular proliferation and differentiation.

A T Cell Antigen 4-1BB Associates With the Protein Tyrosine Kinase $p56^{lck}$ 4-1BB is a 30 kD inducible T-cell antigen, and is expressed predominantly as a 55 K dimer on both CD4$^+$ and CD8$^+$ T lymphocytes. The cytoplasmic tail of 4-1 BB contains the sequence, Cys-Arg-Cys-Pro (SEQ ID NO:9), which is similar to the sequence Cys-X-Cys-Pro (SEQ ID NO:10), that mediates the binding of the CD4 and CD8 molecules to $p56^{lck}$ a protein tyrosine kinase[2,3]. An anti-4-1BB monoclonal antibody (53A2 mAb) was used to determine whether 4-1BB may associate with $p56^{lck}$. The 53A2 mAb specifically recognized 4-1BB on a CD8$^+$ T-cell line, CTLL-2, and coimmunoprecipitated a 56 K protein along with 4-1BB. Peptide mapping indicated that the 56 K phosphoprotein was identical to $p_{56}{}^{lck}$. The comimmunoprecipitation of $p56^{lck}$ with 4-1BB also occurred in nonlymphoid cells such as insect (Sf-21) and HeLa cells when the two recombinant proteins were coexpressed. Analysis of mutant $p56^{lck}$ recombinant proteins showed that two cysteine residues, critical for $p56^{lck}$-$CD_4$ (or CD8) complex formation, are also required for the $p56^{lck}$-4-1BB interaction. These studies establish that 4-1BB physically associates with $p56^{lck}$.

The T-cell activation marker, 4-1BB, is related structurally to members of the nerve growth factor receptor (NGFR) super-family, which are characterized by the presence of three to six patterns of a cysteine-rich motif in their extracellular domains. The members of NGFR super-family also contain hinge-like regions abutting their transmembrane domains with a high proportion of serine/threonine, likely to be glycosylated with 0-linked carbohydrates. The cytoplasmic domains of these receptors show no sequence similarities; therefore, diverse signaling pathways may be operative. 4-1BB expression is induced on CD4-$^+$ or CD8$^+$ T-cell surface by various T-cell mitogens or crosslinking of T-cell receptors (TCR). The calculated molecular weight of 4-1BB predicted from the cDNA nucleotide sequence is 25, 167 (233 amino acids). 4-1BB, however, migrates on a SDS polyacrylamide gel at a size of 28 to 30 K, suggesting its possible posttranslational modification.

An interesting feature of 4-1BB is its cytoplasmic domain containing a putative binding site for the T-cell-specific protein tyrosine kinase, $p56^{lck}$ a member of the tyrosine kinase family, is coupled to CD4-, CD8 (72,93), 3 PLC-γ (73) and the IL-2 receptor (74). Recently, other T cell antigens; e.g. , CD5(75) and CD2(76) have been listed as proteins associated with $p56^{lck}$ in human and rat cells, respectively. The consensus sequence for the $p56^{lck}$ binding site is -C-X-C-P- in the CD4 and CD8 molecues (72,93). $p56^{lck}$ is expressed at high levels in both developing and mature T cells and its activity is modulated during T-cell activation (77).

The role of 4-1BB during T-cell effector function is not entirely clear. A rat anti-mouse monoclonal antibody to 4-1BB, 53A2 (IgG$_1$) as disclosed herein which specifically recognizes an epitope on the extracellular domain of native and recombinant 4-1BB.

It has shown that 53A2 enhanced the anti-CD3-mediated proliferation of splenic T-cells, suggesting an involvement of 4-1BB during T-cell activation. In this study, 4-1BB ws shown to physically associates with p56$^{lck}$. It is now reported that in T-cells, 4-1BB is complexed with a kinase identified as p56$^{lck}$. 4-1BB and p56$^{lck}$ recombinant proteins are also associated when they are coexpressed in nonlymphoid cells. The interaction between 4-1BB and p56$^{lck}$ requires two critical cysteines of p56$^{lck}$ which are also essential for binding to CD4 or CD8 molecules in T cells.

FIGS. 29a–c show specificity of 53A2 mAb to native and recombinant 4-1BB. FIG. 29a shows the expression of 4-1BB on CTLL-2 cells. For FACS analysis, CTLL-2 cells were cultured for 16 hrs in the presence of 100 u/ml IL-2 without or with anti-CD3 (145, 2C11) (1 μg/ml)(134). Cells were incubated with 53A2 (10 μg/ml) in 2% fetal calf serum (FCS) containing RPMI-IM-0 at 4-° C. for 1 hr followed by FITC-goat anti-rat Ig antibodies. Peak 1 represents the background fluorescence from CTLL-2 cells treated with FITC-labeled goat anti-rat Ig alone. Peaks 2 and 3 indicate staining of cells cultured in the absence or presence of antl-CD3, respectively. FIG. 29b shows the expression of recombinant 4-1BB on insect cells (Sf-21). Insect cells infected with wild-type baculoviruses (FIG. 290b, peak 1), 4-1BB recombinant baculoviruses for 1 day (FIG. 29b, peak 2) and for 2 days (FIG. 29b, peak 3) were used for FACS analysis of 4-1BB with 53A2. FIG. 29c shows the immunoprecipitation analysis; 2×10$^7$ CTLL-2 cells were metabolically labeled overnight with [35S]- cysteine (0.1 mCi/ml) in cysteine-free RPM1-1640, 10% dialyed FCS, 2 mM glutamine, 1 mM sodium pyruvate, 5×10-5M 2-mercaptoethanol and 100 u/ml IL-2. Cells were lysed in 100 pl of 20 mM Tris-HCI, pH 7.4, 140 mM NaCl, 1% digitonin, 1 mM sodium orthovanadate, and 10 pg/ml aprotinin on ice for 15 min. Following microcentrlfugation at 10,000×g for 10 min to remove cell debris, the cellular lysate was incubated with iso-type-matched rat IgG$_1$ control (Zymed Lab. Inc.) (FIG. 29c, lane 1) or with anti-4-1BB mAb 53A2 (FIG. 29c, lane 2) at 4° C. for 1 hr. The immune complexes were recovered using 50 μl rec-protein G Sepharose 4B and washed with the lysis buffer, phosphate buffer containing 0.5M NaCl, then finally with PBS, and rEn on a 10% SDS polyacryamide gel under reducing conditions. The gel was processed with EN$^3$HANCE (NEN) for fluorography and exposed to X-ray film (Kodak XAR-5) for two days. The arrow indicates the 4-1BB proteins.

FACS analyses indicated that 53A2 specifically recognized 4-1BB expressed on cell surface of Sf-21 cells infected with 4-1BB-expressing baculoviruses. Sf-21 cells were infected with wild-type as a control (FIG. 29, peak 1) and 4-1BB recombinant baculoviruses for 1 (FIG. 29, peak 2) or 2 (FIG. 29, peak 3) days and assayed for cell surface expression of 4-1BB by FACS with 53A2 and subsequent FITC conjugate secondary antibody. 4-1BB was expressed on the stlrface of CTLL-2 cells (FIG. 29, peak 2) but at higher levels on CTLL-2 cells stimulated with anti-CD3 (145-2C11) for 16 hrs (FIG. 29, peak 3).

The 4-1BB antigen was immunoprecipitated with 53A2 from a lysate prepared from a metabolically [$^{35}$S] cysteine-labeled CTLL-2 (FIG. 29b). 4-1BB migrated on a 10% SDS polyacrylamide gel at approxirnately M$_r$ of 28 K under reducing conditions. When the immunoprecipitate was run under non-reducing collditions, an additional form of 4-1BB was detected at Mr of 55 K, suggesting the presence of a 4-1BB dimer in CTLL-2 cells (data not shown). Depending on lysis and washing conditions, we often observed extra bands at about M, of 45 K in 53A2-immunoprecipites of CTLL-2 cells.

The physical association between 4-1BB and p56$^{lck}$ was examined by a coimmunoprecipitation assay with 53A2 followed by an in vitro kinase-labeling reaction in the presence of [γ-$^{32}$P] ATP. This in vitro kinase assay provides greater sensitivity in monitoring the appearance of phosphoproteins in the immune complexes, and takes advantage of the fact that p56$^{lck}$ undergoes autophosphorylation, assuming that substrates would be phosphorylated by any associated kinase activity in the immune complex. CTLL-2 cells were lysed with 1% digitonin, and the lysate was immunoprecipitated with isotype-matched rat IgGl9 53A2 or anti-p56$^{lck}$ serum (72). The immune complexes were incubated with [γ-$^{32}$P] ATP and $^{32}$P-labeled proteins were detected by autoradiography.

FIGS. 30a and 30b show the identification of the coimmunoprecipitated proteins. FIG. 30a shows the communoprecipitation of 4-1BB and p56$^{lck}$ A CTLL-2 cell lysate was incubated with isotype-matched rat IgG$_1$ (lane 1), anti-4-1BB mAb 53A2 (lane 2) or anti-56$^{lck}$ (lane 3). The antip56$^{lck}$ is a polyclonal rabbit serum raised against a synthetic peptide corresponding to amino acids 39–64 of the murine p56$^{lck}$ protein (72). The immune complexes were precipitated as before, and subjected to the in vitro kinase reaction with 30 μCi [γ-$^{32}$P] ATP in 25 pl 25 mM HEPES, pH 7.4, 10 mM MnCI, and 0.1% NP-4-0 at 3° C. for 15 min. The reaction was terminated by adding 6 μl of 5×SDS sample buffer and boiling for 5 min. The $^{32}$P-labeled immune conlplexes were run on a 10% SDS polyacrylamide gel, transferred to Immobilon-P and exposed to S-ray film. The arrow indicates the 56 K phosphorylated bands (FIG. 30a). FIG. 30b shows V8 protease peptide mapping. $^{32}$P-phosphorylated proteins that were immunoprecipitated with 53A2 (FIG. 30b, lane 1) or with anti-p56$^{lck}$ (FIG. 30b, lane 3) were recovered and partially digested with S. aureus V8 protease (135). V8 protease-digests of lanes 1 and 3 correspond to the samples in lanes 2 and 4, respectively. The samples were resolved on a 15% SDS polyacrylamide gel under reducing conditions and exposed to X-ray film. Small arrows indicate the V8 protease digestion products in lanes 2 and 4 and the large arrow indicates the undigested phosphoproteins in lanes 1 and 3.

53A2 (FIG. 30, lane 2) coimmunoprecipitated a phosphoprotein with an M$_r$ of –56 K that migrated similarly to p56$^{lck}$ immunoprecipitated by anti-p56$^{lck}$ serum (FIG. 30a, lane 3). The immunoprecipitate from isotype-matched rat IgG, however, did not show any detectable phosphoprotein (FIG. 30, lane 1). To confirm that the 4-1BB-associated molecule was p56$^{lck}$, both phosphoproteins from 53A2 or anti-p56$^{lck}$ immunoprecipitations by digestion Niith S. u~ir.us V8 protease (FIG. 30b, lanes 2 and 4, respectively). Lanes 1 and 3 represent $^{32}$P-immunoprecipitates using 53A2 and anti-p56$^{lck}$ respectively. The digestion patterns of phosphoproteins generated from coimmunoprecipitates of 53A2 were identical to those from anti-p56$^{lck}$. These results suggest that 4-1BB associates with p56$^{lck}$ in CTLL-2 cells.

FIGS. 31a–c show an analysis of the association of 4-1 BB and p56$^{lck}$ in a baculoviral expression system. FIGS. 31a and 31b show an immunoblot of4-1BB and p56$^{lck}$ Sf-21 insect cells were infected with 4-1BB-, p56$^{lck}$-expressing recombinant baculoviruses or coinfected with 4-1BB and p56$^{lck}$-expressing recombinant baculoviruses. Total lysates from Sf-21 cells infected with these recombinant baculoviruses were blotted and probed with rabbit anti-4-1BB and rabbit anti-p56$^{lck}$ (FIGS. 31a and 31b, respectively). Antigens were visualized with alkaline phosphatase-conjugated secondary antibodies and chromogenic substrates, NBT and BCIP. Anti-4-1BB polyclonal rabbit serum was raised against the oligopeptide, CRPGQELTKQG (SEQ ID NO:13), which corresponds to amino acids 82 to 92 of mature 4-1BB. FIG. 31c shows an immune complex kinase assay of p56$^{lck}$. These Sf-21 cell lysates were also incubated with isotype-matched rat IgG$_1$ (FIG. 31c, lane 1), 53A2 (FIG. 31c, lane 2) or anti-p56$^{lck}$ (FIG. 31c, lane 3). The immune complexes were precipitated, subjected to the in vitro kinase reaction with [γ$^{32}$P] and run on a 10% SDS-polyacrylamide gel as described in FIG. 30. The arrow indicates the autophosphorylated p56$^{lck}$ proteins.

Sf-21, an insect cell line derived from Spadoptera fragiperda was grown at 27° C. in a synthetic serum-free medium, Excell 400 (JRH Bioscience) contining antibiotics. To generate recombinant 4-1BB or p56$^{lck}$ expressing baculoviruses, 4-1BB and murine p56$^{lck}$ cDNA's were cloned into PEV 55 baculoviral transfer vector (136) and Transferred to the *Autographa californica* nulear polyhedrosis virus (AcNPV) genome as described elsewhere (53). 4-1BB or p56$^{lck}$ cDNA containing baculoviruses were plaque purified and were grown in Sf-21 cells. 4-1BB or p56$^{lck}$ was expressed by infecting the Sf-21 cells with the recombinant viruses at a multiplicity of infection of 5 for 3 days. The infected cells were harvested, washed and lysed in the lysis buffer containing 1% digitonin for immunoprecipitation analysis.

The association of 4-1BB with p56$^{lck}$ as examined in nonlymphoid cells to confirm the specificity of the 4-1BB-p56$^{lck}$ complex, and to rule out the possibility that other T-cell-specific factors were involved in this interaction. To demonstrate the direct physical association of 4-1BB with p56$^{lck}$, 4-1BB was coexpressed with !nurine p56$^{lck}$ in insect (Sf-21) cells infected with recombinant baculoviruses (FIG., 31). An immunoblotting analysis was performed to ensure that recombinant proteins 4-1BB (FIG. 31a) and p56$^{lck}$ (FIG. 31b) were expressed in the appropriate infections. We used polyclonal rabbit antiserum raised against an 11 amino acid oligopeptide (cysteine-82 to g)ycine-92 in 4-1BB) was used for detection of 4-1BB, which allowed for enhanced detection of transblotted 4-1BB. Recombinant 4-1BB protein detected by immunoblotting appeared as multiple bands, presumably as a result of posttranslational modifications. Lysates from Sf-21 cells infected with 4-1BB-,p56$^{lck}$-recombinant baculoviruses or coinfected with both recombinant baculoviruses (FIG. 31) were subjected to immunoprecipitation with control rat IgG$_1$ (lane 1), 53A2 (lane 2) or anti-p56$^{lck}$ (lane 3) followed by in vitro phosphorylation in the presence of [γ$^{32}$P] ATP. Although 4-1BB was expressed in Sf-21 cells infected with 4-1BB recombinant baculoviruses (FIG. 31), none of the antibodies mentioned above immunoprecipitated a tyrosine-phosphoprotein from this lysate (FIG. 31, infection-4-1BB). This indicated that no endogenous tyrosine kinase capable of phosphorylating 4-1BB or p56$^{lck}$ existed in Sf-21 cells. As expected, only anti-p56$^{lck}$ imnlunoprecipi~ted p56$^{lck}$- phosphoprotein from a lysate prepared from cells infected with baculovirEses expressing p56$^{lck}$ (FIG. 31, infection-LCK, lane 3). Likewise, 53A2 and anti-p56$^{lck}$ but not control rat IgG$_1$, immunoprecipitated the p56$^{lck}$ phosphoprotein from a Sf-21 lysate containing both p56$^{lck}$ and 4-1BB (FIG. 31, infection-4-1BB+LCK, lanes 2 and 3). These results from nonlymphoid cells demonstrated that 4-1BB specifically associated with p56$^{lck}$ and excluded the possibility that other T-cell factors were required for the interaction.

The interaction between CD4 or CD8 and p56$^{lck}$ requires a specific binding site on each molecule[2,3]. The N-terminal region of p56$^{lck}$ interacts noncovalently with the cytoplasmic domains of CD4 and CD8 via pairs of cysteine residues in each moleculez, Therefore, it was determined whether the same cysteines of p56$^{lck}$ (cysteine 20 and 23) are required for the association with 4-1BB. p56$^{lck}$ constructs containing sequences encoding muatted p56$^{lck}$ proteins (construct C$_1$, cys 20- ser; construct C$_2$, cys 23- ser)[2] were employed in the following experiments. The capability of the cysteine-mutant p56$^{lck}$ proteins to associate with 4-1BB was tested by the coimmunoprecipitation assay. A vaccinia virus expression system was utilized in which the T7 RNA polymerase-expressing vaccinia virus allows transfected genes under the control of the T7 promoter to be expressed in HeLa cells[2]. High levels of coexpression have been achieved previously with this system to facilitate interactions between CD4 and p56$^{lck}$. To ensure consistent expression of 4-1BB, the transfected HeLa cells were briefly labeled with [$^{35}$S] cysteine before harvest. 4-1BB expression was monitored by immunoprecipitation of $^{35}$S-labeled 4-1BB with 53A2.

FIGS. 32a–c show an analysis of the association of 4-1BB and p56$^{lck}$ HeLa cells. FIG. 32a shows an immunoblot of p56$^{lck}$ HeLa cells were transfected with cDNAs encoding the indicated proteins and metabolically labeled with [$^{35}$S] cysteine. Lysates were immunoprecipitated with alltibodies to p56$^{lck}$ and 4-1BB and labeled with [γ-$^{32}$P] ATP by the in vitro kinase reaction. The positions of p56$^{lck}$ and 4-1BB are indicated to the right. Total HeLa cell lysates were immunoblotted with antibody top56$^{lck}$ assay thep56$^{lck}$ expression. FIGS. 32b and 32c show an immune complex kinase assay. Aliquots of the saline lysates were immunoprecipitated with antip56$^{lck}$ serum (FIG. 32b) or 53A2 (FIG. 32c) followed by the in vitro kinase reaction with [γ$^{32}$P] ATP as described in the legend to FIG. 30. 1×106 HeLa celis were grown to 80% confluency on 100-mm petri dishes in DMEM containing 10% FBS and antibiotics. Cells were infected with 1×10$^8$ pfu of vaccinia virus expressing T7 RNA polymerase (136) 30 min before transfection. DNA was transfected in liposomes (Lipofectin, GIBCO, BRL). 15 μg DNA and 50 μl liposome diluted into 5 ml serum-free DMEM were incubated in 12×75 mm polystyrene tubes at room temperature for 15 min.

The expression of p56$^{lck}$ was assayed by immunoblotting of a total cellular lysate with anti-p56$^{lck}$ (FIG. 32). The association between 4-1BB and p56$^{lck}$ was examined by the in vitro kinase-labeling of the 53A2 immune complex as in the baculoviral expression system (FIG. 32). 4-1BB, wild-type p56$^{lck}$ oy the combination of 4-1BB and p56$^{lck}$ of either the wild-type or mutant phenotypes, C1 or C2, were expressed in HeLa cells (FIG. 32c). 53A2 coimmunoprecipitated p56$^{lck}$ with 4-1BB only when 4-1BB was coexpressed with the wild type p56$^{lck}$. The coimmunoprecipitation of p56$^{lck}$ with 4-1BB by 53A2 was not observed when 4-1BB was coexpressed with either of the C1 and C2 P56$^{lck}$ proteins (FIG. 32c). As shown in previous studies in the baculoviral expression system, the fact that the presence of 4-1BB was required for 53A2 to coimmunoprecipitated p56$^{lck}$ ruled out the possibility of cross-reactivity of the 53A2 mAb with p56$^{lck}$ 4-1BB associated specifically with the wild-type p56$^{lck}$ and mutation of cys 20 or cys 23 of p56$^{lck}$, crucial for binding to CD4 or CD8, prohibited interaction with 4-1BB in HeLa cells. The disruption of coimmunoprecipitation of mutated p56$^{lck}$ was not due to lack of expression of el~her p56$^{lck}$- or 4-1BB as proven by comparable levels of ex~ression of immunoblotted p56$^{lck}$ (FIG. 32a) and immunoprecipitated [3SS] 4-1BB (FIG.

32c). FACS staining with 53A2 of HeLa cells transfected with 4-1BB and p56$^{lck}$ wild-type, C1 or C2 Ir~dicated that the expression levels of cell surface 4-1 BB were comparable (data not shown). Since the detection of p56$^{lck}$ was dependent on its in vitro labeling efficiency, the specific autophosphorylation activity of the wild-type and mutant p56$^{lck}$ proteins was compared. Cell lysates containing each p56$^{lck}$ recombinant protein were immunoprecipitated with anti-p56$^{lck}$ serum and autophosphorylated. As shown in FIG. 32b, the band intensities of wildtype and mutant p56$^{lck}$ were comparable. Thus, all the p56$^{lck}$- mutants tested showed similar autophosphorylation activities and were expressed at similar levels in the cells. This suggests that the specific kinase activity of mutant p56$^{lck}$ was almost identical to that of wild-type p56$^{lck}$. Therefore, it was concluded that the failure of the mutant p56$^{lck}$ C1 or C2, to associate with 4-1BB was due to the absence of critical cysteine residues but not due to a defect in kinase activity caused by mutation.

The fact that 4-1BB physically associates with p56$^{lck}$ and that its interaction requires the same two cysteines in p56$^{lck}$ also critical to binding to CD4- or CD8 suggests that 4-1BB may compete with CD4 or CD8 for coupling to p56$^{lck}$- Expression of 4-1BB is highly inducible during T-cell activation, in contrast to that of CD4 or CD8, which is constitutively expressed. Therefore, it is conceivable that the exact intracellular localization of p56$^{lck}$ in T cells may be modified during cell activation with increasing amounts of competing binding sites for p56$^{lck}$ provided by 4-1BB. At present, the relative binding affinity of p56$^{lck}$ to 4-1BB or to CD4 or CD8 in unknown as well as the relative amount of p56$^{lck}$ binding with 4-1BB or CD8 in CTLL-2 cells.

The CD4- or CD8 -p56$^{lck}$ association has been shown essential for the optimal response of T cells to antigen (124). p56$^{lck}$ incorporated in the antigen-receptor complex through the juxtaposition of CD4 or CD8 coreceptors might serve to relay and modify TCR signals to the cell interior (125). This signaling relay may be attributed to the physical proximity of CD4- to TCR, caused by either crosslinking reagents or antigen presentation by MHC Class II molecules (126). At this time, it is still possible that 4-1BB may assemble with the CD4- or CD8-p56$^{lck}$ complex rather than act as a competitor of CD4- or CD8. The association of p56$^{lck}$ with 4-1BB may expose this kinase to other regulatory proteins and substrates. Likewise, the regulation of p56$^{lck}$ by CD4 or CD8 might be modified once 4-1BB is expressed. Recently, the CD4 or CD8- p56$^{lck}$ complex has been found to include additional proteins (127) such as a GTP-binding protein, p32 (128) or Raf-I-related protein, p110 (129), as an assembled complex. The association ofp56$^{lck}$ and CD4 may be regulated by intracellular signals, for the protein kinase C-activator, TPA, caused the internalization of CD4 (130) as well as the dissociation of CD4- from p56$^{lck}$ (131) lf the $_{4-1}$BB-p56$^{lck}$ association is regulated by T-cell immunoregulatory factor, the outcome would provide a further mechanism for regulating T-cell growth and subsequent immune function.

The 53A2 monoclonal antibody enhanced the proliferative response of anti-CD3- stimulated murine splenic T cells. A recent study (132) suggested that 4-1BB contains N-linked and 0-linked carbohydyrates as well as sialic acid, and interacts with various extracellular matrix components. The possibility that stimulatory signaling through 4-1BB involves an alteration in p56$^{lck}$ mediated protein tyrosine phosphorylation is being pursued. Since not all cellular p56$^{lck}$ is associated with CD4- or CD8, and since p56$^{lck}$ is involved in thymocyte development (77, 133), it is plausible that the 4-1BB-p56$^{lck}$ complex may be involved in regulating early and/or late antigen receptor induced-signals, or possibly intrathymic differentiation of T cells.

4-1BB T-cell Antigen Binds to Mature B Cells and Macrophages, and Costimulates Anti-$\mu$ Primer Splenic B Cells 4-1BB is expressed on activated murine T cells and may function as an accessory signaling molecule during T-cell activation. In order to identify putative cell-surface 4-1BB ligands, a fusion protein consisting of the extracellular domain of 4-1BB fused to human placental alkaline phosphatase (4-1BB-AP) was construed. Alkaline phosphatase activity was used as an indicator of the relative amount of bound 4-1BB. The 4-1BB-AP fusion protein was used in a semi-quantitative binding assay and for in situ staining to determine if a membrane-bound ligand exists for 4-1BB. These studies indicate that 4-1BB-AP bound to the surface of various mature B- and macrophage-cell lines. The binding was saturable, and inhibited by recombinant, soluble 4-1BB protein. 4-1BB-AP bound at low levels or not at all to T-cell lines (non-activated and anti-CD3-activated), pre-B-cell lines, an inunature macrophage cell line, a glial tumor-cell line, HeLa cells, or COS cells. In addition, 4-1BB-AP bound to F(ab') anti-$\mu$- activated primary culture B cells but not to anti-CD3-activated primary culture T cells. Although signals delivered through 4-1BB may influence T-cell activation, the results presented here, suggest that 4-1BB may, in addition, function as a regulator of B-cell growth. The addition of paraformaldehyde-fixed SF21 cells expressing recombinant 4-1BB, synergized with F(ab'), anti-$\mu$ in inducing splenic B-cell proliferation.

Although the interaction of the T-cell receptor complex with its specific peptide/MHC on antigen presenting cells (APCs) is required for effective collaboration between these cells, it is becoming clear that a plethora of other cell-cell interactions is also necessary. These receptor-counter receptor interactions are being studied extensively in model systems of thymus-dependent B-cell activation; it has been proposed that B-cell/T-cell interactions result in a co-directional relay of biochemical signals which are responsible for cell cycle commitment (78). Receptor-ligand pairs between B and T cells presently characterized are the LFA-1/ICAM-1 (79) and CD2/LFA-3 (80) receptor pairs involved in cell adhesion; the Lyb2/Lyl (81) the B7/CD28 (82) or the B7/CTLA4 (83) involved in T-cell costimulation; and the CD4O/CD4OL (84,85)which is involved in B-cell proliferation and differentiation.

4-1BB is a member of the Nerve Growth Factor Receptor (NGFR) superfamily (89,92) and is expressed on the surface of activated CD4$^+$ and CD8$_+$ murine T cells. The NGFR superfamily members are characterized by the presence of three to six patterns of a cysteine-rich motif, each consisting of about 40 amino acids in the extracellular region of the molecule. These cysteine-rich motifs may result in receptors possessing extracellular domains with similar tertiary structures and thus similar ligand-binding properties. In contrast, the cytoplasmic tails of these receptors are unique, predicting that different biochemical signals could be delivered intracellularly once the ligand binds.

The majority of cell-surface 4-1BB exists as a 55 kDa. dimer on the surface of T cells. 4- 1BB may act as an accessory signaling molecule during T-cell activation; the addition of an anti-4-1BB-monoclonal antibody, 53A2, resulted in an enhancement of the anti-CD3-induced proliferation of purified splenic T cells. Although the actual biochemical signals delivered through 4-1BB are not known, it has been shown that 4-1BB is coupled to the tyrosine kinase, p56[lck], suggesting that this kinase may play a role in transmitting signals delivered through 4-1BB (under publication).

At present, in the NGFR superfamily, only ligands for the NGFR (105), Tumor necrosis factor receptors I and II (48), and CD40 84,85) have been identified. To identify 4-1BB cell-surface ligands, a 4-1BB fusion protein, 4-1BB-AP, which consists of the extracellular domain of 4-1BB fused to human placental alkaline phosphatase was generated. The 4-1BB-AP fusion protein bound to various mature B-and macrophage-cell lines. In addition, data presented in this report suggest 4-1BB may act as a signaling molecule for anti-$\mu$-primed B cells. The identification of cell surface and/or soluble 4-1BB ligands will be essential in understanding the physiological role of 4-1BB during T-cell-APC interactions.

Materials and Methods

Mice. Female Balb/c mice were obtained from Harlan Indianapolis, Ind.) and used at 6–10 weeks of age. Cells. NIH-3T3 cells were maintained in DMEM containing 7% fetal bovine serum (FBS) (DMEM-CM). 2PK-3, WEHI-231, and 70Z/3 cells were maintained in DMEM containing 10% FBS, 50 $\mu$M 2-mercaptoethanol (2-ME) and antibiotics. HeLa and COS cells were maintained in RPMI-1640 containing 10% FBS, and antibiotics (RPMI-CM). A20, 230, WEHI-3, and P388D$_1$ cells were maintained in RPMI-CM supplemented with 1 mM sodium pyruvate, 1 mM nonessential amino acids, and 2-ME (RPMICM$^+$). The BCL$_1$-5B$_1$b (BCL$_1$) B-cell leukemic cells were maintained in RPMI-CM$^+$ with 15% FBS. The PU5-1.8 and RAW-264.7 cells were maintained in RPMI-CM containing 2-ME. The WR19M.1 cells were maintained in RPMI-CM$^+$ containing 10% horse serum and 5% FBS. CTLL-2 (CD8$^+$), CTLL-R8 (CD8$^+$), D 10.G4 (CD4$^+$) (106), and F 1 (CD4$^+$) cells, were maintained in RPMI-CM containing 10% Rat Con A supernatant (106). Spodoptera frugiperda (SF-21), an insect cell line was grown in synthetic serum-free Ex-cell 400 medium (JRH Biosciences) containing antibiotics at 27° C. These cells were infected with wild-type baculoviruses or baculoviruses expressing either the recombinant full-length 4-1BB or the recombinant extracellular domain of 4-1BB (rs4-1BB), as previously described (53). (The 230 and WR19M. 1 cells were a generous gift of Dr. Pat Stuart, and the D10.G4 and F1 T-cell clones were a generous gift from Dr. Scott Bryson, both of the University of Kentucky, Lexington, Ky. The PU5-1.8, P388D, and C$_6$ cells were a generous gift of Dr. Randy Rosenthal, University of Indiana, Indianapolis, Ind. The BCL$_1$-5B$_1$b cells were the kind gift of Dr. Roman Dziarski, Northwest Campus, Indiana University, Gary Ind. The other lymphoma cell lines were obtained from American Type Culture Collection.)

Production of the 4-1BB-AP fusion protein. The 5' portion of the 4-1BB cDNA including sequences encoding the original signal peptide and the entire extracellular domain, was amplified by the polymerase chain reaction (PCR) (99). For correctly oriented cloning, a Hind III site on the 5' end of the forward primer and a Bgl II site on the 5' end of the reverse primer were created. The Hind III-Bgl II 4-1BB fragment was inserted into the mammalian expression vector AP-tag-1, upstream of the coding sequence for human placental alkaline phosphatase (Ap) (113). (The AP-tag-1 vector was a kind gift of Dr. John Flanagan, Harvard University, Cambridge, Mass.). Sequence analysis of the fusion region confirmed that the 4-1BB and AP sequences were joined in frame. The 4-1BB-AP plasmid, linearized with Cla I, was cotransfected with the linearized-selectable marker plasmid, pSV7neo, by the calcium phosphate coprecipitation method. After selection in 500 $\mu$g/ml G418, resistant colonies were picked and expanded. Clones were subsequently screened for secretion by assaying for AP activity. Supernatant from one clone, 4-1BB-AP-2, which produced the 4-1BB-AP fusion protein, showed high levels of alkaline phosphatase activity; 738 OD units/hr/ml. When determining total 4-1BB-AP or AP activity, serial dilutions were performed so that AP activity was measured at non-saturating levels. The 4-1BB-AP or AP was then diluted accordingly so equivalent levels of 4-1BB-AP or AP activity were added to each sample. DMEM-CM containing purified human placental AP (Sigma, St. Louis Mo.) was utilized as a background control in all experiments.

Western Analysis of 4-1BB-AP. Protein samples were resolved by electrophoresis on a 12% SDS-polyacrylamide gel, and transferred electrophoretically onto an Immobilon-P membrane (Millipore, Bedford, Mass.). The membranes were blocked to prevent nonspecific antibody binding by incubating in 5% nonfat dry milk in TBST (50 mM Tris HCl, pH 7.4, 0.15 M NaCl and 0.05% Tween-20) for 1 hr at room temperature. The membrane was then incubated with an anti-4-1BB peptide serum (anti-4-1BB-0) at room temperature for 1 hour with gentle agitation. The 4-1BB-0 oligopeptide was a 11-mer from amino acids 105–115 of the deduced 4-1BB sequence (89). After four washes with TBST, the membranes were incubated with a secondary antibody against rabbit IgG(H+L)-alkaline phosphatase conjugate at 1:1000 dilution. The reactive bands were visualized by incubating the membrane with chromogenic substrates, p-nitroblue-tetrazolinum chloride (NBT) and 5-bromo-4-chromo-3-indolyl-phosphate (BCIP) in 0.1 M Tris, pH 9.5, 0.1 M NaCl, and 5 mM MgCl$^2$.

4-1BB-AP Ouantitative Binding Assay. The method of Flanagan and Leder (113) was used with some modification to assay for cell-bound 4-1BB-AP. Cells were washed with HBHA buffer [Hank's balanced salt solution with 0.5 mg/ml BSA, 0.1% NaN$^3$, 20 mM HEPES (pH 7.0)]. Two×10$^6$ cells per sample were incubated in eppendorf tubes with DMEM-CM containing equivalent levels of 4-1BB-AP or AP activity. All supernatants contained 0.1% NaN$^3$. Samples were incubated for 60–90 minutes at 4° C. with slow rotation. The cells were pelleted and washed three times with HBHA buffer. The cells were then lysed in 375 $\mu$l 1% Triton X-100, 10 mM Tris-HCl (pH 8.0). The lysate was vortexed vigorously and the nuclei removed by centrifugation at 10,000×g for 5 minutes. This assay takes advantage of the fact that this particular AP isozyme is stable at 65° C. whereas endogenous phosphatases are inactivated at this elevated temperature. Supernatants were placed in clean tubes and heated for 10–15 minutes at 65 ° C. to inactivate background cellular phosphatases.

Alkaline Phosphatase assay. Each sample was assayed for AP activity in triplicate. Alkaline phosphatase activity was measured by incubating 100 $\mu$l of heat-inactivated supernatants with 100 $\mu$l of 2×AP buffer (1×=1M diethanolamine pH 9.8, 0.5 mM MgCl$^2$, 10 mM homoarginine, 0.5 mg/ml BSA and 12 mM P-nitrophenyl phosphate), and measuring the OD$_{405}$. (114).

In situ analysis of 4-1BB-AP binding. Binding and washing were done as described above for the 4-1BB-AP quantitative binding assay. The cells were then spun onto slides by a cytospinner (Cytospin 2, Shandon, UK) and subsequently fixed for 30 seconds in 60% acetone, 3% formaldehyde, 20 mM HEPES (pH 7.5), washed twice for 5 minutes each in 150 mM NaCl, 20 mM HEPES (pH 7.5).

The slides were then floated on 65° C. water bath for 10 minutes to inactivate cellular phosphatases. After rinsing with 100 mM Tri-HCl (pH 9.5), 100 mM NaCl, 5 mM $MgCl_2$, the cells were stained for 72 hours in the same buffer containing 10 mM L-homoarginine, 0.17 mg/ml BCIP, 0.33 mg/ml NBT for color development. Methyl green was used as a counter stain for nuclei. The slides were mounted using glyceroi-polyvinyl alcohol aqueous mounting medium.

Purification of the 4-1BB-AP fusion protein. Culture supernatants from NIH-3T3 transfectants (DMEM-CM) containing 4-1BB-AP fusion Protein were initially fractionated and concentrated by ammonium sulfate precipitation (60% saturation). Precipitates were resuspended at 10% of the original volume in 40 mM Tris, pH 8.0 and dialyzed overnight against the same buffer. The proteins were fractionated by ion exchange chromatography on Q-Sepharose fast flow (Pharmacia, Piscataway, N.J.) at pH 8.0, Fractions containing 4-1BB-AP were identified by AP activity and an immunoblot assay as described above. 4-1BB-AP containing fractions were pooled and dialyzed overnight against 40 mM Tris 150 mM NaCl, pH 7.5. The dialyzed proteins were affinity purified using an anti-human placental alkaline Phosphatase row affinity anti-AP antibody, Medix Biotech, Foster City, Calif.)-affinity column (Affi-gel HZ, BioRad, Richmond, Calif.) as described by Flanagan and Leder (113), with the exception that the elution buffer was adjusted to pH 4.5. Fractions containing 4-1BB-AP fusion protein were identified by AP and immunoblot assays and their purity was assessed by Coomassie blue staining of a 10% SDS-polyacrylamide gel.

Costimulation of splenic B cells with paraformaldehyde-fixed SF21 cells expression recombinant 4-1BB. Spleens were removed aseptically from mice sacrificed by cervical dislocation, and teased into a single cell suspension in 5% FBS-RPMI-1640. Small resting B cells were purified by treatment with anti-L3T4 (clone GKI.5), anti-Thy 1.2 (clone 13-4.6) followed by baby rabbit complement (PelFreeze, Brown Deer, Wis.). The B cells subsequently were fractionated by centrifugation at 2000×g for 30 min at 4° C. on a four step gradient consisting of 80% (1.08 g/ml), 70% (1.07 g/ml), 60% (1.06 g/ml), and 50% (1.05 g/ml) Percolt solutions. Resting B cells were recovered from the interface between the 60% and 70% Percoll layers. These B cell preparations were 90% L3T$^-$ and were unresponsive to Con A. SF21 cells were infected for 36 hours with wild-type baculoviruses (SF21-wt) or recombinant baculoviruses expressing the full length 4-1BB (SF21-4-1BB). After infection, cells were washed twice in HBSS, fixed with 1% paraformaldehyde for 15 minutes at room temperature, and washed once with HBSS. The fixed cells were then resuspended in 25 ml of 0.1 M lysine for 30 minutes at room temperature, and washed once in RPMI-CM. Five×$10^4$ fixed-SF21 cells (SF21-wt or SF21-4-1BB) were incubated with 1×$10^5$ B cells per well in 96 well microtiter plates. After 72 hours of stimulation, cultures were pulsed with 1 $\mu$Ci per well $^3$H-thymidine for 16 hours. Cultures were harvested onto glass fibre filters, and $^3$H-thymidine incorporation was measured in a liquid scintillation counter.

RESULTS

Expression of the 4-1BB-Alkaline Phosphatase (4-1BB-AP) fusion protein. In the mammalian expression vector, APtag-1, the 5' extracellular domain of a receptor can be fused with AP (113). This intrinsic AP activity can be used to monitor the binding of a soluble receptor to the cell surface with high sensitivity in both semi-quantitative and in slit assays. The 5' portion of the 4-1BB gene consisting of sequences encoding the signal peptide and the entire extracellular domain immediately before the first hydrophobic amino acid of the transmembrane region (4-1BBs), was inserted upstream of the entire coding sequence of AP in the APtag-1 vector. The 4-1BB-AP expressing plasmid, 4-1BB-AP-TAG, and pSV7neo were cotransfected into NIH-3T3 cells and G418-resistant clones were selected. Northern and Western analyses, and the AP assay were used to select for clones that produce high levels of 4-1BB-AP in the supernatant. An anti-4-1BB-immunoreactive band of approximately 85 kDa. FIG. 33 shows the expression of the 4-1BB-AP fusion protein and rs4-1BB. Supernatants from rs4-1BB baculovirus-infected SF21 cells lane 1), Neo$^r$-NI3T3-cells (lane 2), and 4-1BB-AP/Neo$^r$-NIH-3T3 cells lane 4) were analyzed by a Western blot which was probed with the anti-4-1BB-0 serum. Lane 3 represents Coomassie blue-preshined molecular weight standards. Lane 5 represents 10 $\mu$g purified human placental alkaline phosphatase stained with Coomassie blue. The 4-1BB-AP fusion protein is 85 kDa. lane 4), and the AP protein is 67 kDa. (lane 5) was secreted into the supernatant. The 85 kDa. protein was recognized by an anti-4-1BB peptide serum (4-1BB-0) (FIG. 33) and by an anti-4-1BB monoclonal antibody, 53A2 (data not shown). The purified 85 kDa. fusion protein possessed AP activity, and consisted of the 67 kDa. AP protein (FIG. 33, lane 5) and the 18–23 kDa. rs4-1BB protein (FIG. 33, lane 1).

Ouantitative Analysis of 4-1BB-AP binding to lymphoid and nonlymohoid cell lines. Measurement of AP activity as an indicator of bound 4-1BB-AP provided a reliable method for an initial determination of the relative amount of 4-1BB-AP bound to one cell as compared to another cell type. Two×$1^6$ cells were incubated in 1 ml of DMEM-CM containing equivalent levels of 4-1BB-AP or AP activity (700 OD units/hr/ml). In all experiments, cell viability was $\geq$95% as determined by trypan blue exclusion. The cells were washed, lysed, and assayed for AP activity. The relative levels of 4-1BB-AP bound were determined by subtracting background levels of AP bound from levels of 4-1BB-AP bound to each cell type. The range of AP bound routinely ranged from an OD$^{405}$, 0.1 to 0.45.

FIGS. 34a–c show the quantitative analysis of 4-1BB-AP binding to lymphoid- and nonlymphoid-cell lines. In Experiments I and II 2×$10^6$ cells were used per sample. In Experiment III, 2×$10^6$ 2PK-3 cells, and 6×$10^6$ purified splenic B cells or T cells, or FI-T cells were used per sample. Samples were incubated with 4-1BB-AP or AP, washed, and assayed for AP activity.

The highest level of 4-1BB-AP binding was observed with the IgG$^+$ B-cell A20 and 2PK-3 lymphomas (FIG. 34a). LPS (15 $\mu$g/ml) or a cytokine-rich supernatant (1:10) from D1O.G4 cells (D1Os) increased the level of 4-1BB-AP binding to A20 cells. Increased levels of 4-1BB-AP binding were also observed when 2PK-3 cells were stimulated with these reagents (data not shown). In contrast, WEHI-3, a myelomonocytic cell line, or 230, a pre-B cell line, bound low levels of 4-1BB-AP, and when stimulated with LPS for 24 hours did not show increased binding to 4-1BB-AP (FIG. 34b) and data not shown). TPA caused a slight down regulation of 4-1BB-AP binding sites on A2O cells. The CD4$^+$ T-cell clones, F1 and DIO.G4, and the CD8$^+$ T-cell line, CTLL-2, bound negligible levels of 4-1BB-AP (FIG. 34a). Activation of CTLL-2 cells by anti-CD3 did not increase binding of 4-1BB-AP to any significant degree. In data not shown, 4-1BB-AP also did not bind to CTLL-R8 cells or to anti-CD3-activated F1 or D10.G4 cells. 4-1BB-AP did not bind to nonlymphoid cells such as C$^6$ (rat glial tumor), HeLa (human epitheliod carcinoma), or COS cells (monkey SV-40-transformed fibroblast) (FIG. 34a).

Most notably, the IgG+ B cells (2PK-3, A20) bound higher levels of 4-1BB-AP than the IgM+ B cells (WEHI-231, BCL$_1$) or the IgG- pre-B cells (230) (FIG. 34b). In other experiments, another IgG- pre-B cell line, 70Z/3, bound levels of 4-1BB-AP comparable to 230 pre-B cells (data not shown). While the macrophage cell line, WR19M.1, bound 4-1BB-AP at levels similar to those bound by IgM+ B-cell lines, the macrophage cell lines, PU5-1.8 and RAW 264.7 bound 4-1BB-AP at levels similar to those of the IgG+ B-cell lines (FIG. 34b). Not all lymphoid cell lines bound to 4-1BB-AP, for P388D, cells (FIG. 34a) and WEHI-3 cells, (FIG. 34b), bound neglible levels of 4-1BB-AP. These data suggest that a 4-1BB-binding site potentially exists on the surface of mature APCs such as macrophages and B cells; it is possible 4-1BB may regulate some aspect of APC function.

It was also determined if 4-1BB-AP bound to normal B cells. Resting splenic B cells were purified and found to bind low levels of 4-1BB-AP (FIG. 34c). B cells stimulated with Goat anti-mouse F(ab'), anti-$\mu$ (anti-$\mu$) (Cappel, Durham, N.C.) for 24 hours, also exhibited low levels of 4-1BB-AP binding, while at 60 hours post-stimulation with anti-$\mu$, binding increased 4 fold compared to nonstimulated B cells. Low levels of 4-1BB-AP bound to resting T cells purified as previously described above by a nylon wool column; this binding may be attributed to small levels of activated B cells or macrophages in the culture. However, no increased binding was observed when 4-1BB-AP was added to T cells stimulated with anti-CD3 for 24 and 60 hours. This study demonstrated that selective binding of 4-1BB-AP to B-cell lines compared to T-cell lines was not merely a characteristic of transformed B-cell lines, since activated primary culture B cells also possessed significantly higher levels of 4-1BB-AP binding than activated primary culture T cells.

In data not shown, B-cell lymphomas were washed in an acid buffer (10 mM sodium citrate, 140 mM NaCI, 0.1% bovine serum albumin, pH 4.0) prior to the addition of 4-1BB-AP to remove bound ligands from the cell surface (115). 4-1BB-AP bound to cells washed with HBHA buffer or acid buffer at identical levels (data not shown). This ruled out the possibility that 4-1BB-AP was binding to proteins extrinsically attached to the cell surface.

Characterization of 4-1BB-AP binding to the A20 B-cell Lymphoma. A20 or D10.G4 cells were incubated with increasing amounts of 4-1BB-AP to determine the concentration required to saturate 4-1BB-AP binding sites. Saturation was reached at approximately 375 ng/ml (4.4 nM) 4-1BB-AP (FIG. 35a). AP activity was indicative of the saturability of 4-1BB-AP binding sites since the AP substrate, pnitrophenyl phosphate, which was present in excess.

FIGS. 35a and 35b show the characterization of 4-1BB-AP binding to A20 B-cell lymphoma cells. FIG. 35a shows the saturation of 4-1BB-AP binding sites on A2O cells. Twox10$^6$ A2O or D1O cells were incubated with increasing concentrations of 4-1BB-AP, washed, and assayed for AP activity. FIG. 35b shows the inhibition of 4-1BB-AP binding to A2O cells in the presence of rs4-1BB. Twox10$^6$ A2O cells were preincubated with or without 20 $\mu$g/ml rs4-1BB for 30 minutes on ice. Samples were then incubated with 4-1BB-AP or AP. The cells were washed and assayed for AP activity.

The specificity of 4-1BB-AP binding was analyzed by pre-incubating A20 cells with rs4-1BB prior to the addition of 4-1BB-AP. For expression of rs4-1BB, SF21 cells were infected with recombinant baculoviruses containing the sequence encoding the extracellular region of 4-1BB; rs4-1BB was purified from supernatants of infected SF21 cells as described above. A20 cells were preincubated in 1 ml of PBS, 2% BSA, 0.1% sodium azide with or without 20 $\mu$g/ml (50 fold excess) rs4-1BB for 30 minutes on ice. 4-1BB-AP was subsequently added b rs4-1BB-treated and nontreated A20 cells at saturating levels (FIG. 35 -375 ng/ml). When A20 cells were preincubated with 20 $\mu$g/ml (rs4-1BB, the binding of 4-1BB-AP to A20 cells was blocked by approximately 70% (FIG. 35).

A Western analysis of rs4-1BB (FIG. 33) indicated that rs4-1BB existed as several different immunoreactive species; this may be due to differential posttranslational modifications indicative of the baculovirus system. For this reason, the binding affinity of rs4-1BB compared to 4-1BB-AP may differ. These data, in conjunction with experiments demonstrating selective binding of 4-1BB-AP to mature B cells and macrophages (FIG. 34), suggest 4-1BB-AP binds specifically.

In Situ Staining of 4-1BB-AP Protein Bound to A20 cells. The binding of 4-1BB-AP to A20 cells was next examined by in situ staining in order to assess the istribution of bound 4-1BB-AP. A20 or DIO.G4 cells were incubated with equal levels of 4-1BB-AP or AP activity. After washing, the cells were spun onto slides with a cytospinner, fixed, and analyzed for AP activity. A20 cells incubated with 4-1BB-AP showed cell-surface staining, representative of AP activity. A20 cells incubated with AP alone did not exhibit any observable staining. On the contrary, DlO,G4 cells incubated with 4-1BB-AP or AP alone showed no observable cell-surface staining (data not shown). In all cases, the nuclei were counter-stained with methyl green. These data indicate A20 cells express binding sites for 4-1BB-AP on the cell surface.

Costimulation of primed splenic B cells with paraformaldehyde-fixed sf21-4-1BB cells. Since 4-1BB bound to anti-$\mu$-treated B cells, experiments were performed to determine whether 4-1BB may deliver growth-inducing signals to B cells. Small resting B cells were stimulated with various concentrations of anti-$\mu$ in the absence or presence of paraformalehyde-fixed SF21-4-1BB or SF21-wt cells.

FIG. 36 shows the costimulation of anti-r-primed B cells with fixed-SF21-4-1BB cells. 1×10$^5$ splenic B cells were incubated in medium alone (C) or stimulated with 0.1-IO $\mu$g/ml of anti-i in the absence or presence of 5×10$^4$ -SF21-wt or SF21-4-1BB cells. At 72 hours, cultures were pulsed with 1 $\mu$Ci per well $^3$H-thymidine or 16–18 hours, harvested, and $^3$H-thymidine was measured by liquid scintillation counting.

FACS analysis indicated that at 2 days postinfection, >80% of the infected SF21 cells expressed 4-1BB on the cell surface (data not shown). 4-1BB functioned as a costimulator of B-cell proliferation when cells were incubated with optimal (10 $\mu$g/ml) or suboptimal (0.1-I.0 $\mu$g/ml) concentrations of anti-$\mu$.

SF21 cells did not exhibit efficient costimulator activity when infected with wild type baculoviruses (FIG. 36, compare SF21-wt to SF21-4-1BB stimulations). SF21-4-1BB did not synergize with TPA, ionomycin, TPA plus ionomycin or suboptimal concentrations of LPS (data not shown) in inducing B-cell proliferation. A synergistic response also resulted when B cells were stimulated with SF2i+1BB and DlOs (data not shown). This study demonstrates that 4-1BB is capable of delivering a signal(s) to B cells which synergizes with those generated by the addition of anti-$\mu$.

DISCUSSION

The characterization of receptor.counter receptor interactions during contact between T cells and B cells or other APCs, is only in its infancy. 4-1BB may represent another cell-surface molecule involved in T cell-APC interactions. The 4-1BB-AP fusion protein specifically bound to mature B-cell lines, anti-$\mu$-activated primary B cells, and mature macrophage-cell lines. 4-1BB-AP bound at low or insignificant levels to immature B- and macrophage-cell lines, T-cell clones, T-cell lines, primary culture T cells, and various nonlymphoid-cell lines. Since 4-1BB-AP binds to mature B cells and macrophages, it is possible that signals delivered upon 4-1BB binding may modulate APC functions in some way. This possibility remains to be explored.

Chalupny and colleagues (132) have proposed that 4-1BB Rg, a fusion protein consisting of the extracellular domain of 4-1BB and the Fc region of human IgG, bound to the extracellular matrix (ECM). The highest levels of 4-1BB Rg binding was to human vitronectin. In data not shown, an ELISA was performed using 4-1BB-AP and human vitronectin (Yelios Pharmaceuticals/GIBCO-BRL, Grand Island, N.Y.) immobilized at 0.007 $\mu$g-10 $\mu$g per well on microtiter plates. No binding of 4-1BB-AP based on AP activity was observed. To rule out the possibility that 4-1BB-AP was binding to proteins extrinsically attached to the cell surface (possible extracellular matrix components), B-cell lymphomas were washed in acid conditions prior to the binding assay (115). 4-1BB-AP still bound specifically to mature B-cell lymphomas (data not shown). We are currently determining whether a 4-1BB-ligand specifically expressed on B cells and macrophages exists, and whether 4-1BB-AP may bind to the ECM under particular binding conditions. It is possible that the ECM could facilitate the binding of 4-1BB to a specific cell-surface ligand.

B cells and helper T cells interact with each other through receptors on B cells binding to their specific counter-receptors on T cells. It is thought that this interaction results in a cascade of biochemical signaling relays between these two cell types (78). As this interaction proceeds, these cells become committed to enter the S phase of the cell cycle. Initial interactions between TCR and CD4 on T cells, and processed antigen-MHC II on B cells, do not result in B cells capable of entering the cell cycle (116). However, studies from in vitro systems suggest that once Th cells are stimulated, they express newly synthesized or modified cell-surface molecules capable of inducing B cells to enter the cell cycle (22, 23). This T-cell function is not antigen-specific or MHC-restricted (24). In addition, soluble factors are not required for the activated Th induction of B-cell activation (21). Once B cells enter the cell cycle, IL-4 induces B cells to progress from $G_1$ to S phase. The ability of activated T cells or T-cell membranes to promote the entry of B cells into the cell cycle can be blocked by either cycloheximide or cyclosporin A treatment (117, 118). These newly expressed membrane proteins appear to be "lymphokine-like" in their induction characteristics.

4-1BB has expression properties which meet the requirements of a B-cell costimulator. 4-1BB is inducible by anti-CD3 or TCR-mediated T-cell stimulation, and its expression is sensitive to cyclosporin A as well as cycloheximide treatment (90). Interestingly, paraformaldehyde-fixed SF21-4-1BB cells, synergized with anti-$\mu$ in inducing B-cell proliferation. The costimulation of splenic B cells by SF21-4-1BB occurred at optimal (10 $\mu$g/ml) and suboptimal (1.0–0.1 $\mu$g/ml) doses of anti-$\mu$. The addition of SF21-4-1BB cells to resting B cells, did not result in significant B-cell proliferation. SF21-4-1BB cells did not synergize with TPA or ionomycin, or suboptimal concentrations of LPS in inducing B-cell proliferation (data not shown).

Although the baculovirus system has been used to express large amounts of recombinant soluble proteins, this system may be utilized for the expression of recombinant cell-surface proteins. The baculovirus infection provides a convenient means to express uniformity high levels of recombinant protein on a per cell basis. It is noteworthy, that the addition of SF21 cells alone did not result in significant levels of costimulation. This can be a potential problem when using cos- or L- cell lines which can exhibit strong costimulator activity on their own.

Another member of the NGFR superfamily, CD40, is expressed on B cells and interacts with gp39, a molecule expressed on activated T cells. The cDNAs encoding the murine (84) and human (26) gp39 proteins have been cloned; this cell surface molecule is a type II membrane protein with homology to tumor necrosis factor. Noelle et al. (85) found that a CD40-inununoglobulin fusion protein, is capable of blocking T cell-induced B-cell proliferation and differentiation in a dose-dependent manner. Armitage et al (84) have isolated a cDNA for murine gp39 and showed that gp39 could induce B-cell proliferation in the absence of co-stimuli, and result in IgE production in the presence of IL-4-. Hollenbaugh et al. (120) have shown that COS cells transfected with human gp 39 can synergize with either TPA or anti-CD20 in inducing human B-cell proliferation and is able to stimulate B cells without a costimulator only at low levels. These data indicate that CD40 may be one of the B-cell-surface molecules that transmit signals during physical contact with T cells.

Cell-surface receptors communicate with their external milieu by interacting either with soluble factors or other cell surface molecules expressed on neighboring cells. The role of biochemical signals delivered by cell-cell contact versus those delivered by soluble factors interacting with cell surface receptors is not clear. The NGFR superfamily is unusual for the TNFR I and II as well as the NGFR bind to more than one ligand. The TNFRs I and II both bind to TNF-$\alpha$ and TNF-R (48). The NGFR binds to NGF, brain-derived neurotrophic factor, and neurotrophin-3 (105).

In addition, one ligand may function as both a cell surface and soluble ligand. Recent evidence on the CD4-0 ligand, gp39, suggests that this ligand can exist as a membrane bound as well as a soluble ligand (121). It may be possible that 4-1BB is secreted and interacts with B cells in a soluble form as well as a membrane bound form. A member of the NGFR receptor family, CD27, which is expressed on T cells, is secreted in addition to being expressed on the cell surface (122). It is also possible that more than one 1 ligand (soluble and cell surface) may bind to 4-1BB.

In the present study, we have shown that 4-1BB-AP binds to the surface of a variety of B-cell and macrophage-cell lines, and activated primary culture B cells. 4-1BB may in fact, act as a costimulator of B-cell activation. Future experiments will focus on characterization of the 4-1BB binding site(s) and determining if 4-1BB is involved in thymus dependent-B-cell proliferation and differentiation.

Appendix to References Incorporated by Reference

1. Glasebrook, A. and Fitch, F. (1980) *J. Exp. Med.* 151, 876–895.
2. Lancki, D. W., Lorber, M. I. Loken, M. R., & Fitch, F. W. (1983) *J. Exp. Med.* 157,921–935 and Moldwin, R. L., Lancki, D. W., Herold, K. C. & Fitch, F. W. (1986) *J. Exp. Med.* 163,1566–1582.
3. Gillis, S., Ferm, M. M., Ou, W. & Smith, K. A. (1978) *J. Immunol* 120,2027–2032.
4. Chirgwin, J. M., Przybyla, A. E., MacDonald, R. J. & Rutter, W. J. (1979) *Biochemistry* 18, 5294–5299)

5. Aviv, H. & Leder, R. (1972) *Proc. Natl.Acad. Sci USA* 69,1408–1412.
6. Land, H., Grez, M., Hauser, H., Lindenmaier, W. & Schutz, G. (1981) *Nucleic Acids Res.* 9, 2251–2266.
7. Huynh, T. V., Young, R. A. & Davis, R. W. (1985) in *DNA Cloning: A Practical Approach*, ed. Glover, D. (IRL, Arlington, Va.), Vol 1, pp. 49–78.
8. Davis, R. W., Botstein, D. & Roth, J. R. (1980) *Advanced Bacterial Genetics* (Cold Spring Harbor Laboratory, Cold Spring Harbor, N.Y.), pp. 106–107.
9. Maniatis, R., Fritsch, E. F. & Sambrook, J. (1982) *Molecular Cloning: A Laboratory Manual* (Cold Spring Harbor Laboratory, Cold Spring Harbor, N.Y.), pp. 382–389.
10. Lehrach, H., Diamond, D., Wozney, J. M. & Boedtker, H.(1977) *Biochemistry* 16, 4743–4751.
11. Feinberg, A. P. & Vogelstein, B. (1983) *Anal. Biochem.* 132,6–13.
12. Grass-Bellard, M., Oudet, P. and Chambon, P. (1973) *Eur.J. Biochem.* 36,32–38.
13. Southern, E. (1975) *J. Mol. Biol.* 98,503–517.
14. Farrar, J., Fuller-Farrar, J., Simon, P., Hilfiker, M., Stadler, B. and Farrar, W. (1980) *J. Immunol.* 125, 2555–2558.
15. Kim, K., Kanellopoulos-Langevin, C., Merwin, R., Sach, D. and Asofsky, R. (1979) *J. Immunol.* 122, 549–554.
16. Henkart, P., Millards, P., Reynolds, C. and Henkart, M. (1984) *J. Exp. Med.* 160,75–93.
17. Kwon, B. S., & Weissman, S. M. (1984) *J.Virol.* 52, 1000–1004.
18. Henkart, P. A., Millard, P. J., Reynolds, C. W. & Henkart, M. P. (1984) *J. Exp. Med.* 160,75–93.
19. Messing, J., Crea, R. and Seeburg, P. (1981) *Nucleic Acids Res.* 9,309–322.
20. Sanger, F., Nicklen, S. and Coulson, A. (1977) *Proc. Natl. Acad. Sci USA*74,5463–5467.
21. Biggin, M., Gison, T. and Hung, G. (1983 *Proc. Natl. Acad. Sci. USA* 80,3963–3965.
22. Zurawski, G., Benedik, M., Kamb, B. J., Abrams, J. S., Zurawaki, S. M. and Lee, F. D. (1986) *Science* 232.772–775.
23. Kinachi, T. (1986) *Nature* 325,70–73.
24. Gershenfeld, H. K. and Weissman, I. L. *Science* (1986) 232,854–858.
25. Lobe, C. G., Finlay, B. B., Paranchych, W., Paetkau, V. M. and Bleackley, R. C. (1986) *Science* 232,858–861.
26. Kwon, B., Kestler, D., Lee, E., Wakulchik, M. and Young J. (1988) *J. Exp. Med*) (1988) (In press).
27. Blobel, G. and Dobberstein, B., (1975) *J. Cell Biol.* 67, 852–862 and Steiner, D., Quinn, P., Chan, S., Marsh, J. and Tager, H. (1980) *Ann. N.Y. Acad. Sci.* 34,1–16.
28. Shaw, G. and Kamen, R. (1986) *Cell* 46,659–667.
29. Elliott, J., Lin, Y., Mizel, R., Bleackley, R., Harnish, D. and Paetkau, V., Science. (1984) 226:1439 and Granelli-Piperno, A., Inaba, K. and Steinman, R., *J. Exp. Med.* (1984) 160:1792.
30. Kozak, M. (1984) *Nucleic Acids Res.* 12,857–872.
31. Hedrick, S., Nielsen, E., Kavaler, J., Cohen, D. and Davis, M. (1984) *Nature*. 35 308,153–158 and Cohen, D., Steinberg, A., Paul, W. and Davis, M. (1985) *Nature* 314,37–374.
32. Prystowsky, M., Ely, J., Beller, D., Eisenber, L., Goldman, J., Goldman, M., Goldwasser, E., Ihle, J., Quintans, J., Remold, M., Vogel, S. and Fitch, F. (1982) *J. Immunol.* 129,2337–2344.
33. Morris, P., *Transplantation.* (1981) 32:349; Orosz, C., Fidelus, R, Roopenian, D., Widmer, M., Ferguson R. and Bach, F., (1982) *J. Immunol.* 129:1865 and Hess, A., Tutschka, P., Pu, Z. and Santos, G., *J. Immunol.* (1982) 128:360.
34. Kronke, M., Leonard, W., Depper, J., Arya, S. Wong-Stahl, F., Gallo, R., Waldmann, T. and Greene, W., *Proc. Natl. Acad.Sci. USA* (1984) 81:5214.
35. Wiskocil, R., Weiss, A., Imboden J., Kamin-Lewis, R. and Stobo, J., *J. Immunol.* (1985) 134:1599.
36. Foulis, A. K., Liddle, C. N., Farquharson, M. A., Richmond, J. A., and Weir, R. S. 1986. The histopathology of the pancreas in type I (insulin-dependent) diabetes mellitus: a 25-year review of deaths in patients under 20 years of age in the United Kingdom. Diabetologia. 29:267–274.
37. Gepts, W. 1965. Pathologic anatomy of the pancreas in juvenile diabetes mellitus. Diabetes 14:619–633.
38. Wolpe, S. D., G. Davatelis, B. Sherry, B. Beutler, D. G. Hesse, H. T. Hguyen, L. L. Moldawer, C. F. Nathan, S. F. Lowry, and A. Cerami. 1988. Macrophages secrete a novel heparin-binding protein with inflammatory and neutrophil chemokinetic properties. J. Exp. Med. 167:570.
39. Davatelis, G., P. Tekamp-Olson, S. D. Wolpe, K. Hermsen, C. Luedke Gallegos, D. Cort, J. Merryweather, and A. Cerami. 1988. Cloning and characterization of a cDNA for murine macrophage inflammatory protein (MIP), a novel monokine with inflammatory and chemokinetic properties. J. Exp. Med. 167:1939.
40. Sherry, B., P. Tekamp-Olson, C. Gallegos, D. Bauer, G. Davatelis, S. D. Wolpe, F. Masiarz, D. Cort, and A. Cerami. 1988. A resolution of the two components of macrophage inflammatory protein 1, and cloning and characterization of one of these components, macrophage inflammatory protein 1 beta. J. Exp. Med. 168:2251.
41. Wolpe, S. D., B. Sherry, D. Juers, G. Davatelis, R. W. Yurt, and A. Cerami. 1989. Identification and characterization of macrophage inflammatory protein 2. Proc. Natl. Acad. Sci. USA 86:612.
42. Tekamp-Olson, P., C. Gallegos, D. Bauer, J. McClain, B. Sherry, M. Fabre, S. Van Deventer, and A. Cerami. 1990. Cloning and characterization of cDNAs for murine macrophage inflammatory protein 2 and its human homologues. J. Exp. Med. 172:911.
43. Zhou, F. C. and Buckwald, N., Connectivities of striatal grafts in the adult rat brain: A rich afference and scant nigro striatal efference, Brain Res. 504 (1989) 125–130.
44. Zhou, F. C. and Azmitia, E. C., Neurotrophic factor for serotonergic neurons prevents degeneration of grafted raphe neurons in the cerebellum, Brain Res. 507 (1990) 301–308.
45. Radeke, M. J., T. P. Misko, C. Hus, L. A. Herzenbert, and E. M. Shooter, 1987, Gene transfer and molecular cloning of the rat nerve growth factor receptor, Nature 325:593.
46. Stamenkovic, I., E. Clark, and B. Seed, 1989, A B-lymphocyte activation molecule related to the nerve growth factor receptor and induced by cytokines in carcinomas. EMBO J. 8:1403.
47. Mallett, S., S. Fossum and A. Barclay, 1990, Characterization of the MRC OX40 antigen of activated CD4 positive T lymphocytes-a molecule related to nerve growth factor receptor, EMBO J. 9:1603.
48. Schall, T. J., M. Lewis, K. J. Koller, A. Lee, G. C. Rice, G. H. W. Wong, T. Gatanaga, G. A. Granger, R. Lentz, H. Raab, W. J. Kohr and D. V. Goeddel, 1990, Molecular cloning and expression of a receptor for human tumor necrosis factor, Cell 61:361.
49. Sugita, K., Y. Torimoto, Y. Nojima, J.Daley, S.Schlossman and C. Morimoto, 1991, The 1A4 moleculte (CD27) is involved in T cell activation, J. Immunol. 147:1477

50. Watanabe-Fukunaga, R., C. Brannan, N. Itoh, S. yonehara, N. Copeland, N. Jenkins and S. Nagata, 1992, The cDNA structure, expression and chromosomal assignment of the mouse Fas antigen, J. Immunol. 148:1274.

51. Howard, S., Y. Chan and G. Smith, 1991, Vaccinia virus homologous of the shope fibroma virus inverted terminal repeat proteins and a discontinuous ORF related to the tumor necrosis factor receptor family, Virology 180:633.

52. Durkop, H., U. Latza, M. Hummel, F. Eitelbach, B. Seed and H. Stein. 1992, Molecular cloning and expression of a new member of the nerve growth factor receptor family that is characteristic for Hodgkin's disease, Cell 68:421.

53. Miller, D. S., P. Safer and L. K. Miller, 1986, An insect baculovirus host-vector system for high level expression of foreign genes, In Genenic Engineering, Vol. 8, Setlow, J. K. and Hollaender, A,. eds. Plenum Publishing Corp., New York, pp. 277–298.

54. Mishell, B. B. and S. M. Shiigi, 1980, Selected Methods in Cellular Immunolgy, W. H. Freeman and Company, New York, pp. 182–185.

55. Defranco, A. L., E. S. Raveche, R.Asofasky and W. E. Pavel, 1982, Frequency of B lymphocytes responsive to anti-immunoglobulin, J. Exp. Med. 155:1523.

56. Kohler, G. and G. Milstein, 1975, Continuous cultures of fused cells secreting antibody of predefined specficity, Nature 256:495.

57. Smith, C., T. Davis, J. Wignall, W.Din, T. Farrah, C. Upton, G. McFadden and R. G. Goodwin, 1991, T2 open reading farme from shope fabroma virus encodes a soluble form of the TNF receptor, Biochem. Biophys, Res. Commun. 176:335.

58. Crabtree, G. R., 1989, Contingent genetic regulatiory events in T lymphocyte activation, Science 243:355.

59. Ebina, Y., L. Ellis, K. Jaruagin, M. Edery, L. Graf, E. Clauser, J. On, F. Marizrz, Y. W. Kan, J. D. Goldfine, R. A. Roth and W. J. Rutter, 1985, The human insulin receptor cDNA: the structural basis for hormone-activated transmembrane signalling, Cell 40:747.

60. Vassali, R., R. Tedghi, B. Listowska-Bernstein, A. Tartakoff and J. C. Jaton, 1979, Evidence for hydrophobic region within heavy chains of mouse B lymphocyte membrane-bound IgM, *Proc. Natl. Acad. Sci. USA* 76:5515.

61. Haskins, K., R. Kubo, J. White, M. Pigeon, J. Kappler and P. Marrack, 1983, The major histocompatability complex-restricted antigen receptor on T cells I Isolation with monoclonal antibody, *J. Exp. Med.* 157:1149.

62. Lesslaver, W. and H. Gmunder, 1986, Biochemical characterization of the 9.3 antigens of human T-cells: stimultaneous expression of disulfide-bonded 90-Kiladalton dimers and free subunits at the cell surface, Mol. Immunol. 23:271.

63. Van Lier, R., J. Borst, T. Vroom, H. Klein, P. Mourik, W. Zeijlemaker and C. Melife, 1987, Tissue distribution and biochemical and functional properties of Tp55 (CD27) a novel T cell differentiation antigen, J. Immunol. 139:1589.

64. Banchereau, J., P. Paoli, A., Valle, E. Garcia and F. Roussel, 1991, Long-term human B cell lines dependent on interleukin-4 and antibody to CD40, Science 251:70.

65. Moeller, D. L., M. K. Jenkins and R. H. Schwartz, 1989, Clonal expansion versus functional colonal inactivation: a co-stimulatory signalling pathway determines the outcome of T cell antigen receptor occupancy, Ann. Rev. Immunol. 7:445.

66. June, D. H., J. A. Ledbetter, P. S. Linsley and C. B. Thompson, 1989, Role of CD28 receptor in T cell activation, Immunol. Today 11:211.

67. Yang, L., B. Jones, A. Aruffo, K. M. Sullivan, P. S. Linsley and C. A. Janeeway, Jr., 1992, Heat stable antigen is a co-stimulatory molecule for CD4 T cell growth, J. Exp. Med. 175:437.

68. Yamori, T., 1992, Molecular mechanisms for generation of neural diversity and specificity: foles of polypeptide factors in development of post-mitotic neurons, Neurosic. Res. 12:545.

69. Liu, Y. J., D. E. Joshua, G. T. Williams, C. A. Smith, J. Gordon and I. C. M. MacLennan, 1989, Mechanism of antigen-driven selection in germinal centres, Nature, 342:929.

70. Jabara, H. H., s. M. Fu, R. S. Geha and D. Vercelli, 1990, CD40 and IfE: synergism between anti-CD40 momoclonal antibody and interleukin 4 in the induction of IgE synthesis by highly purified human B cells, J. Exp. Med. 172:1861.

71. Defrance, R., B. Vanbervliet, F. Briere, I. Durnad, F. Roussle and J. Banchereau, 1992, Interleukin 10 and transforming growth factor β cooperate to induce anti-CD40 activated naive human B cells to secrete immunoglobulin A, J. Exp. Med. 175:671.

72. Weber, J. R., Bell, G. M., Han, M. Y., Pawson, T and Imboden, J. B.,1992, J. Exp. Med. 176:373–379.

73. Hatakeyama, M., Kono, T., Kobayashi, N.,Jawaharn, A., Levin, S. D., Permutter, R. M and Taniguchi, T., 1991, Science 252:1523–1528.

74. Burgess, K. E., Yamamoto, M., Prasad, K. V. S. and Rudd, C. E., 1992, Proc. Natl. Acad. Sci, USA, 29:9311–9315.

75. Bell, G. M., Bolen, J. B. and Imboden, J. B., 1992, Mol. Cell. Biol 12:5548:5554.

76. Molina, R. J., Kishihara, K., Sideroviski, F. P., Ewijk, W. V., Harendran, A., Timms, E., Wakeham, A., Paige, C. J., Hartmann, K-U., Veillette, A., Davidson, D. and Mak, T. W., 1992, Nature 357:161–164.

77. Veillette, A., Brookman, M. A., Herak, E. M. and Bolen, 1988, Cell 55:301–308.

78. Noelle, R. J., and Snow, E. C., 1991, The FASEB J. 5:2770–2776.

79. Springer, T. A, 1990, Nature 346:425–434.

80. Bierer, B. E., Sleckman, B. P., Ratnofsky, S. E. and Burakoff, S. J., 1989, Annu. Rev. Immunol. 7:579–599.

81. Van de Veide, H., von Hoegen, I., Luo, W., Parnes, J. R. and Thielemans, K., 1991, Nature 351:662–665.

82. Linsley, P. S., Brady, W., Grosmaier, L., Aruffo, A., Damle, N. K. and Ledbetter, J., 1991, J. Exp. Med. 173:721–730.

83. Linsley, P. S., Brady, W., Urnes, M., Grosmaire, L. S., Damle, N. K. Ledbetter, J.A., 1991, J. Exp. Med. 174:561–569.

84. Armitage, R., Fanslow, W., Strockbine, L., Sato, T., Clifford, K., MacDuff, B., Anderson, D., Gimpel, S., Davis-Smith, T., Maliszewski, C., Clark, E., Smith, C., Grabstein, K., Cosman, D. and Spriggs, M., 191, Nature 357:80–82.

85. Noelle, R. J., Roy, M., Shepherd, D. M., Stamenkovic, I., Ledbetter, J. A. and Aruffo, A., 1992, Proc. Natl. Acad. Sci. USA 89:6550–6554.

86. Kehrl, J. H., L. M. Wakefield, A. B. Roberts, S. Jakowlew, M. Alvarez-Mon, R. Derynck, M. B. Sporn, and A. S. Fauci. 1986. Production of transforming growth factor β by human T lymphocytes and its potential role in the regulation of T cell growth. J. Exp. Med. 163:1037.

87. Smeland, E. B., H. K. Blomhoff, H. Holte, E. Ruud, K. Beiske, S. Funderud, T. Godal, and R. Ohlsson. 1987. Transforming growth factor Type β (TGFβ) inhibits $G_1$ to S transition, but not activation of human B lymphocytes. Exp. Cell. Res. 171:213.

88. Kwon, B. S., Kim, G. S., Prystowsky, M. B., Lancki, D. W., Sabath, D. E., Pan, J., and Weissman, S. M. 1989. Isolation and initial characterization of multiple species of T-lymphocyte subset cDNA clones. Proc. Natl. Acad. Sci. USA 84:2896–2900.

89. Kwon, B. S., and Weissman, S. M. 1989. cDNA Sequences of two inducible T-cell genes. Proc. Natl. Acad. Sci. USA 86:1963–1967.

90. Kwon, B. S., Kestler, D. P., Eshhar, Z., Oh, K., and Wakulchik, M. 1989. Expression characteristics of two potential T cell mediator genes. Cell. Immunol. 121:414–422.

91. Smith, C. A., Davis, T., Anderson, D., Solam, L., Beckmann, M. P., Jerzy, R., Dower, S. K., Cosman, D., and Goodwin, R. G. 1990. A receptor for tumor necrosis factor defines an unusual family of cellular and viral proteins. Science 248:1019–1023.

92. Mallett, S., and Barclay, A. N. 1991. A new superfamily of cell surface proteins related to the nerve growth factor receptor. *Immunology Today*. 12:220–223.

93. Shaw, A. S., Chalupny, J., Whitney, J. A., Hammond, C., Amrein, K. E., Kavathas, P., Sefton, B. A., and Rose, J. K. 1990. Short related sequences in the cytoplasmic domains of CD4 and CD8 mediate binding to the amino-terminal domain of the $p56^{lck}$ tyrosine protein kinase. 1990. Mol. Cell. Bio. 10: 1853–1862.

94. Makino, S., Kunimoto, K., Muraoka, Y., Mizushima, Y., Katagiri, K., and Tochino, Y. 1980. Breeding of a non-obese, diabetic strain of mice. Exp. Anim. 29:1–13.

95. Tochino, Y., Kanaya, T., and Makino, S. 1982. Genetics of NOD mice. In Clinico-Genetic Genesis of Diabetes Mellitus. (Mimura, G., Baba, S., Goto, Y., Kobberling, J., Eds.), Amsterdam, Excerpta Medica, p. 285.

96. Palladino, M. A., Obata, Y., Stockert, E. R., and Oettgen, H. F. 1983. Characterization of interleukin 2-dependent cytotoxic T-cell clones: specificity, cell surface phenotype, and susceptibility to blocking by Lyt antisera. Cancer Res. 43:572–576.

97. Liu, F. T., Zinnecker, M., Hamaoka, T., and Katz, D. H. 1979. New procedures for preparation and isolation of conjugates of proteins and a synthetic copolymer of D-amino acids and immunochemical characterization of such conjugates. Biochemistry 18:690–693.

98. Ihm, S. H., Lee, K. U., and Yoon, J. W. 1990. Studies on autoimmunity for the initiation of B-cell destruction VII. Evidence for antigenic changes on the B-cell leading to the autoimmune destruction of B-cell in BB rat. (In Press).

99. Saiki, R. K., Gelfand, D. H., Stfel, S., Scharf, S. J., Higuchi, R., Horn, G. T., Mullis, K. B., and Erlich, H. A. 1988. Primer-directed enzymatic amplification of DNA with a thermostable DNA polymerase. Science 239:487–491.

100. Yang, Y., Ciarletta, A. B., Temple, P. A., Chung, M. P., Kovacic, S., Witek-Giannotti, J. S., Leary, A. C., Kriz, R., Donahue, R. E., Wong, G. G., and Clark, S. C. 1986. Human IL-3 (multi-CSF): identification by expression cloning of novel hematopoietic growth factor related to murine IL-3. Cell 47:3–10.

101. McCutchan, J. H., and Pagano, J. S. 1968. Enhancement of the infectivity of simian virus 40 deoxyribonucleic acid with diethylaminoethyl-dextran. J. Natl. Cancer Inst. 41:351–357.

102. Chomczynski, P., and Sacchi, N. 1987. Single-step method of RNA isolation by acid guanidinium thiocyanate-phenol-chloroform extraction. Anal. Biochem. 162:156–159.

103. Kwon, B. S., Wakulchik, M., Liu, C-C, Persechini, P. M., Trapani, J. A., Haq, A. K., Kim, Y., and Young, JD-E. 1989. The structure of the mouse lymphocyte pore-forming protein perforin. Biochem. Biophys. Res. Commun. 158: 1–10.

104. Young, L. H. Y., Peterson, L. B., Wicker, L. S., Persechini, P. M., and Young, JD-E. 1989. In vivo expression of perforin by $CD8^+$ lymphocytes in autoimmune disease. Studies on spontaneous and adoptively transferred diabetes in nonobese diabetic mice. J. Immunol. 143:3994–3999.

105. Klein, R., Nanduri, V., Jing, S., Lamballe, F., Tapley, P., Bryant, S., Cordon-Cardo, C., Jones, K. R., Reichardt, L. F. and Barbacid, M., 1991, Cell 66:395–403.

106. Kaye, J., Porcelli, S., Tite, J., Jones, B. and Janeway, Jr., C. A., 1983, J. Exp. Med. 158:836–856.

107. Zhou, F. C. and Azmitia, E. C., Induced homotypic sprouting of serotonegic fibers in hippocampus: II, An immunocytochemical study, Brain Res. 373 (1986) 337–348.

108. Carthew, R. W and Rubin, G. M., seven in absentia, a gene required for specification of R7 cell rate in the Drosophila eye, Cell, 63 (1990) 561–577.

109. Driscoll, D. M. and Williams, J. G., Two divergently transcribed genes of Dictyostelium discoideum are cyclic AMP-inducible and coregulated during development, Mol. and Cell. Biol. 7 (1987) 4482–4489.

110. Donahue, T., Cigan, A., Pahich, E. and Valavicius, B., Mutations at a Zn(II) finger motif in the yeast eIF-2β gene alter ribosomal start-site selection during the scanning process, Cell 54 (1988) 621–632).

111. Maisonpierre, P. C., Belluscio, L., Squinto, S., Ip, N.Y., Furth, M. E., Lindsay, R. M. and Yancopoulos, G. D., Neurotrophin-e: A neurotrophic factor related to NGF and BDNF, Science 247 (1990) 1446–1451.

112. Leibrock, J., Lottspeich, F., Hohn, A., Hofer, M., Hengrer, B., Masiakowski, P., Thoenen, H. and Barde, Y. A., Molecular cloning and expression of brain-derived neurotrophic factor, Nature 341 (1989) 149–152.

113. Flanagan, J. G. and Leder, P., 1990, Cell 63:185–194.

114. Berger, J., Hauber, J., Hauber, R., Geiger, R. and Cullen, B. R., 1988, Gene 66:1–10.

115. Tsudo, M., Kozak, R. W., Goldman, C. K. and Waldmann, T. A., 1986, Proc. Natl. Acad. Sci. USA 83:9694–9698.

116. Noelle, R. and Snow, E., 1990, Immunol. Today 11:361–368.

117. Hodgkin, P. D., Yamashita, L. C., Coffman, R. L. and Kehry, M. R., 1990, J. Immunol. 145:2025–2034.

118. Barlett, W. C., McCann, J., Shephaer, D. M., Roy, M. and Noelle, R. J., 1990, J. Immunol. 145:3956–3962.

119. Owens, T., 1988, Eur. J. Immunol. 18:395–401.

120. Hollenbaugh, D., Grosmaier, L. S., Kullas, C. D., Chalupny, N. J., Braesch-Andersen, S., Noelle, R. J., Stamenkovic, I., Ledbetter, J. A. and Aruffo, A., 1992, EMBO 11:4314–4321.

121. Armitage, R. J., Sato, T. A., Macduff, B. M., Clifford, K. N., Alpert, A. R., Smith, C. A. and Fanslow, W. C., 1992, Eur. J. Immunol. 22:2071–2076.

122. Hintzen, R. Q., deJong, R., Hack, E. E., Chamuleau, M., de Vries, E. F. R., ten Berge, I. J. M., Borst, J. and van Lier, R. A. W., 1991, J. Immunol. 147:29–35.

124. Weiss, A. and Straus, D. B., 1992, Cell 70:585–593.
125. Abraham, N., Miceli, M. C. Parnes, J. R. and Veillette, A., 1992, Nature 350:62–66.
126. Glaichenhus, N., Shastri, N., Littman, D. and Truner, J. M., 1991, Cell 64:511–520.
127. Beyers, A.D., Spruyt, L. L. and Williams, A. F., 1992, Proc. Natl. Acad. Sci. USA 89:2945–2949.
128. Telfer, J. C. and Rudd, C. E., 1991, Science, 254:439–441.
129. Prasad, K. V. S. and Rudd, C. E., 1992, Mol. Cell Biol. 12:5260–5267.
130. Maddon, P. J., McDougal, J. S., Clapham, P. R., Dalgleish, A. G., Jamal, S., Weiss, R. A. and Axel, R., 1988, Cell 54:865–874.
131. Hurley, T. R., Luo, K. and Sefton, B. M., 1989, Science 245:407–409.
132. Chalupny, N. J., Peach, R., Hollenbaugh, D., Ledbetter, J. A., Farr, A. G. and Aruffo, A., 1992, Proc. Natl. Acad. Sci USA 89:10360–10364.
133. Van oers, N. S. C., Garvin, A. M., Davis, C. B., Forbush, K. A., Carlow, D. A., Littman, D. R., Perlmutter, R. M. and Teh, H. S., 1992, Eur. J. Immun. 22:735–743.
134. Leo, U., Foo, M., Sachs, D. M., Samelson, L. M. and Bluestone, J. A., 1987, Proc. Natl. Acad. Sci. USA, 84:1374–1377.
135. Cleveland, D., 1983, Meth. Anzymol. 96:222–229.
136. Fuerst, T. R., Niles, E. G., Studer, F. W. and Moss, 1986, Proc. Natl. Sci. USA 83:8122–8126.
137. Setton, B. M. and Kamps, M. P., 1989, Anal. Biochem. 176:22–27.

The foregoing description has been directed to particular embodiments of the invention in accordance with the requirements of the Patent Statutes for the purposes of illustration and explanation. It will be apparent, however, to those skilled in this art that many modifications and changes will be possible without departure from the scope and spirit of the invention. It is intended that the following claims be interpreted to embrace all such modifications.

I claim:

1. A cDNA sequence which encodes for a murine protein 4-1BB, said murine protein comprising SEQ ID NO:2.

2. The cDNA sequence of claim 1 having a nucleotide sequence as shown in SEQ ID NO:1.

3. The cDNA sequence of claim 1, identified as p4-1BB deposited at the American Type Culture Collection at 12301 Parklawn Drive, Rockville, Md. 20852 under ATCC No.: 67852.

4. A purified and isolated DNA molecule comprising a nucleic acid selected from the group consisting of:
   a) a nucleic acid sequence encoding SE)Q ID NO:2,
   b) a nucleic acid sequence consisting of positions 661–855 of SEQ ID NO:1,
   c) a nucleic acid sequence consisting of positions 1284–1557 of SEQ ID NO:1, and
   d) the complement of (a), (b), or (c).

5. An isolated and purified DNA molecule comprising a DNA sequence encoding a soluble 4-1BB polypeptide comprising the extracellular domain of the amino acid sequence shown in SEQ ID NO:2.

6. An isolated and purified DNA molecular comprising a DNA sequence encoding a soluble 4-1BB polypeptide comprising the extracellular domain of the amino acid sequence shown in SEQ ID NO:2 operably linked to a polypeptide that is not 4-1BB and which is located C-terminal to the soluble 4-1BB polypeptide.

7. The DNA molecule of claim 5 or 6 which further comprises regulatory sequences suitable for expression of the DNA molecule in a host cell, which regulatory sequences are operably linked to the DNA molecule.

* * * * *